(12) United States Patent
Chen

(10) Patent No.: US 12,085,531 B2
(45) Date of Patent: Sep. 10, 2024

(54) NANOSTRUCTURED MODEL DEVICES OF MAKING AND APPLICATIONS IN MONITORING OF ENERGY LANDSCAPES OF TOXIC PROTEIN REFOLDING THERETO

(71) Applicant: Ellen T Chen, Rockville, MD (US)

(72) Inventor: Ellen T Chen, Rockville, MD (US)

( * ) Notice: Subject to any disclaimer, the term of this patent is extended or adjusted under 35 U.S.C. 154(b) by 583 days.

(21) Appl. No.: 17/364,348

(22) Filed: Jun. 30, 2021

(65) Prior Publication Data

US 2022/0018801 A1    Jan. 20, 2022

Related U.S. Application Data

(63) Continuation-in-part of application No. 16/865,340, filed on May 2, 2020, now Pat. No. 11,079,354.

(51) Int. Cl.
| | |
|---|---|
| *G01N 27/327* | (2006.01) |
| *B82Y 35/00* | (2011.01) |
| *B82Y 40/00* | (2011.01) |
| *G01N 33/543* | (2006.01) |

(52) U.S. Cl.
CPC ..... *G01N 27/3278* (2013.01); *G01N 27/3274* (2013.01); *B82Y 35/00* (2013.01); *B82Y 40/00* (2013.01); *G01N 33/5438* (2013.01); *G01N 2333/005* (2013.01)

(58) Field of Classification Search
CPC ....... G01N 27/04–041; G01N 27/4161; G01N 27/045; G01N 27/22; G01N 27/227–228; G01N 27/27; G01N 27/327; G01N 27/3276; G01N 33/48707; G01N 33/48721; G01N 33/48735; G01N 2800/28–2828; A61B 5/40–4094; A61B 5/1468

See application file for complete search history.

*Primary Examiner* — Amar Movva

(57) ABSTRACT

Nanostructured model device of energy sensing and monitoring apparatus comprises arrays of orderly nanotubes parallel oriented forming 3D cross-bar with vertically oriented nanopillars membrane through self-assembly affixed onto an electrode; the membrane comprises active sites of an innate Heat Shock Protein (HSP) cross-linked with conductive polymers on an electrode to be able to monitor toxic protein β-amyloid (Aβ) energy landscape change, and the reversed membrane potential was restored in the presence of an antibiotic drug. By depositing the HSP60 polymer mixtures on a top of a MMP-2 membrane, it promoted a moonlighting protein network that was able to 97.3% impaired Aβ refolding with imprecision 0.05%, which was not depending on antibiotic drug's concentration, wherein to be able to maintain the RMP.

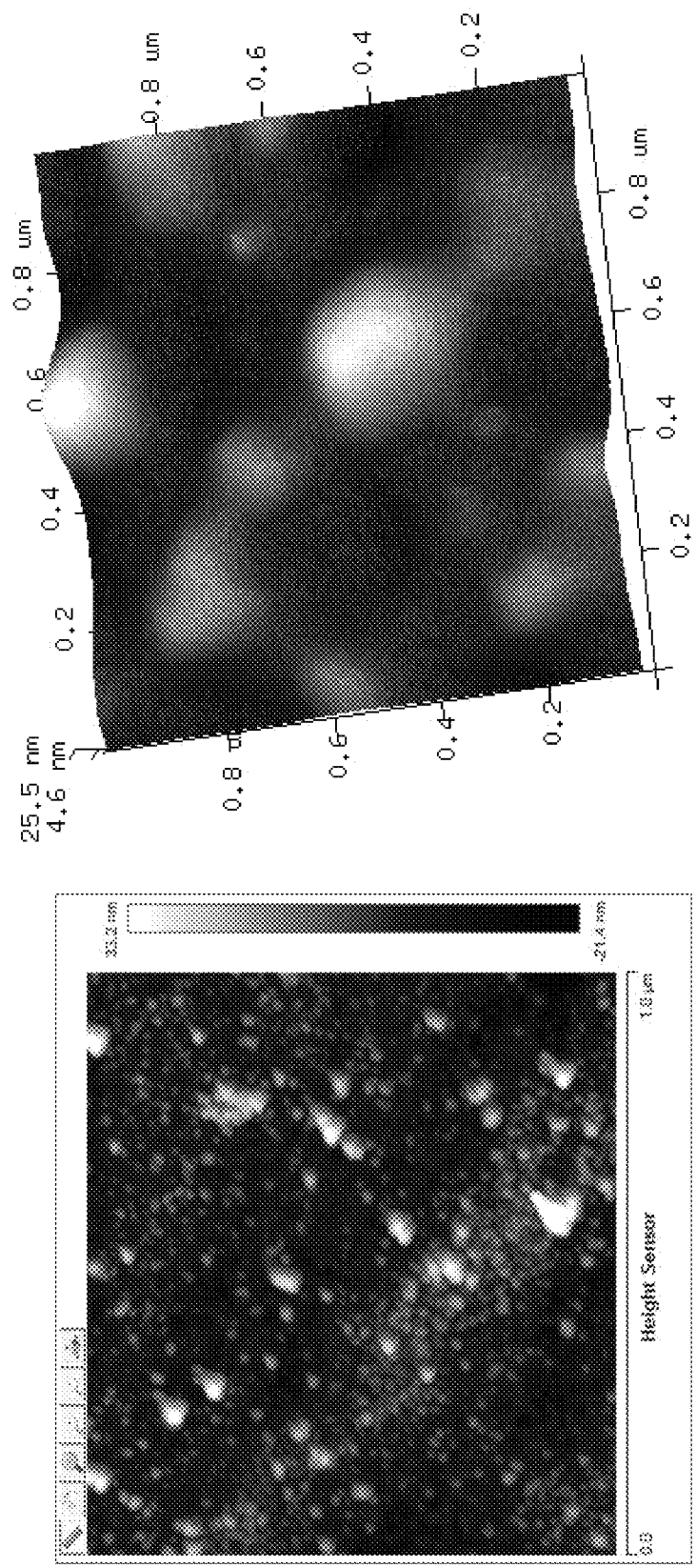

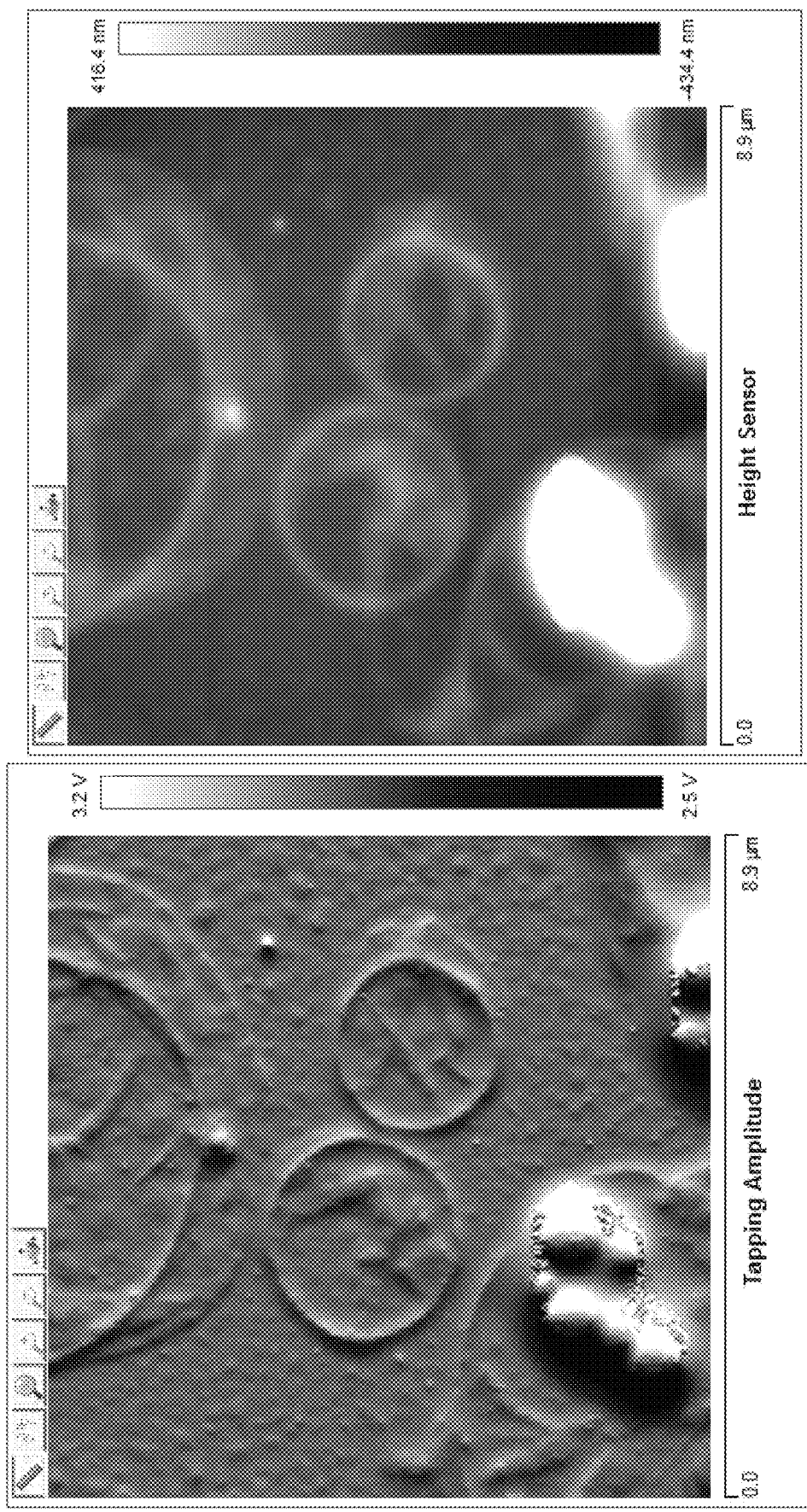

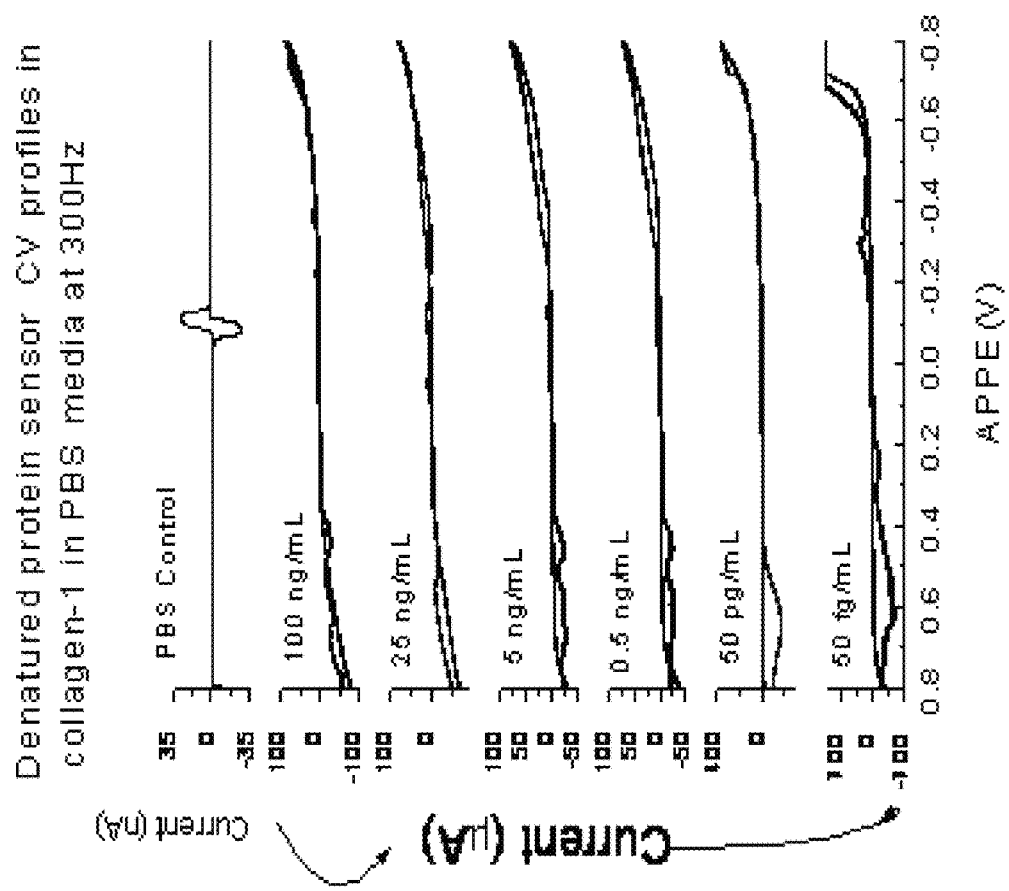
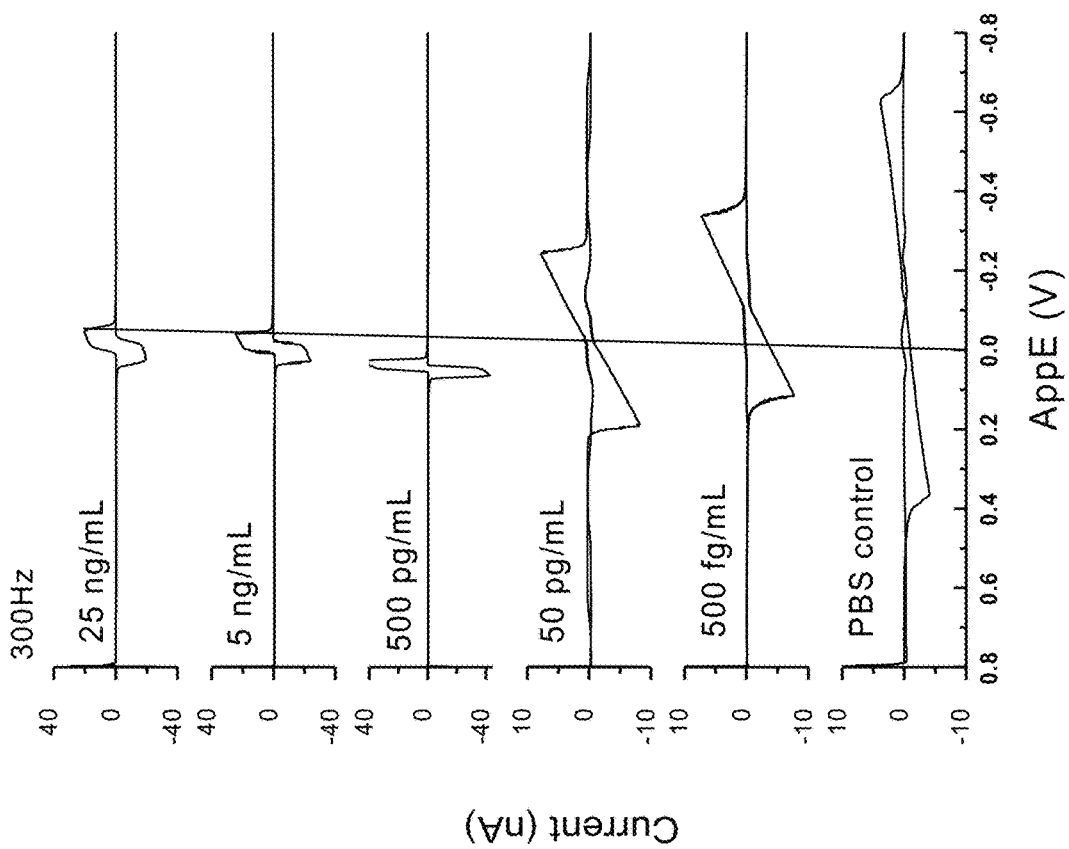
Fig. 14C
Fig. 14D

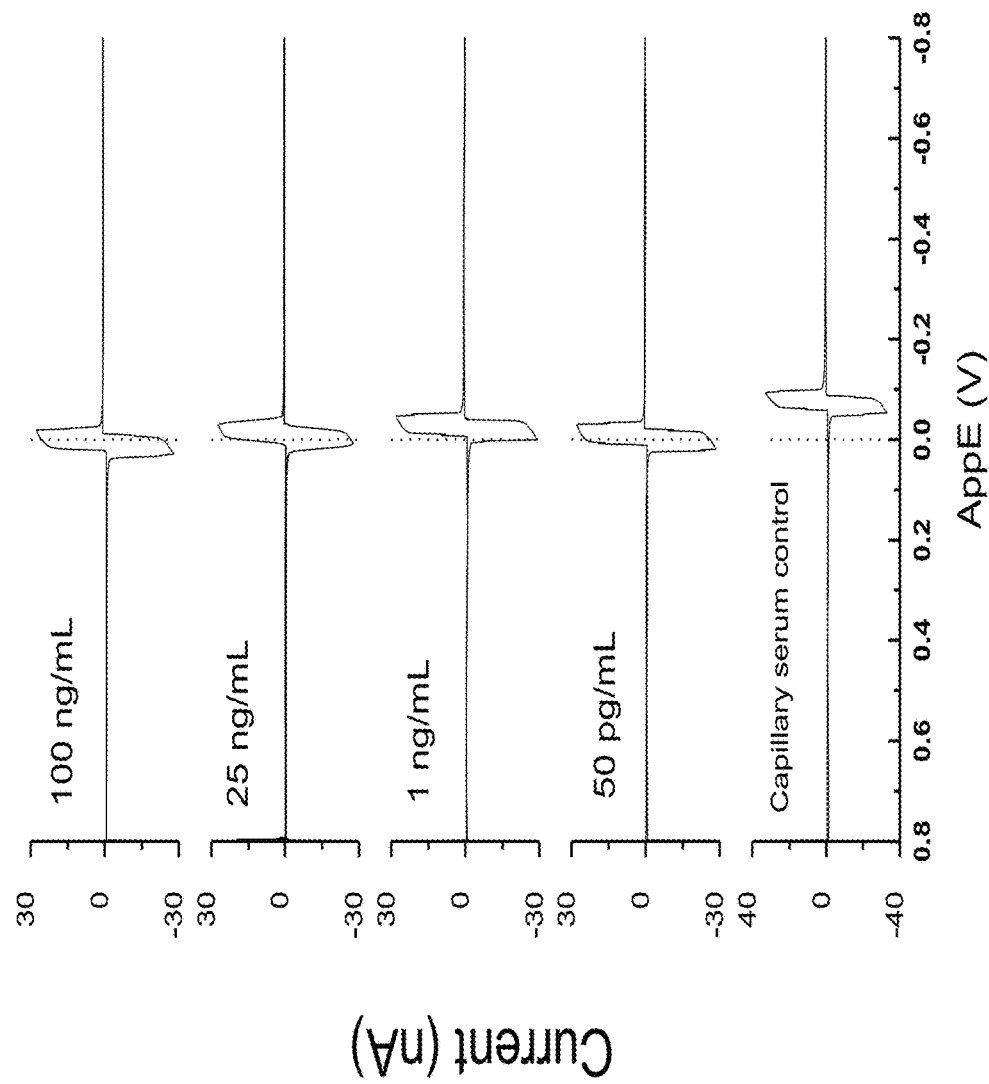

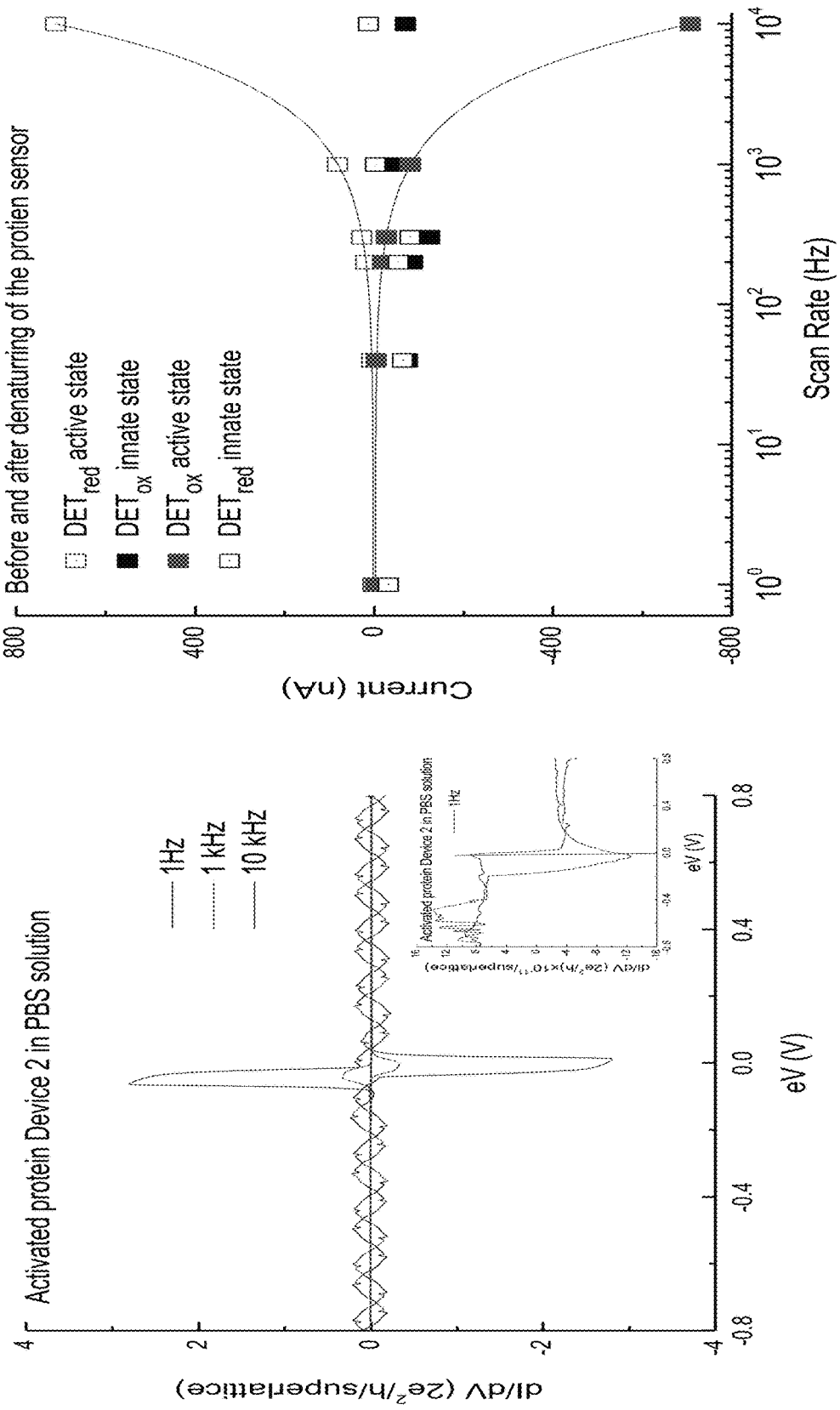

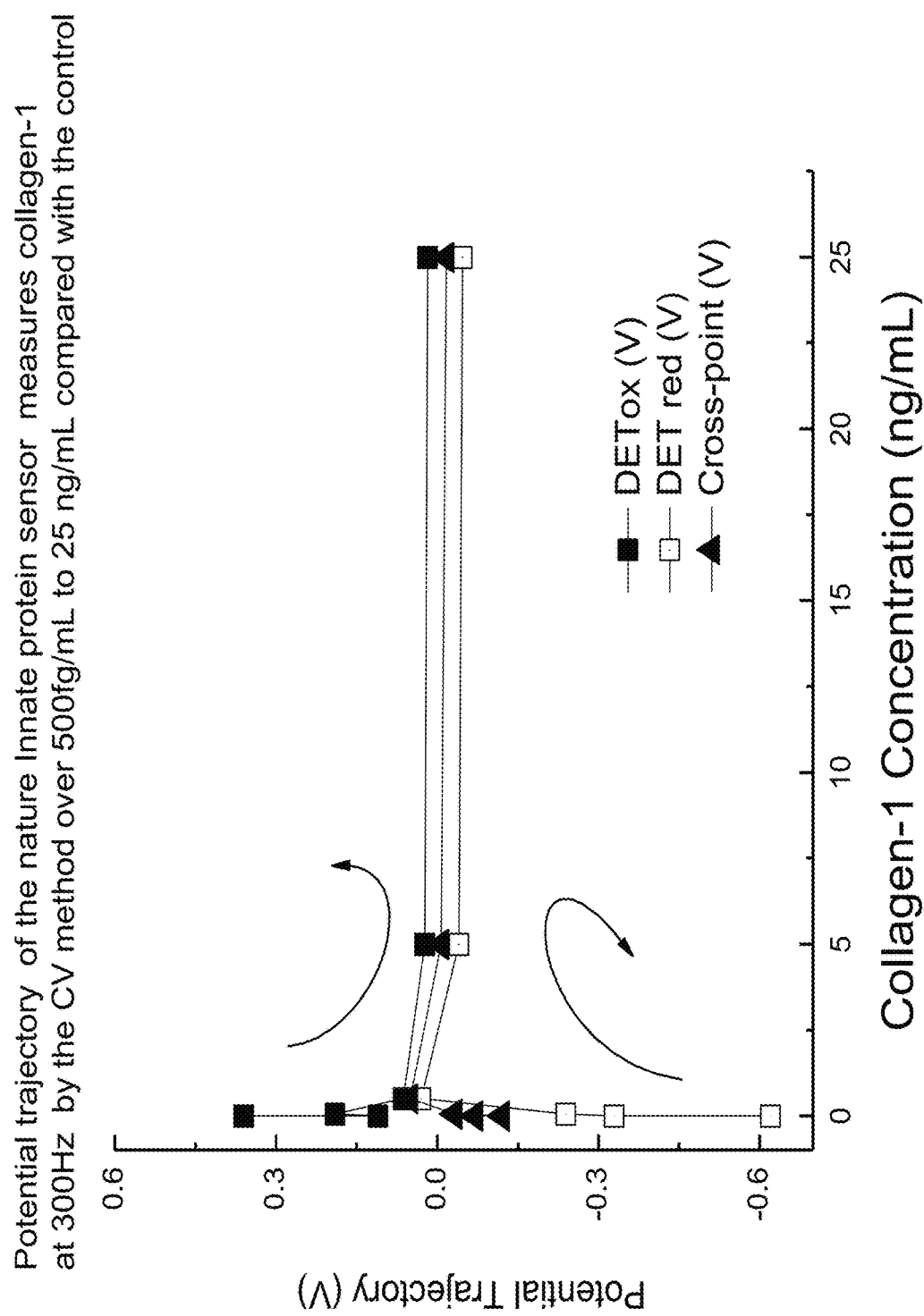

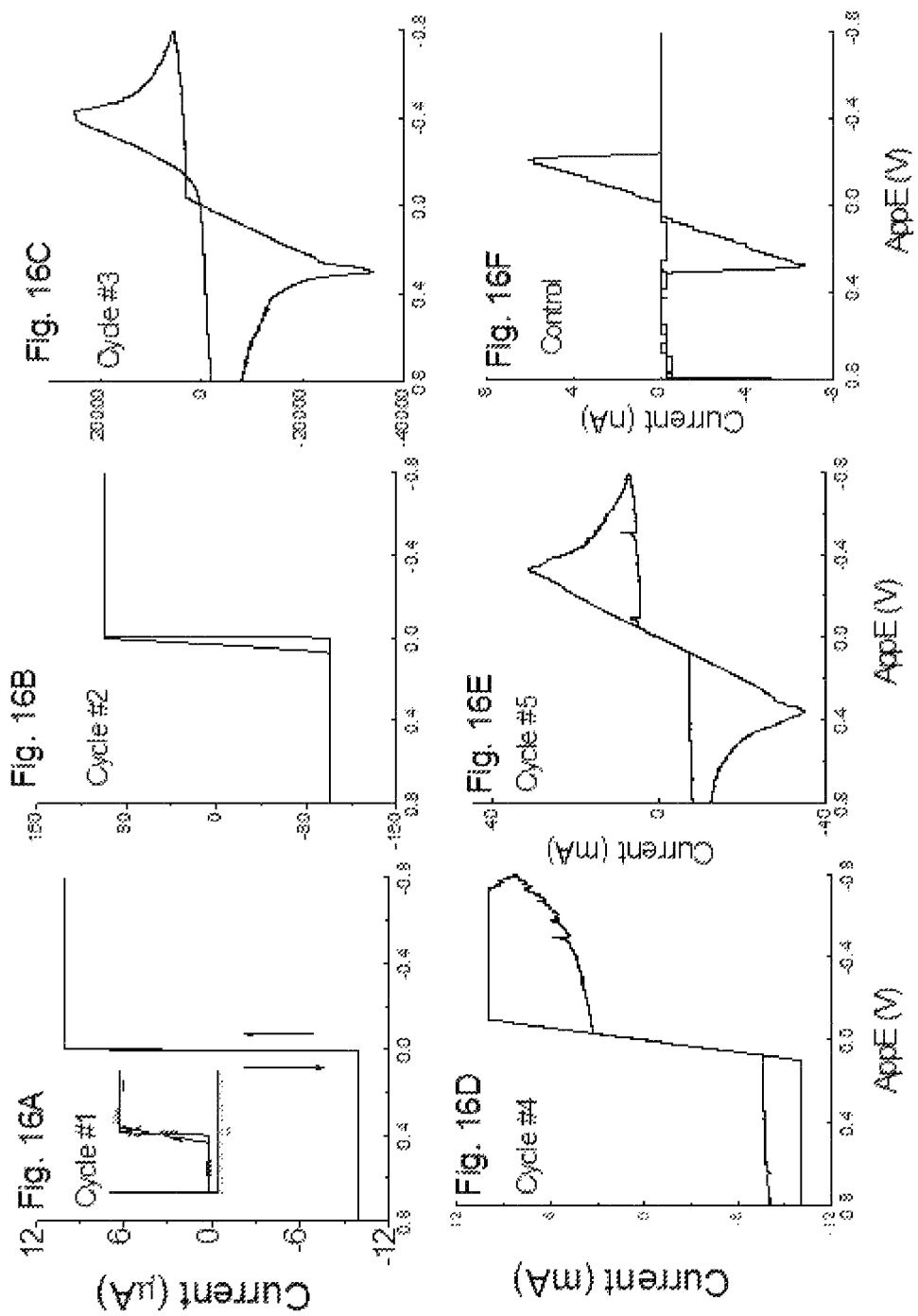

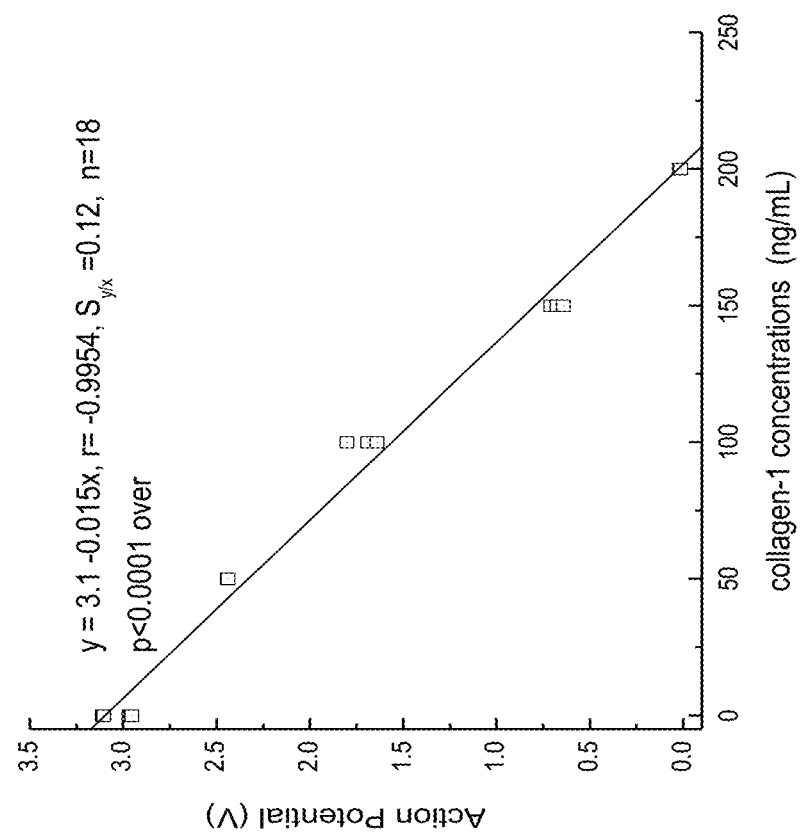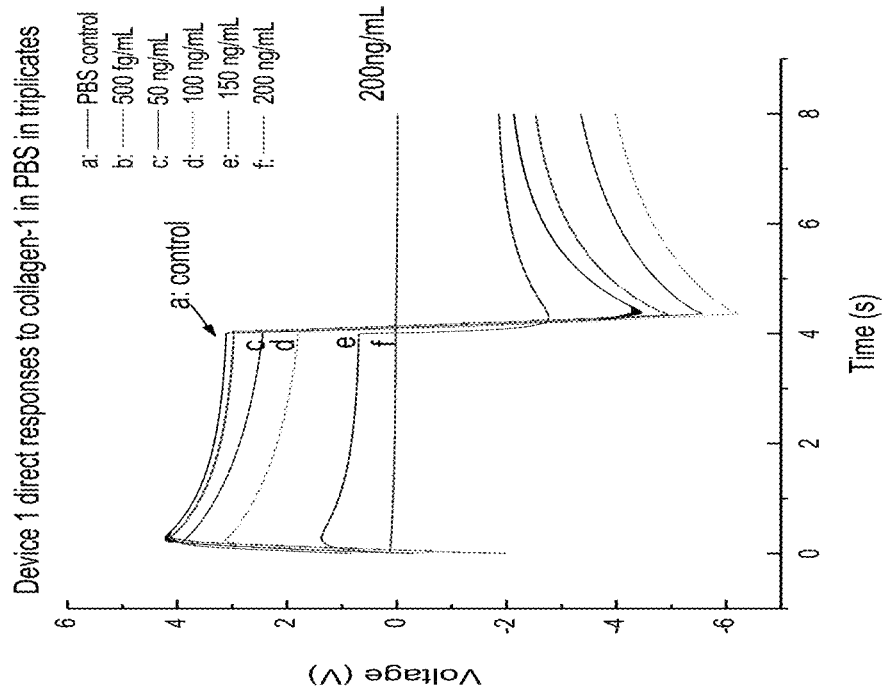

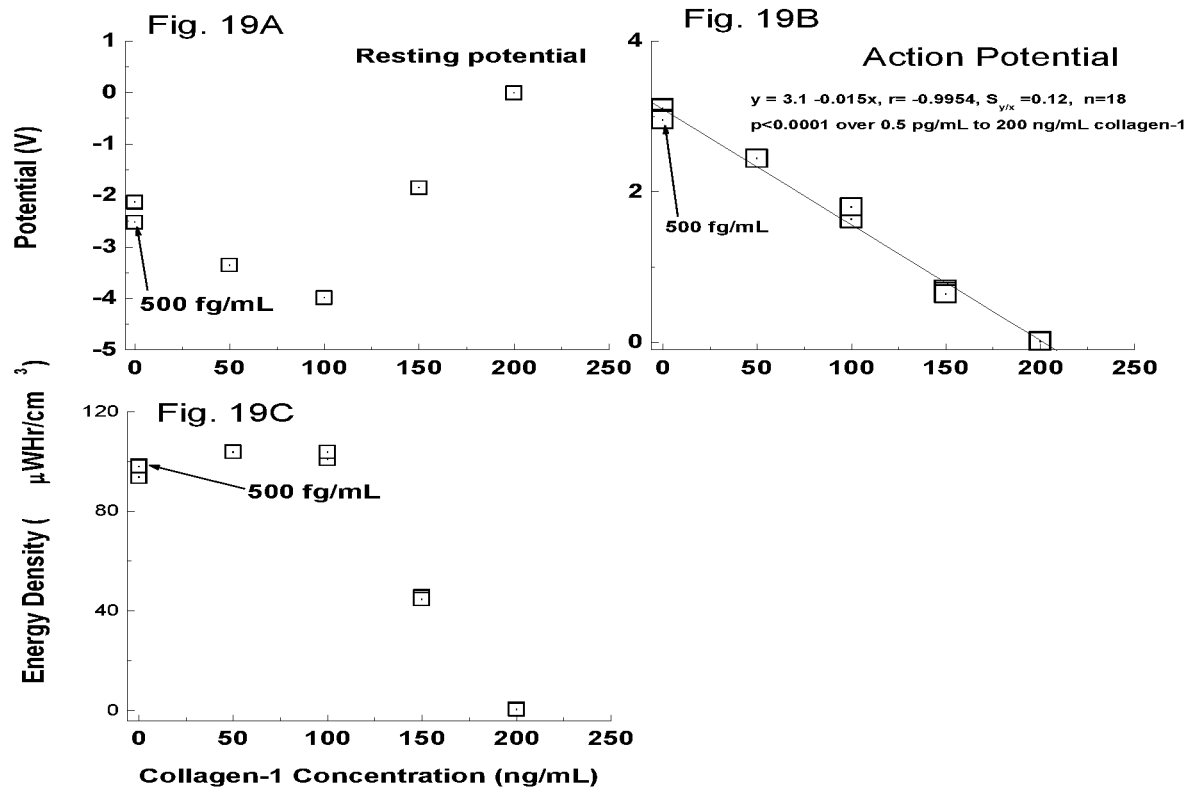

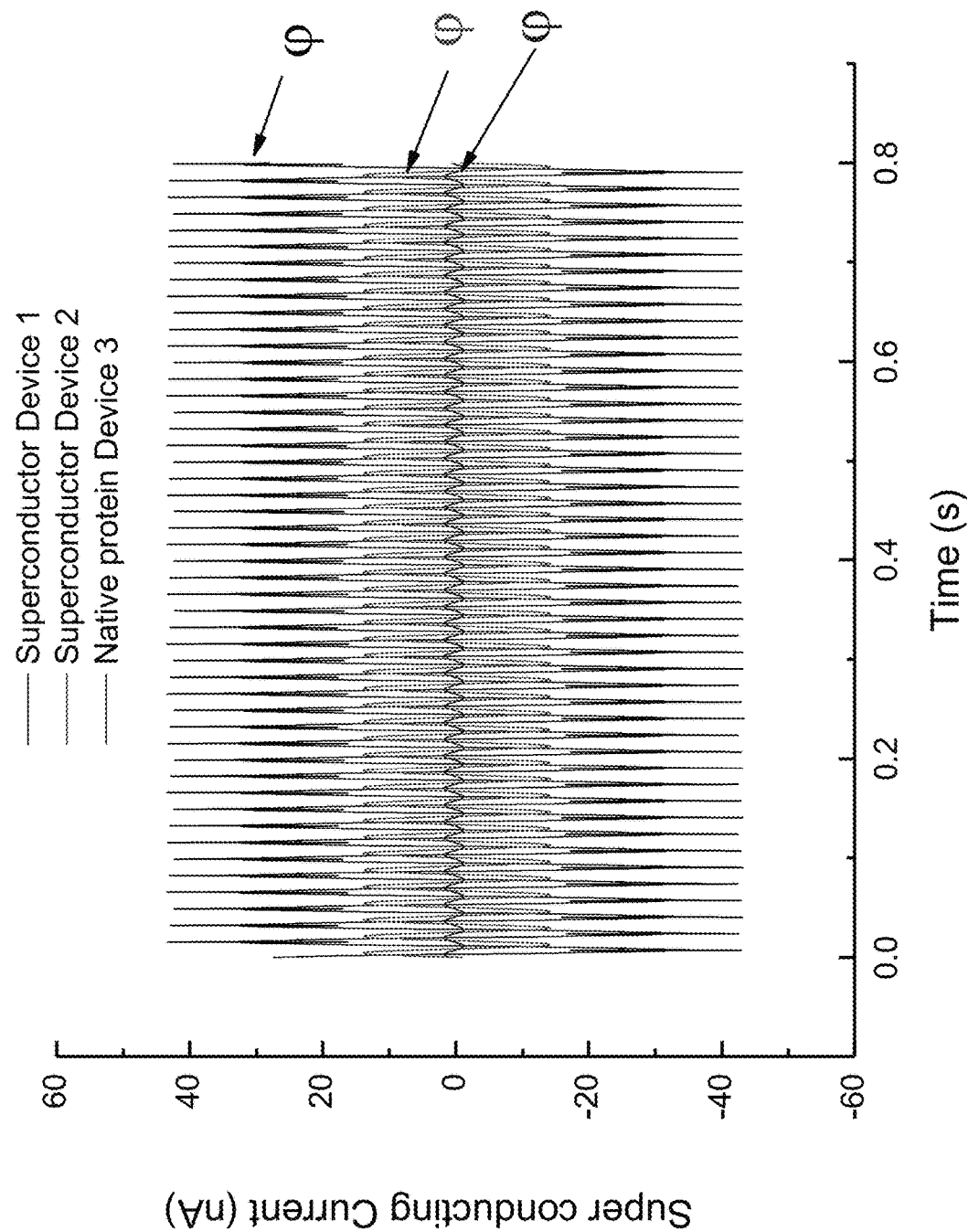

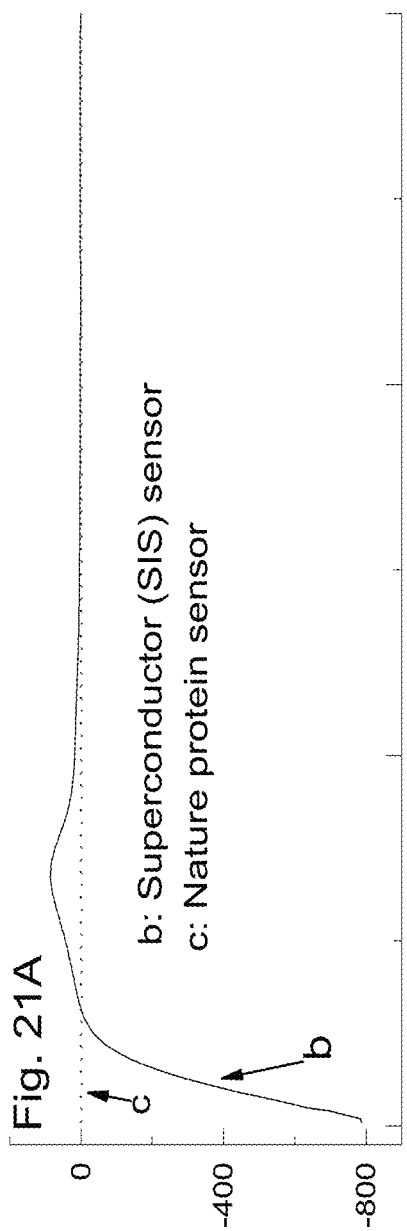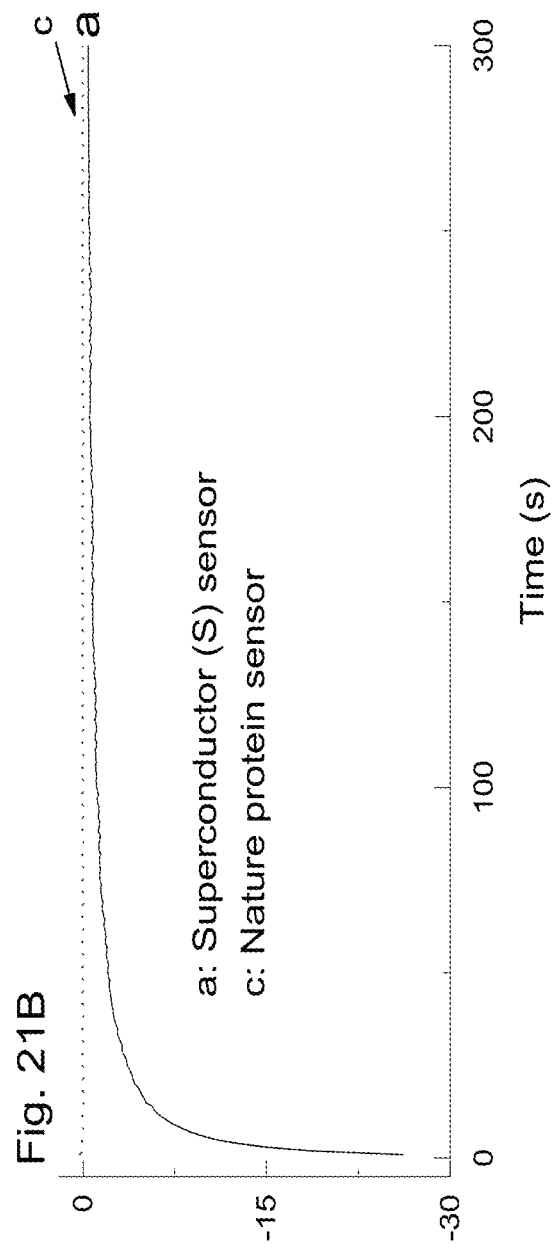

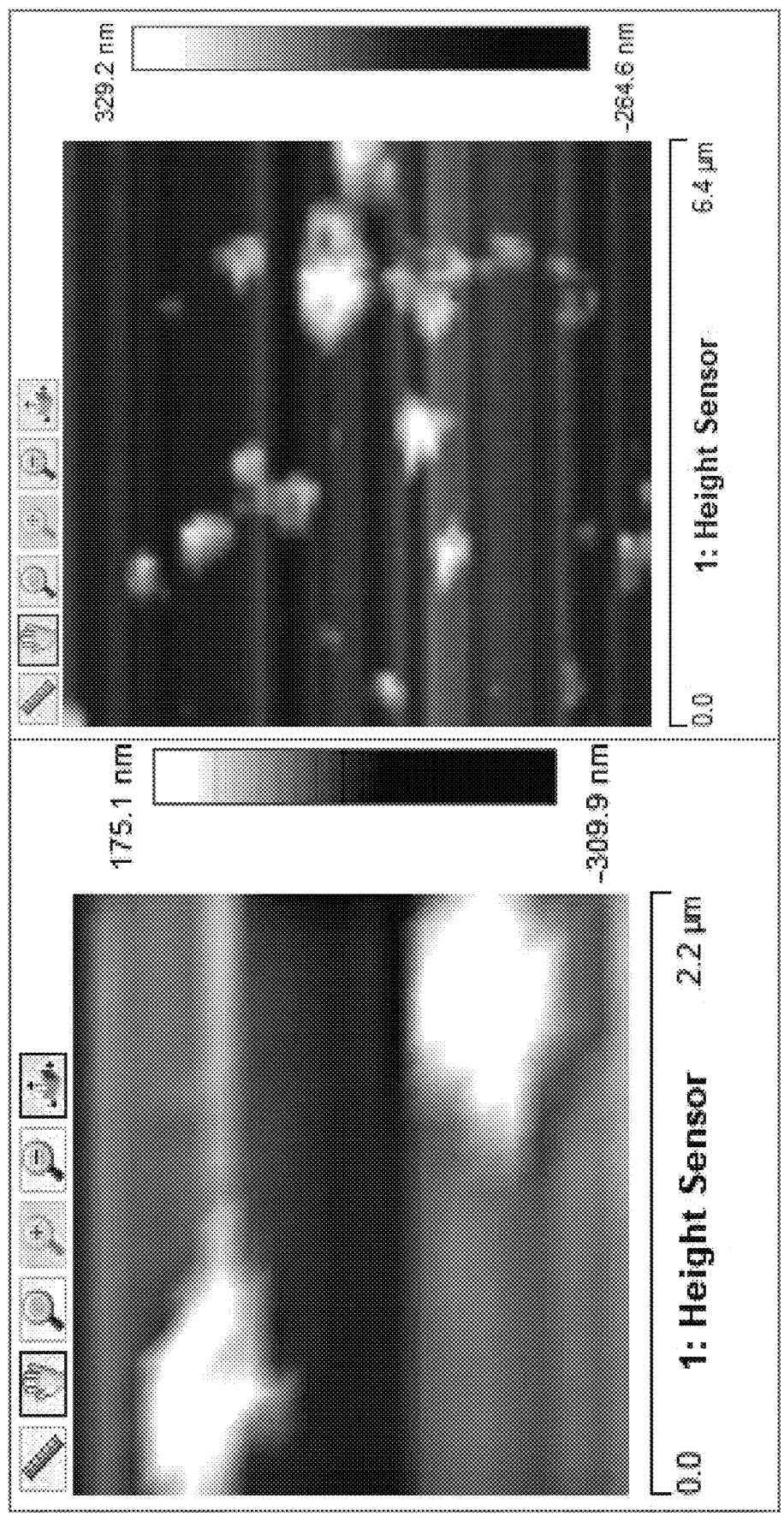

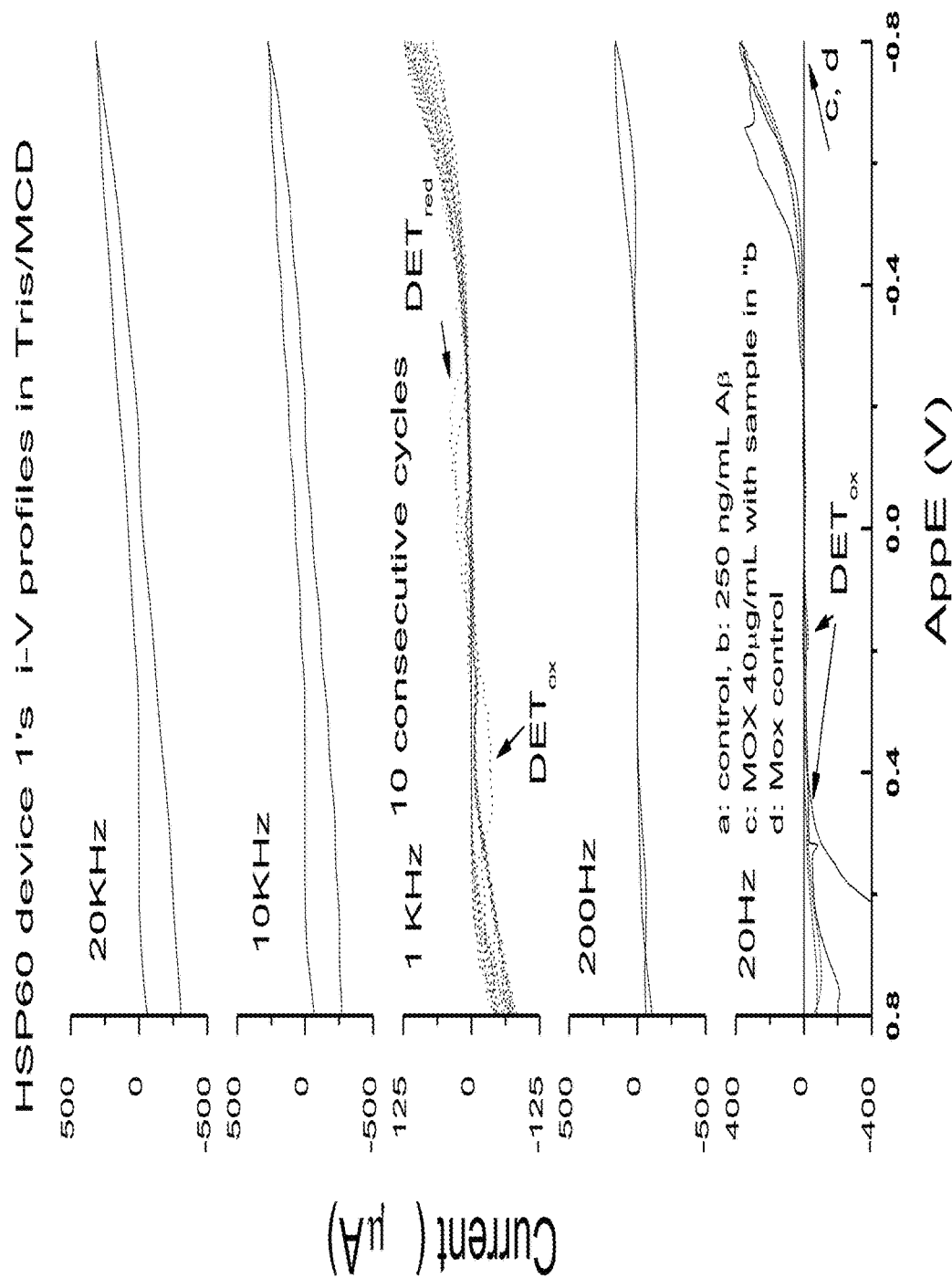

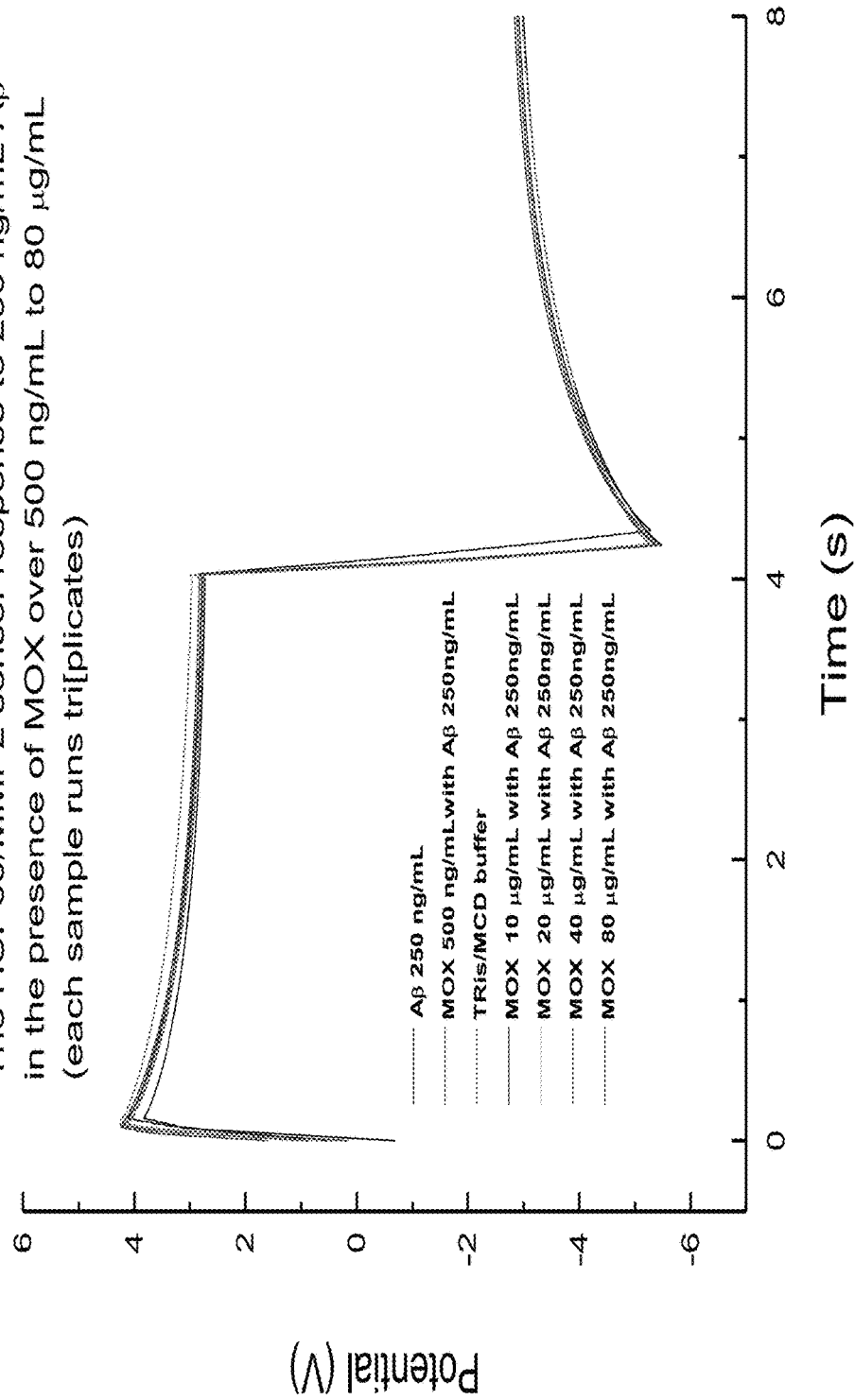

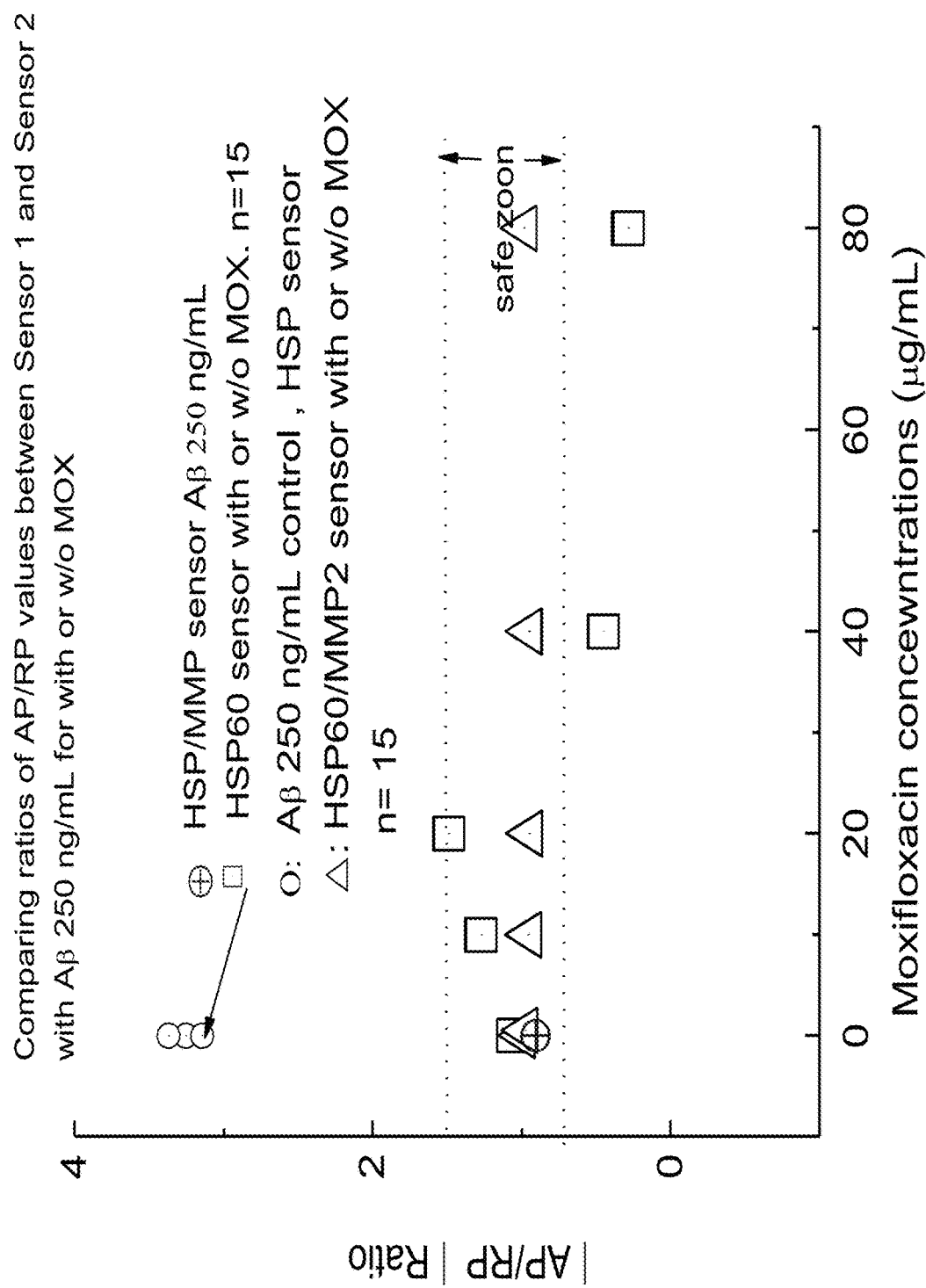

Fig. 38

Table 1. Comparing performances of two sensors by linear regression method of |Ap/Rp| vs. MOX concentration with 250 ng/mL Aβ

| Sensor | \|Ap/Rp\| Buffer only Mean (sd) | \|Ap/Rp\| 250 ng/mL Aβ Mean (sd) | Intercept | Slope | $S_{y/x}$ | r | n | Accuracy Related to buffer control | Pooled sd (%) From 0 to 80 μg/mL | p |
|---|---|---|---|---|---|---|---|---|---|---|
| 1[a] | 1.06(0.006) | 3.26(0.111) | 1.06 | 0.02 | 0.004 | 0.9998 | 9 | 87.9%[b] | 0.3% | < 0.0001 |
| 2[c] | 0.995(4.5e⁻⁴) | 0.90(0.004) | 0.97 | -9.4e⁻⁶ | 0.019 | -0.01 | 18 | 97.3% | 0.05% | < 0.955 |

NANOSTRUCTURED MODEL DEVICES OF MAKING AND APPLICATIONS IN MONITORING OF ENERGY LANDSCAPES OF TOXIC PROTEIN REFOLDING THERETO

CROSS-REFERENCE TO RELATED APPLICATIONS

This patent application entitled of Nanostructured Model Devices of Making and Applications in Monitoring of Energy Landscapes of Toxic Protein Refolding Thereto is a Continuation in Part of U.S. non-provisional patent application Ser. No. 16/865,340 in the title of Josephson Toroidal Vortex Quantum Superconductive/Memcapacitive and Superconductive/Memristive Devices of Making and Their Applications at Room Temperature Thereto that claims the benefit of U.S. Non Provisional patent application Ser. No. 16/865,340 filed on May 2, 2020. The entire disclosure of the prior patent application Ser. No. 16/865,340 is hereby incorporated by reference, as is set forth herein in its entirety.

FIELD OF THE INVENTION

The invention in the title of Josephson Toroidal Vortex Quantum Superconductive/Memcapacitive and Superconductive/Memristive Devices of Making and Their Applications at Room Temperature Thereto relates to the field of superconductor, in particular, to a device having both characteristics in superconductivity and memristive/memcapacitive/meminductive embedded with non-ferromagnetic switches functioning at room-temperature and its applications in sensing and energy storage.

The present invention entitled of Nanostructured Model Devices of Making and Applications in Monitoring of Energy Landscapes of Toxic Protein Refolding Thereto is a Continuation in Part of U.S. non-provisional patent application Ser. No. 16/865,340 in the title of Josephson Toroidal Vortex Quantum Superconductive/Memcapacitive and Superconductive/Memristive Devices of Making and Their Applications at Room Temperature Thereto that claims the benefit of U.S. Non Provisional patent application Ser. No. 16/865,340 filed on May 2, 2020. The entire disclosure of the prior patent application Ser. No. 16/865,340 is hereby incorporated by reference, as is set forth herein in its entirety. The invention related to the field of electrochemical sensors, in particular, to a device having both characteristics in memristor/memcapacitor acting as a dual function biosensor for detecting a biomarker that direct linked to Alzheimer's disease and other neurodegenerative diseases.

BACKGROUND OF THE INVENTION OF Ser. No. 16/865,340

Collagen is the most abundant protein in the human body. It is the primary structural component of the extracellular matrix (ECM) that is responsible for the physical maintenance of all cells [1]. The triple-helical structure of collagen assembles into insoluble collagen fibrils to strengthen the structural integrity of bones and tissues, therefore, preventing normal proteinase from engaging [1-2]. Collagen is a double-edged sword, not only actively paving the road for physiological normal cell and pathological abnormal cell adhesion, migration and intracellular communication, but also activating some receptors for either over-production or failure of matrix degradation caused by either bacterial collagenase or abnormal fibrosis from fibroblast cell, endothelial cell or epithelial cells; hence many diseases are associated with the malfunction of collagen [1-5]. A long history of traditional approach has been used for denaturing collagen as a substrate, to probe collagen degradation or to study matrix metalloproteinase (MMP) activity [6-7]. However, a clinically useful detection range at the low end for collagen-1 is difficult to accomplish due to the denaturing processing. A recent report revealed interstitial collagenase can cleave native collagen type 1 and 3, not the denatured protein, which is the major component of the fibrous plaque cap [8]. Hence, overcoming the traditional denaturing protein approach to an innovative approach is necessary. Based upon our prior experience using the biomimetic polarizable microtubule memristive/memcapacitive device to enable direct detection of MMP-2 with ag/mL level sensitivity under antibody-free, tracer-free, and reagent-free conditions [9-10], herein we propose to develop superconductive quantum devices with superlattice structure, through forming toroidal Josephson Junction (JJ) [11-12] that may be enabled directly detection of collagen-1 in the presence of a biomimetic MMP-2, compared with that of a control device with a native MMP-2.

The Josephson Junction (JJ) is a key element in the broader area of superconductivity devices [11]. At near zero Kelvin temperature, some materials become such perfect conductors that a zero-voltage superconducting current exists without energy dissipation when an external magnetic field was applied. The Josephson coupled-superconductor effect is inherent in any S-I-S tunnel junction if the two sides of barriers are sufficiently thin to allow the coupling energy from the cooper pair tunneling at the coherent wave state between the two superconductors to exceed thermal fluctuations [11-13]. Inspired by several reports and predictions [14-16], we thought the unique coherent wave state produced in the S-I-S module at a long circular JJ may be a key feature to help to accomplish the goal of this project, where we attempt to utilize a circular JJ to solve our biosensing problem. Inspired by another theoretical prediction of a $\pi$-phase difference on a topological-superconductor, (TSC)/normal metal (NM) can arise induced by Majorana spin-triplet paring, which exhibits a Josephson phase of 0 and $\pi$-junction in its ground state without any applied magnetic flux [15]. A Josephson vortex is a quantum vortex of supercurrents in a long circular junction, and the supercurrent loops create a magnetic flux which suppresses the Josephson supercurrent of the junction, making the junction a capacitor with energy periodic in 2e [13, 16].

Recent theoretical predictions of Josephson-based meminductive, memristive quantum superconducting devices have drawn attention [17-19] that the Josephson supercurrent behaves hysteretically, herein we hypothesized to develop a TSC/quantum memristor (QMR) or a TSC/quantum memcapacitor (QMC) device that is able to measure collagen in a biological fluid sample without denaturing the protein may be accomplishable. It is well known that superlattice membranes have been used as candidates for applications in superconductivity [20]. Our group intentionally fabricated the TSC/QMC (as Device 1) and the TSC/QMR devices (as Device 2) without embedding collagen, so we can see the superlattice structures, and evaluate the function of collagen when we applied it on the membranes; and when compared to a native MMP-2 protein device (Device 3), that may help our understanding of the role of collagen interaction with biomimetic MMP-2 and native MMP-2 at the toroidal Josephson junction vortex.

FOLLOWING IS THE BACKGROUND OF THE CIP INVENTION

Protein moonlighting is a phenomenon that proteins perform two or more unrelated functions that are directly impacting human health [1-5]. MMPs and HSPs were well-known moonlighting proteins. Originally MMPs is known for their localization at the extracellular matrix (ECM), and have the role of degrading ECM proteins [1-5], but accumulated literature reported MMPs have been found in every cell compartment, such as in cytoplasm, in cell nuclei, and in mitochondria playing roles in apoptosis, tumor invasion, genetic instability, and innate immunity functionalities [1-7]. HSPs/MMPs working as a team to influence our immune system have been reported based on their moonlighting capabilities and unique behaviors [1-7]. This moonlighting catastrophic event may cause vulnerable to cancer patients, diabetes, coronary artery disease patients, and Alzheimer's patients when an unusual viral attacked, like SARS-CoV 2 viral in the pandemic, that a report had shown 50% upregulated genes among the top 10 infected human genes are belong to HSP family in the Covid 19 cases [8]. β-Amyloid and hyperglycemia can activate MMP-2 in the mitochondrial cell causing MMP-2 concentration increase, and it decreases the Heat Shock Protein (HSP) 60's concentration, which leads to disturbing the mitochondrial gap membrane potential, causes mitochondria cell dysfunction and released cytochrome c to apoptosis immune cells, hence, protein MMP/HSP network moonlighting contributes to many diseases [1-10].

Fluoroquinolones, levofloxacin, and moxifloxacin (MOX) prove to be clinically beneficial as adjunct treatment therapeutic agents for the management of severe Covid 19 patients worldwide according to reports in the literature [11-14]. There is very few, if any, to study the links between the Moon-lighting protein network of HSP/MMP with the proven effective antibiotics, such as moxifloxacin interacting with Aβ because of the high percentage of the mortality rate of Covid 19 is elderly who had significant underline diseases of Alzheimer's and dementia. The initial goal of this research project is to develop an HSP60/MMP-2 model device for evaluation of the MOX effectiveness to impair HSP60's function and lead to recover the reversible membrane potential in the presence of impact from Aβ compared with an HSP control device. Our prior research reported an innate HSP60/MMP-2 network protein device with cross-linked polymers forming superconductive and memristive nanostructured toroidal-tower array self-assembled membrane (SAM), was able to direct ultra-sensitively sensing multiple biomarkers, such as glucose, pyruvate, acetyl CoA, and choline, under antibody-free, label-free and tracer-free conditions [15]. The evidence implied that the HSP/MMP device mimicked the moon-lighting protein HSP/MMP network's characteristics. Under this discovery, we attempted to put this system under testing of its biocommunication with moxifloxacin with or without the impact of Aβ. Following Sections, we explain the methods used for evaluation of the protein refolding landscape energy changes with or without MOX in the presence of Aβ under antibody-free, labeling-free, reagent-free, and tracer-free conditions.

SUMMARY OF INVENTION

It is an object of the invention to provide a new generation of Josephson toroidal vortex quantum superconductive/ memristive device comprising multiple-layer superlattices made by self-assembling cross-linked organometallic polymers that facility cooper pair electrons hopping through the superlattices between the long Josephson toroidal vortex junction causing the Friedel-oscillation that paves a road for room temperature quantum superconducting with a memristive memory behaving.

It is an object of the invention to provide a new generation of Josephson toroidal vortex quantum superconductive/ memristive device having arrays of curvature single-wall organic nanotube coordinating with transition metal in $d_\pi$ chelating.

It is an object of the invention to provide a new generation of Josephson toroidal vortex (JTV) quantum superconductive/memristive device facilitating long-range direct electron-relay between biomimetic CHAT . . . biomimetic MMP-2 . . . collagen-1 within the boundary of the JTV superlattice that the changing phases of the cooper pair waves may promote and store eternal magnetic flux energy as a function of collagen-1 concentration without applying an external magnetic field.

It is an object of the invention to provide a new generation of Josephson toroidal vortex (JTV) quantum superconductive/memristive device that possesses extremely high quantum conductance density per superlattice at zero-bias that produces super current leading to be exponentially proportional to collagen-1 concentrations.

It is an object of the invention to provide a new generation of Josephson toroidal vortex (JTV) quantum superconductive/memristive device having dual functioning as a sensing device and of an energy harvesting device.

It is an object of the invention to provide a new generation of Josephson toroidal vortex (JTV) quantum superconductive/memcapacitive device based solely on the driving force of fractional Josephson vertices that depend on the super-current loops created a magnetic flux in which the superconducting phase discontinuities, herein it does not need an external applied magnetic field to be functional.

It is an object of the invention to provide a new generation of Josephson toroidal vortex (JTV) quantum superconductive/memristive device comprising of innate protein cross-linked with organic conducting polymers that process superconductive/memristive zero-bias peaks in the presence of collagen-1 and the supper current intensity is inversely proportional to the collagen-1 concentration.

It is an object of the invention to provide a new generation of Josephson toroidal vortex (JTV) quantum superconductive/memristive device comprising of innate protein cross-linked with organic conducting polymers that can quantitatively detect collagen-1 without a denaturing protein process.

It is an object of the invention to provide a method effectively control the intensity of the Friedel-oscillation in the superlattice at the JTV boundaries in order to find its application in sub fg/mL protein sensing using a CA method.

It is an object of the invention to make the biomimetic MMP-2 quantum superconductor/memristor device having orders of magnitude higher super conductance and signal intensity than that of the protein MMP-2 superconductor/ memristor device in both innate and activated state, respectively.

Summary of Current CIP Invention

It is an object of the present invention to provide a new type of model device that is able to conduct real-time evaluation of the landscape energy change during the processing of protein folding with or without antibiotic under an influence of the biomarker beta-amyloid (Aβ) at an open circuit potential state under antibody-free, labeling-free, reagent-free, and tracer-free conditions.

It is an object of the present invention to provide a new type of model device that is able to reveal the i-V curves of the direct electron transfer peak of an analyte at oxidation or reduction states at different scan rates of the analyte to a wide range concentration.

It is an object of the present invention to discover a new type of fabrication technology with optimum compositions of polymers cross-linked with innate proteins, such as Heat Shock Protein (HSP) 60, forming a self-assembled membrane on the surface of gold sensor chip, that enables the device to sense protein refolding energy landscape change of a biomarker protein, such as beta-Amyloid (Aβ) in the presence of an antibiotic drug, such as moxifloxacin (MOX).

It is an object of the present invention to discover a new type of fabrication technology with optimum compositions of conductive organic polymers having multiple functioning groups cross-linked with multiple innate proteins, such as Heat Shock Protein (HSP) 60 and Matrix Metalloproteinase (MMP)-2 forming multiple-layer self-assembled membranes on the surface of gold sensor chip to mimic a "Moonlighting-protein Network" in order to search for a better inhibitor to impair Aβ refolding in the HSP cavity for the purpose of reduce elderly patients' vulnerability to the virus attack.

It is an object of the present invention to discover a new method for monitoring of the Reversible Membrane Potential (RMP) after using the antibiotic drug MOX.

BRIEF DESCRIPTION OF THE DRAWINGS

FIG. 6 refers to the 2D AFM image of the Device 1's superconducting membrane with the zinc atoms in white color; the Cooper pair electron cloud moves toward the same direction.

FIG. 7 depicts the 3D AFM image of the protein MMP-2 membrane with superlattice matrix of the Device 3. Zinc atoms are either along with the toroidal rings or on the top of the ring.

FIG. 9A and FIG. 9B depict the native MMP-2 Device 3's circular structures with zinc atoms with the tapping mode for detail shown the zinc atoms in the native MMP-2 protein membrane and in sensor mode, respectively in 10 μm×10 μm.

FIG. 14C depicts the i-V profiles of the innate Device 3 in the presence of various collagen-1 concentrations from 500 fg/mL to 25 ng/mL compared with the PBS control solution at 300 Hz scan rate. FIG. 14D depicts the i-V profiles of the activated Device 3 in the presence of various collagen-1 concentrations from 500 fg/mL to 25 ng/mL compared with the PBS control solution at 300 Hz. FIG. 14G depicts the detail view of the i-V curve profiles of the zero-bias peak with the vertical dotted line having the collagen-1 concentration effects on current for the activated Device 3 in human capillary blood samples based on FIG. 14E. FIG. 14H depicts the oscillation zero-voltage peaks of the activated Device 3 in PBS control solution at 1 Hz, 1 kHz, 10 kHz, respectively. FIG. 14I depicts the trends of the supercurrent of $DET_{red}$, $DET_{ox}$ vs. scan frequencies between activated Device 3 in PBS solution compared with the innate state over scan rate 1 Hz to 10 kHz.

FIG. 15C depicts the trend of the potential of $DET_{red}$ and $DET_{ox}$ peaks moves as a function of concentrations of collagen-1 over 0.5 pg/mL to 25 ng/mL of the innate Device 3 according to the FIG. 15C.

FIG. 16A depicts the innate Device 1 transforms superconductivity to memristive behavior in the spiked 0.5 pg/mL collagen-1 in NIST human serum at 300 Hz at the first scan cycle with both, superconducting current and hysteresis point located at zero-potential. The insert figure shows the hysteresis point at zero-potential, while located in the superconducting band. FIG. 16B depicts the second scan cycle; FIG. 16C depicts the third scan cycle; FIG. 16D depicts the fourth scan cycle; FIG. 16E depicts the fifth scan cycle and FIG. 16F depicts the control of NIST serum sample with pure memristive characteristics.

FIG. 17A depicts Device 1's voltage profiles over collagen level 0.5 pg/mL to 200 ng/mL at 0.25 Hz. FIG. 17B depicts the calibration curve. Samples run triplicates.

FIG. 19A depicts the trend of the Resting potential curve vs. spiked collagen-1 concentrations in PBS solutions for innate Device 1. FIG. 19B depicts the trend of the Action potential curve vs. spiked collagen-1 concentrations and FIG. 19C depicts the energy density curve vs. collagen-1 concentrations. All samples run triplicates.

FIG. 20 depicts the AC current oscillating with a time span in 0.4 s for 4000 data points per step measurement compared among activated Device 1, Device 2 and innate Device 3 with 13 ms, 18 ms and 12 ms per peak spent for oscillation at zero potential in every step in PBS solution using the CA method.

FIG. 21A depicts DC curves vs. time under zero potential compared with Device 2 and the innate Device 3 using the DC potential amperometric method. FIG. 21B depicts DC curves vs. time under zero potential compared with Device 1 and the innate Device 3 using the DC potential amperometric method.

FIG. 31A depicts Sensor 1's i-V curves of controls over different scan rates. At 20 Hz, compared curves of MOX affecting Aft

FIG. 36B depicts Sensor 2's profiles with MOX from 0.5 to 80 µg/mL (5 levels).

FIG. 37 depicts the comparison between Sensor 1 and Sensor 2 for the plots of AP/RP ratio vs. MOX concentration in the presence of 250 ng/mL Aβ over MOX from 0 to 80 µg/mL.

FIG. 38 is the content of Table 1, it compares performances of two sensors by linear regression method of |Ap/Rp| vs. MOX concentration with 250 ng/mL Aβ.

FOLLOWING IS THE DETAILED
DESCRIPTION OF THE INVENTION
APPLICATION U.S. Ser. No. 16/683,340

Example 1

Fabrication of the Nanobiomimetic Organometallic Superconductive/Memristive and Superconductive/Memcapacitive/meminductive Devices Having Superlattice Toroidal Structures Device 1's membrane was freshly prepared by self-assembling method with compositions of triacetyl-β-cyclodextrin (TCD), polyethylene glycol diglycidyl ether (PEG), poly(4-vinylpyridine) (PVP), bis-imidazole substituted dimethyl-β-cyclodextrin (bM-β-DMCD), cysteine and embedded zinc chloride on gold chips with appropriate proportions at 37° C. for 96 hours. Device 2 was made by two steps: first, deposits a polymer mixture of TCD/PEG/PVP/β-CD copolymer, that mimics choline acetyltransferase (CHAT) on the 50 nm gold chip with appropriate proportions forming nano-island layer 1 and the AFM image confirmed the nano-islands structure; the second step was to deposit another freshly prepared similar polymer mixture as Device 1 does, except without the L-cysteine, on the top of the nano-island membrane. The second layer of the polymer mixtures of bM-β-DMCD//PEG/PVP/TCD/$ZnCl_2$ has a volume ratio range from 6:1 to 10:1 for bM-β-DMCD to each of other component, except to $ZnCl_2$, 4:1 with the CD's concentration in 10-fold higher than that of PEG or PVP, respectively. At the first 2 hours, the temperature kept at 80° C., after that the temperature was reduced to 37° C. for 96 hours. For other procedures, reference was on the literature [9]. Procedures of synthesis and characterization of mM-β-DMCD and bM-β-DMCD were based on the published literature [21]. Denaturing procedure of Device 1's membrane was conducted at 80° C. for 5 minutes, then washing and the dry procedure was followed.

Example 2

Fabrication of the Native MMP-2 Protein Superconductive/Memristive Devices with Superlattice Toroidal Structures The reference device, Device 3, was fabricated by the polymer mixture of TCD/PVP/PEG and the native MMP-2 protein in appropriate proportions at 37° C. for 96 hours on a 50 nm gold chip. MMP-2 enzyme was purchased from Ana Spec (Freemont, CA).

Example 3

Figure 1:
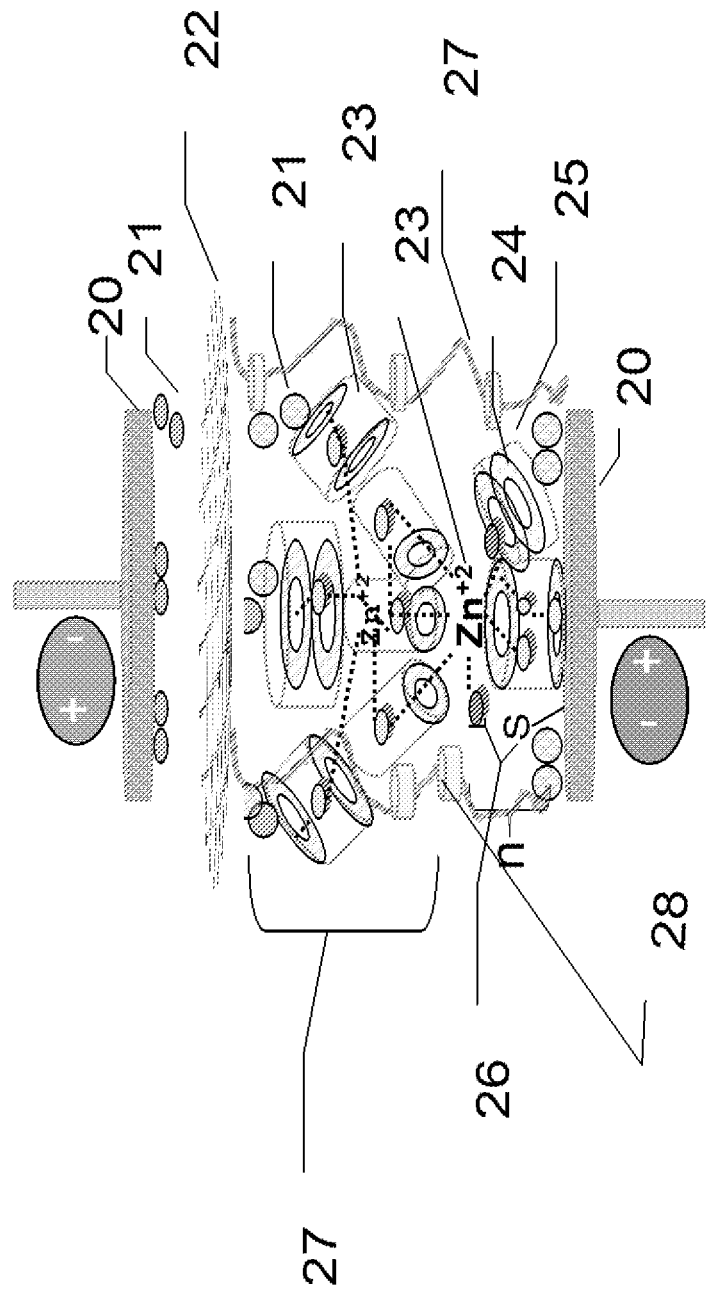
FIG. 1 depicts the schematic components in the engineering design of the superconductive/memcapacitive/memristive device 1 in a front-face view. "20" is the gold electrode with 50 nm thickness adherences on a flexible plastic plate substrate with a switchable connection; "21" is the Cooper pair electrons, "22" is the collagen-1 matrix, "23" refers to the zinc ions formed coordination complex with ligands of mono-imidazole modified-β-dimethylcyclodextrin (mM-β-DMCD), in short as MCD, that are in two schemes: (1) the zinc ion chelated with four imidazole groups in cavities of four MCDs and also with one COO⁻ group of TCD; another scheme is the zinc ions chelate with three imidazole groups in three MCDs and the fourth ligand is with either the COO⁻ group from the TCD as "24" or with the COO⁻ group from N-acetyl-L-cysteine referred to as "25", and the fifth ligand is with the imidazole group in bM-β-DMCD; "26" refers to the repeating processing of n units; "27" refers to the PEG . . . PVP forming biomimetic proteins' N-terminal vertical architecture of the toroidal memristive structure; "28" refers to the PEG . . . TCD chain forming biomimetic proteins' C-terminal vertical architecture of the toroidal; "29" refers to the repeated units. Notice there is an air gap space around zinc ions.

Models Used to Engineering the Superconductive/Memcapacitive or Superconductive/Memristive Devices FIG. 1 depicts the schematic components in the engineering design of the superconductive/memcapacitive/memristive device 1 in a front-face view. "20" is the gold electrode with 50 nm thickness adherences on a flexible plastic plate substrate with a switchable connection; "21" is the cooper pair electrons, "22" is the collagen-1 matrix, "23" refers to the zinc-imidazole of the mono imidazole modified-β-dimethylcyclodextrin (mM-β-DMCD), in short as MCD, that it coordinates in two schemes: (1) zinc ion chelated with four imidazole groups in cavities of four MCDs and also with one $COO^-$ group of TCD; another scheme is the zinc ions chelating with three imidazole groups in three MCDs and the fourth ligand is with either the $COO^-$ group from the TCD as "24" or with the $COO^-$ group from N-acetyl-L-cysteine referred to as "25", and the fifth ligand is with the imidazole group in bM-β-DMCD; "26" refers to the repeating processing of n units; "27" refers to the PEG . . . PVP forming biomimetic proteins' N-terminal vertical architecture of the toroidal memristive structure; "28" refers to the PEG . . . TCD chain forming biomimetic proteins' C-terminal vertical architecture of the toroidal; "29" refers to the repeated units. Notice there is an air gap space around zinc ions.

Figure 2:
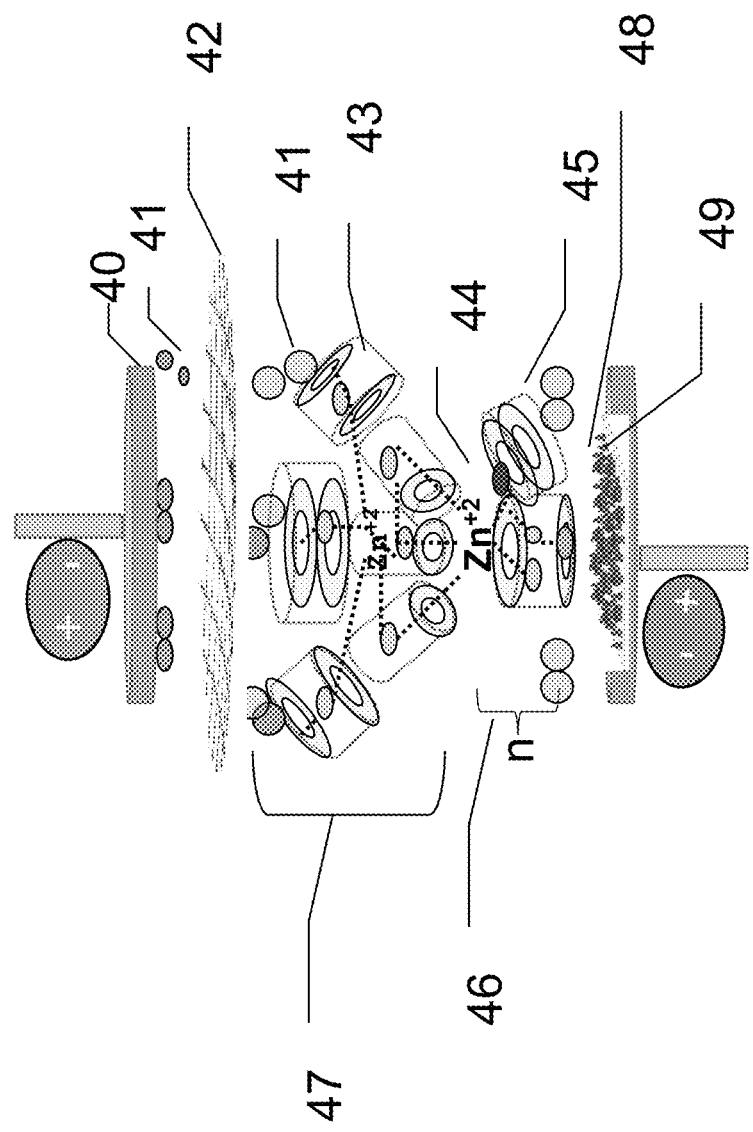
FIG. 2 depicts the schematic components in the engineering design of the superconductive/memristive/meminductive (SMRMI) device 2 in a side view. "40" is the gold electrode with 50 nm thickness adherences on a flexible plastic plate substrate with a switchable connection; "41" is the Cooper pair electrons, "42" is the collagen-1 matrix as an insulator, "43" refers to the zinc-imidazole of the MCD coordination complex: zinc ion chelated with four imidazole groups in cavities of four MCDs, and also chelates with the COO⁻ group of TCD; another zinc ion chelates with three imidazole groups in three MCDs, and with one COO⁻ group of TCD as "44", and one ligand with imidazole group in bM-β-DMCD as "48"; "45" refers to the repeating processing of "n" units; "46" refers to the PEG . . . PVP forming biomimetic proteins' N-terminal vertical architecture of the toroidal memristive structure; "47" refers to the PEG . . . TCD chain forming biomimetic proteins' C-terminal vertical architecture of the toroidal; "48" refers to the repeated units. Notice there is an air gap around zinc ions. "49" refers to the repeated units. "50" refers to the nanoislands structure membrane on 50 nm thickness gold electrode on a plastic substrate with a switchable gold electronic connect lead; the nano-island membrane comprises of TCD . . . PEG . . . PVP . . . β-CD copolymer, that mimics choline acetyltransferase (CHAT).

FIG. 2 depicts the schematic components in the engineering design of the superconductive/memristive/meminductive (SMRMI) device 2 in a side view. "40" is the gold electrode with 50 nm thickness adherences on a flexible plastic plate substrate with a switchable connection; "41" is the Cooper pair electrons, "42" is the collagen-1 matrix as an insulator, "43" refers to the zinc-imidazole of the MCD coordination complex: zinc ion chelated with four imidazole groups in cavities of four MCDs, and also chelates with the $COO^-$ group of TCD; another zinc ion chelates with three imidazole groups in three MCDs, and with one $COO^-$ group of TCD as "44", and one ligand with imidazole group in bM-β-DMCD as "48"; "45" refers to the repeating processing of "n" units; "46" refers to the PEG . . . PVP forming biomimetic proteins' N-terminal vertical architecture of the toroidal memristive structure; "47" refers to the PEG . . . TCD chain forming biomimetic proteins' C-terminal vertical architecture of the toroidal; "48" refers to the repeated units. Notice there is an air gap around zinc ions. "49" refers to the repeated units. "50" refers to the nanoislands structure membrane on 50 nm thickness gold electrode on a plastic substrate with a switchable gold electronic connect lead; the nano-island membrane comprises of TCD . . . PEG . . . PVP . . . β-CD copolymer, that mimics choline acetyltransferase (CHAT).

Figure 3:
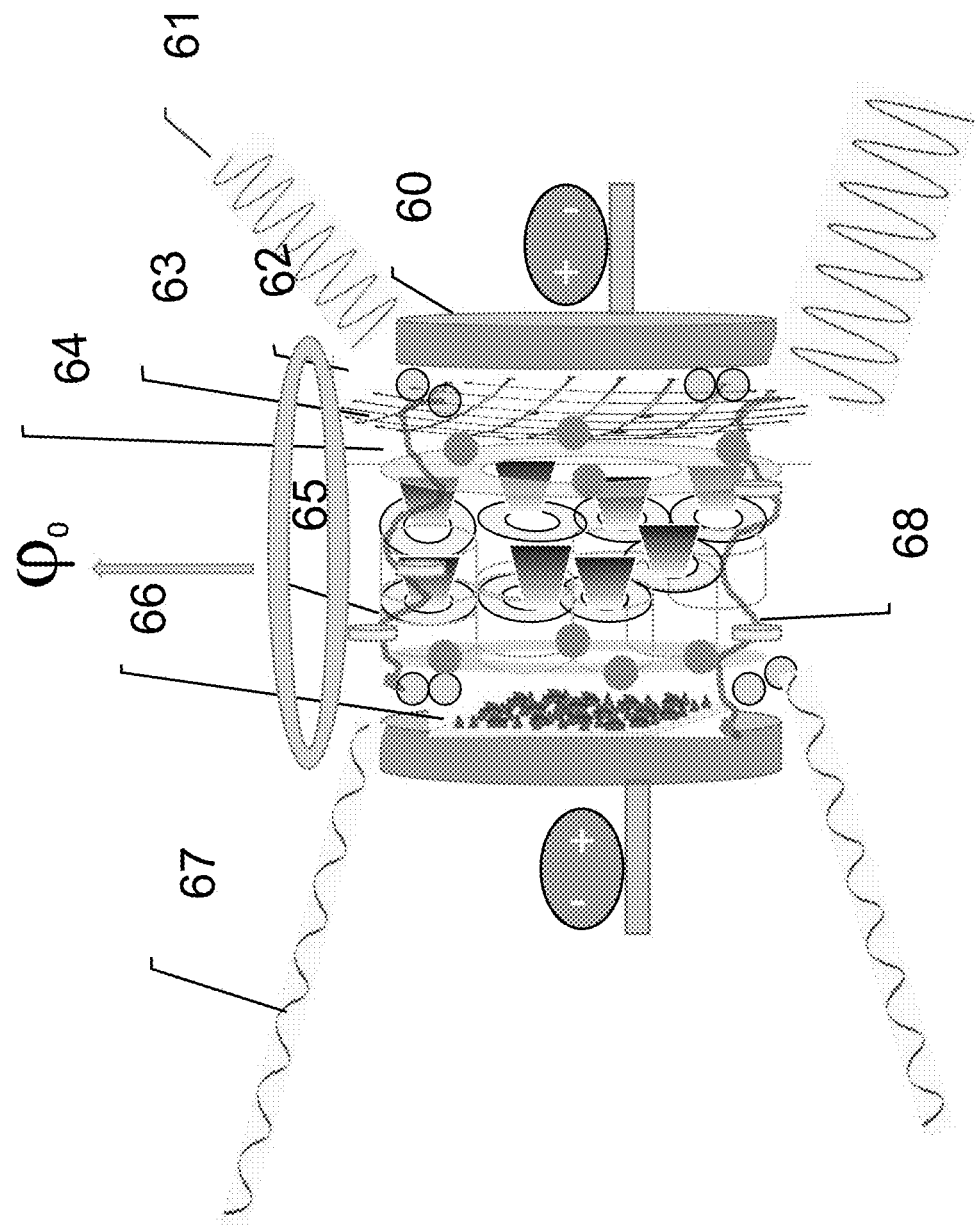
FIG. 3 depicts the art model for Device 2 in a side view of the Josephson Junction. "60" is the electrode; "61" is the amplified wave after the Cooper pair went through the multiple superconductor-Insulator-superconductor (SIS) layers at a higher frequency. "62" refers to the Cooper pair; "63" refers to the collagen-1 matrix; "64" refers to the circular current flow in a positive direction with the zinc atoms as the brown balls; "65" refers to the cyclodextrin array matrix alignment with each other produced the eternal superconducting current in the blue circle having induced a $\varphi_0$, single flux quantum, that a non-ferromagnetic field is produced; "66" is the nanoisland membrane on the gold electrode; "67" is the wave of cooper pair electrons after passing through the nanoisland membrane; Notice there is an air barrier between the membrane and the array of cyclodextrin matrix. "68" refers to the PEG . . . PVP's N-terminal chain.

FIG. 3 depicts the art model for Device 2 in a side view of the Josephson Junction. "60" is the electrode; "61" is the amplified wave after the Cooper pair went through the multiple superconductor-Insulator-superconductor (SIS) layers at a higher frequency. "62" refers to the Cooper pair; "63" refers to the collagen-1 matrix; "64" refers to the circular current flow in a positive direction with the zinc atoms as the brown balls; "65" refers to the cyclodextrin array matrix alignment with each other produced the eternal superconducting current in the blue circle having induced a $\varphi_0$, single flux quantum, that a non-ferromagnetic field is produced; "66" is the nanoisland membrane on the gold electrode; "67" is the wave of cooper pair electrons after passing through the nanoisland membrane; Notice there is an air barrier between the membrane and the array of cyclodextrin matrix. "68" refers to the PEG . . . PVP's N-terminal chain.

Figure 4:
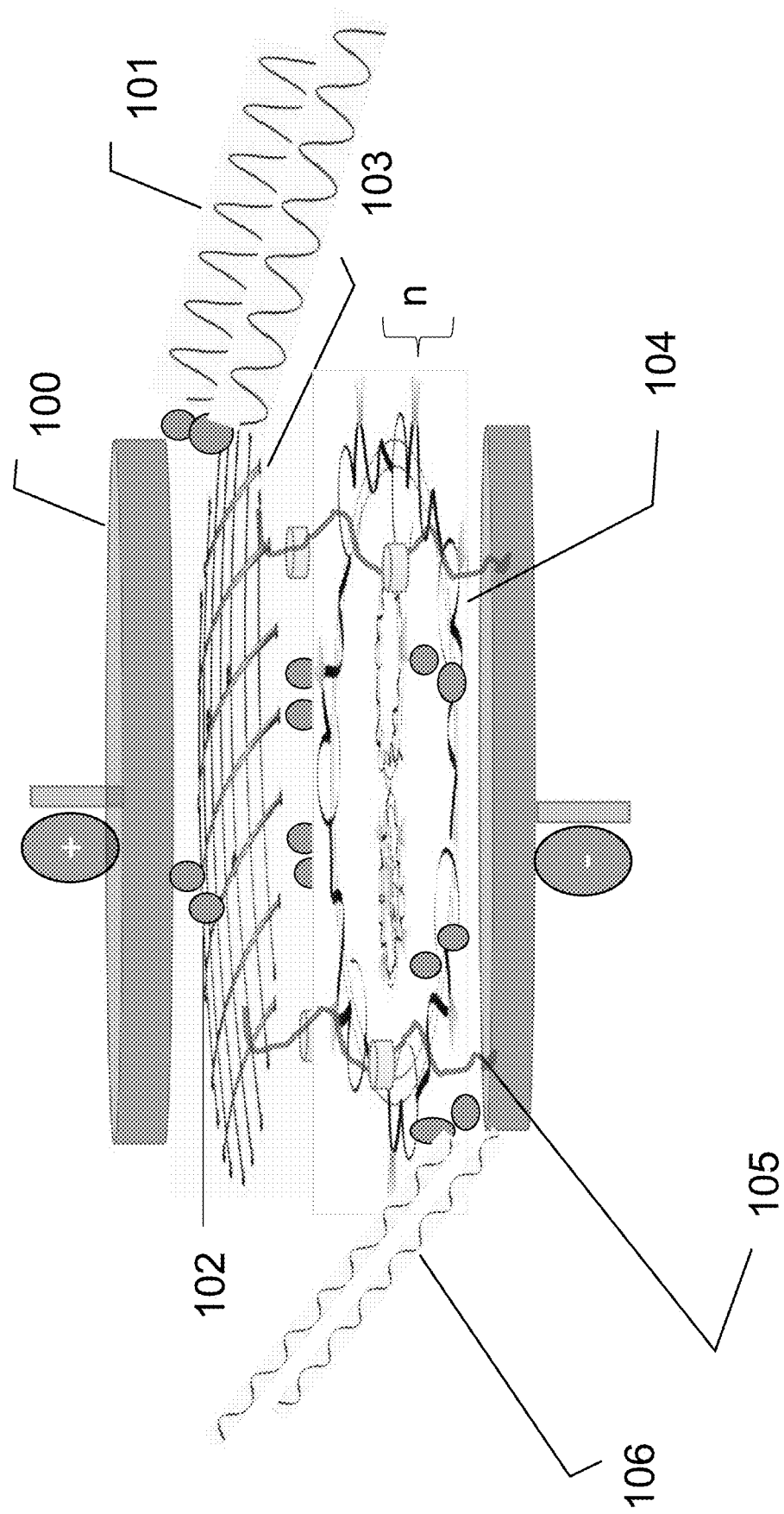
FIG. 4 depicts schematic components of the superconductive/memristive (SMR) activated MMP-2 protein device 3 in a side-view. "100" refers to the electrode; "101" refers to the amplified wave after the cooper pairs passed through the layers of superconductive-insulator-superconductive membranes; "102" is the cooper pair; "103" refers to the collagen-1 matrix; "104" refers to the superconducting membrane in horizontal orientation that comprised of the native MMP-2, TCD, PEG, and PVP. The blue diamonds on the rings refer to the migrated zinc atoms from the MMP-2. Inside have two small rings referring to multiple toroidal matrix arrays and it repeated for multiple times. Notice there is an air gap between the toroidal rings. Hence it comprised an SIS-SIS-SIN chain for amplification. "105" refers to the PEG . . . TCD vertical chain mimicking of C-terminal of a protein, and the right-hand side of the similar chain referrers to the PEG . . . PVP chain of mimicking N-terminal chain. "106" refers to the supercurrent wave from the Cooper pair after they passed through the superconducting layer. The two blue circles refer to the circler superconducting current that produced single flux quantum with the blue arrow is the induced electromagnetic field.

FIG. 4 depicts schematic components of the superconductive/memristive (SMR) activated MMP-2 protein device 3 in a side-view. "100" refers to the electrode; "101" refers to the amplified wave after the cooper pairs passed through the layers of superconductive-insulator-superconductive membranes; "102" is the cooper pair; "103" refers to the collagen-1 matrix; "104" refers to the superconducting membrane in horizontal orientation that comprised of the native MMP-2, TCD, PEG, and PVP. The blue diamonds on the rings refer to the migrated zinc atoms from the MMP-2. Inside have two small rings referring to multiple toroidal matrix arrays and it repeated for multiple times. Notice there is an air gap between the toroidal rings. Hence it comprised an SIS-SIS-SIN chain for amplification. "105" refers to the PEG . . . TCD vertical chain mimicking of C-terminal of a protein, and the right-hand side of the similar chain referrers to the PEG . . . PVP chain of mimicking N-terminal chain. "106" refers to the supercurrent wave from the Cooper pair after they passed through the superconducting layer. The two blue circles refer to the circler superconducting current that produced single flux quantum with the blue arrow is the induced electromagnetic field.

Figure 5:
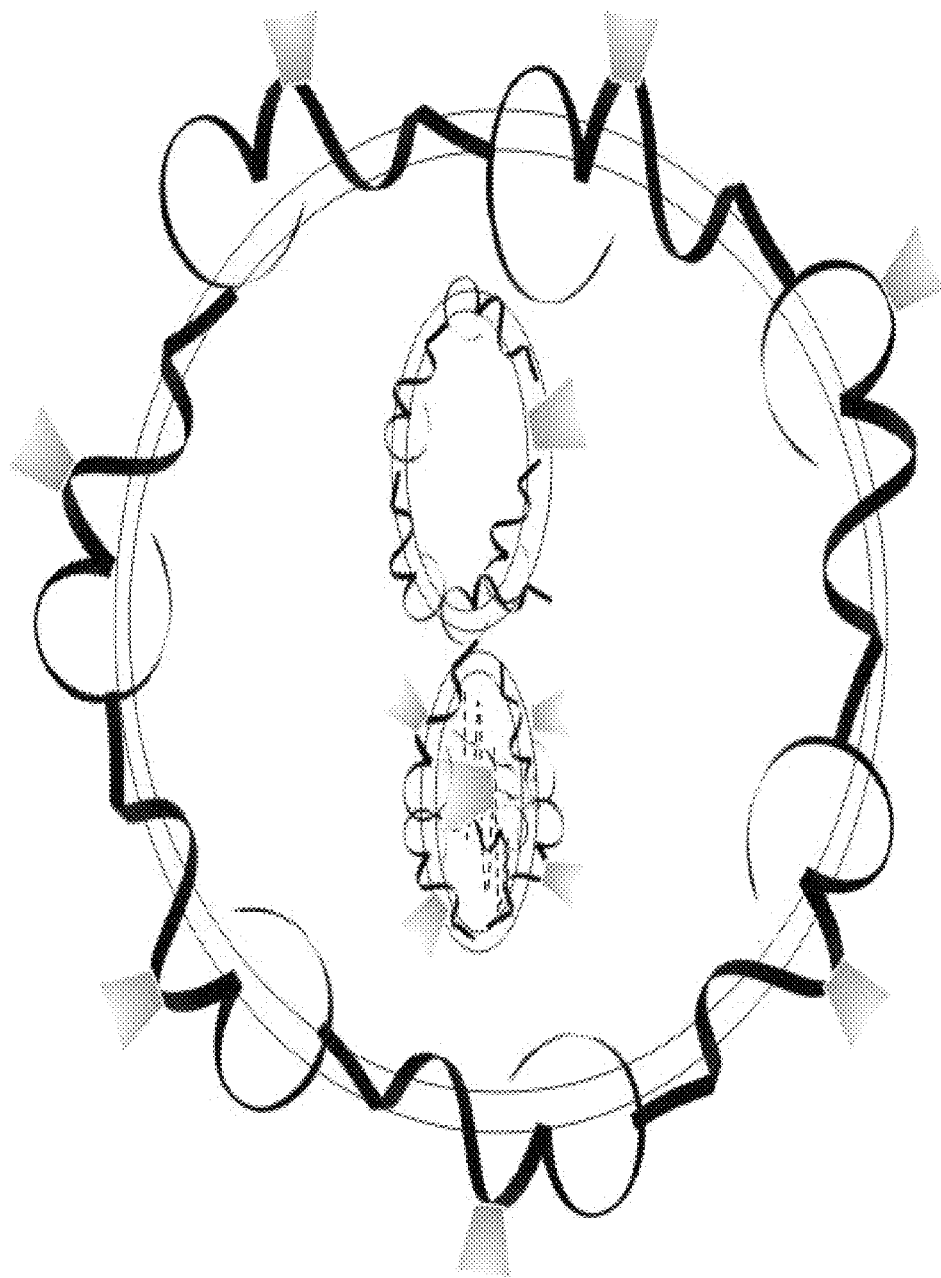
FIG. 5 refers to an enlarged top view of the superconducting membrane of activated protein MMP-2 Device 3.

FIG. 5 refers to an enlarged top view of the superconducting membrane of activated Device 3.

Example 4

Characterization of the Membranes

The morphology of the AU/SAM was characterized using an Atomic Force Microscope (AFM) (model Dimension Edge AFM, Bruker, MA). Data collected in Tapping Mode using silicon probes with 5-10 nm tip radius and ~300 kHz resonance frequency (Probe mode TESPA-V2, Bruker, MA). FIG. 6 refers to the 2D AFM image of the Device 1's superconducting membrane with the zinc atoms in white color; the Cooper pair electron cloud moves toward the same direction. FIG. 7 depicts the 3D AFM image of the protein MMP-2 membrane with superlattice matrix of the Device 3. Zinc atoms are either along with the toroidal rings or on the top of the ring.

Figure 8A:
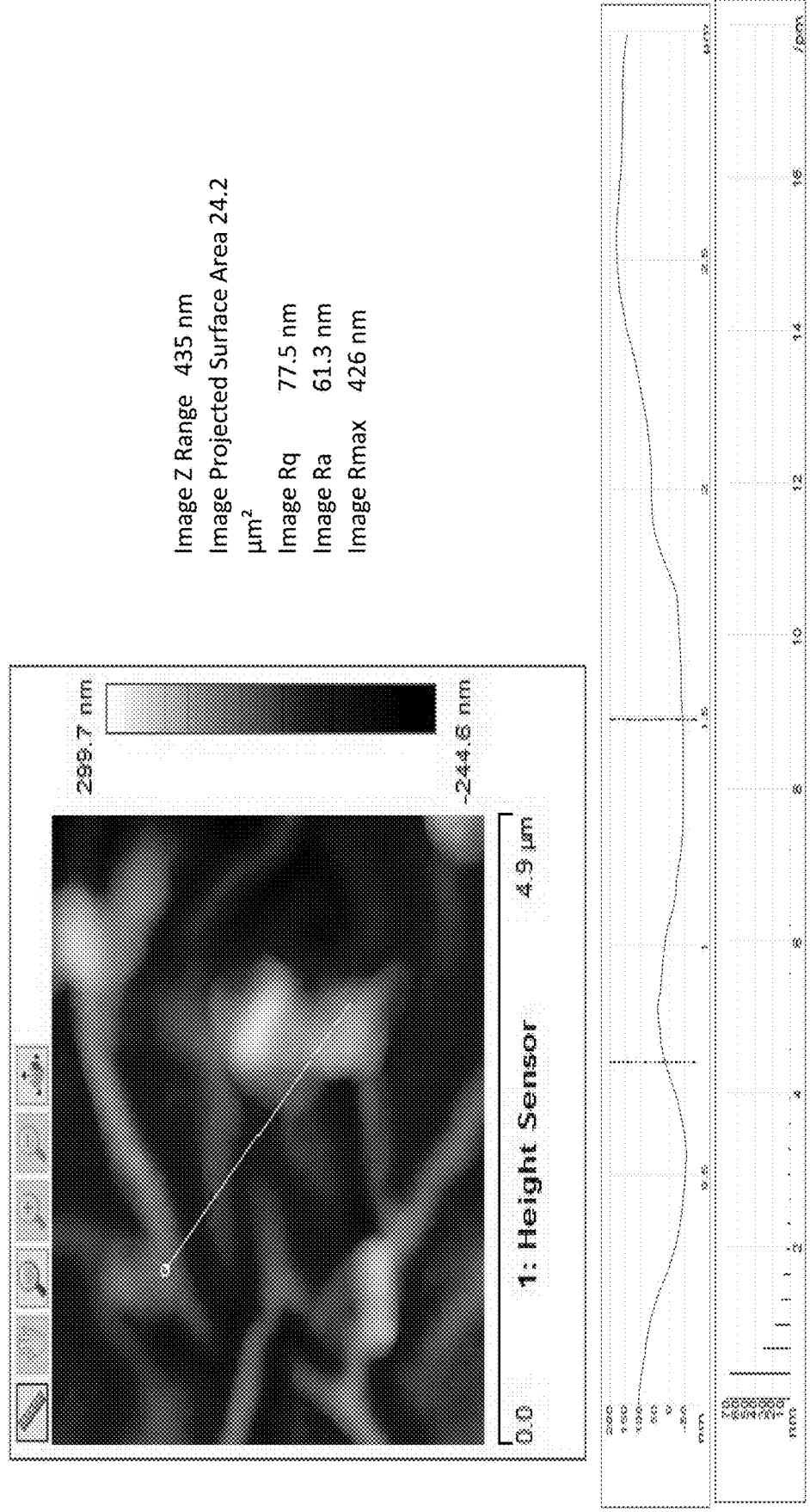
FIG. 8A depicts the 2D image in a bird-eye-view of the superlattice superconducting membrane with curvature nanotubes and the zinc atoms are served as the junction of Device 2 in a sensor mode with cross-section analysis in 5 μm×5 μm.
Figure 8C:
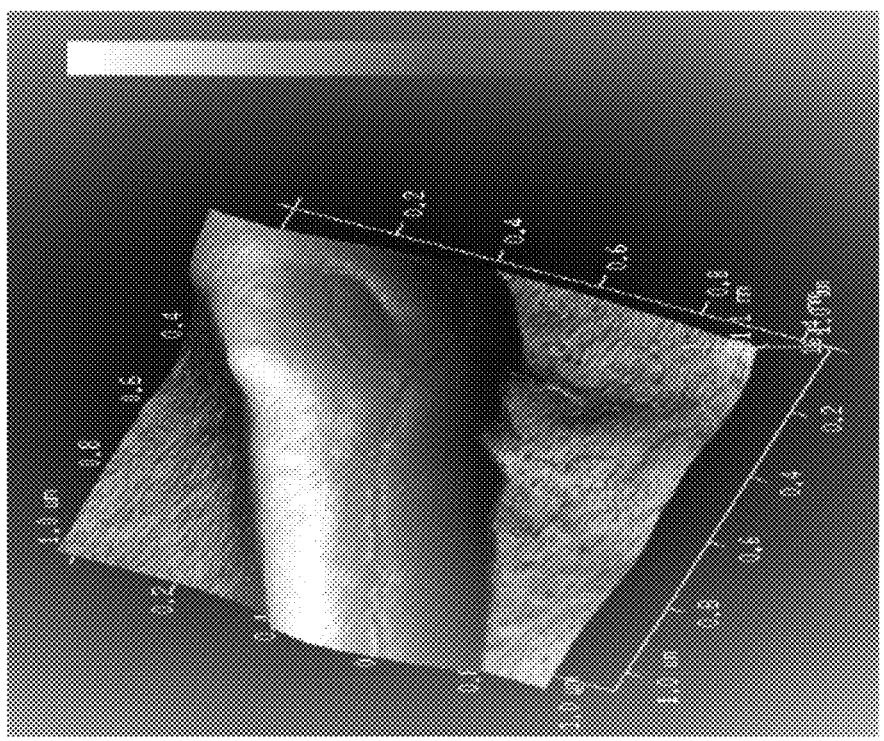
FIG. 8C is a 3D image of the curvature single-wall nanotube with zinc atom on top.
Figure 8B:
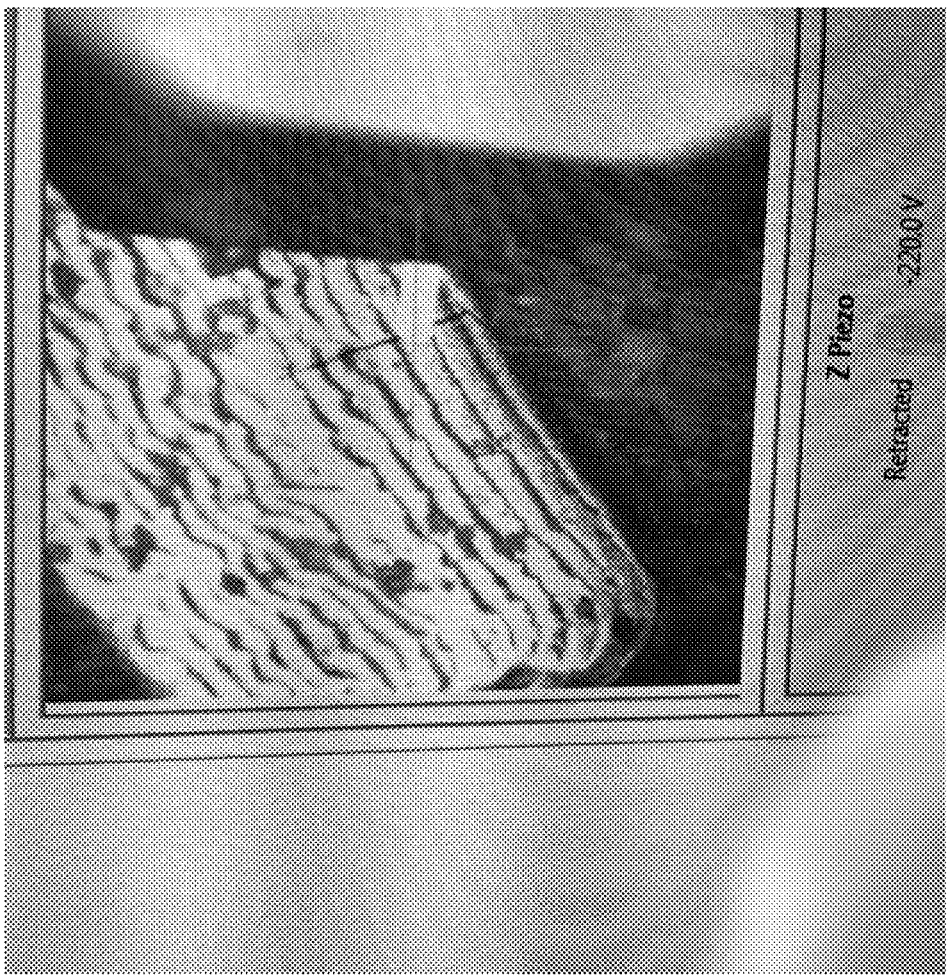
FIG. 8B is the photo image structure of the whole SAM superconductive multiple layers membrane on the screen during setting the probe before taken an AFM image.
Figure 8E:
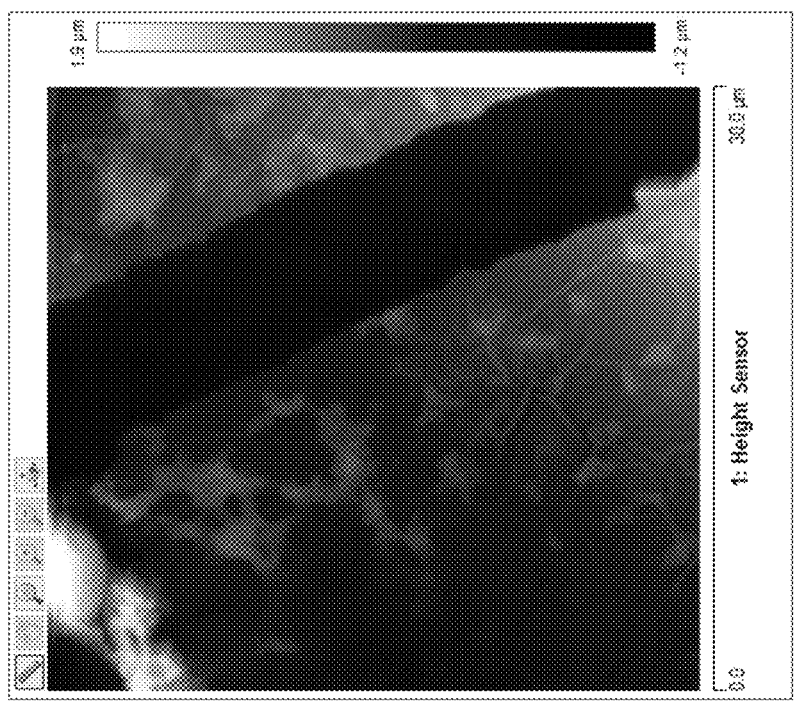
FIG. 8E depicts the deep carnal with superlattice on the top surface.
Figure 8D:
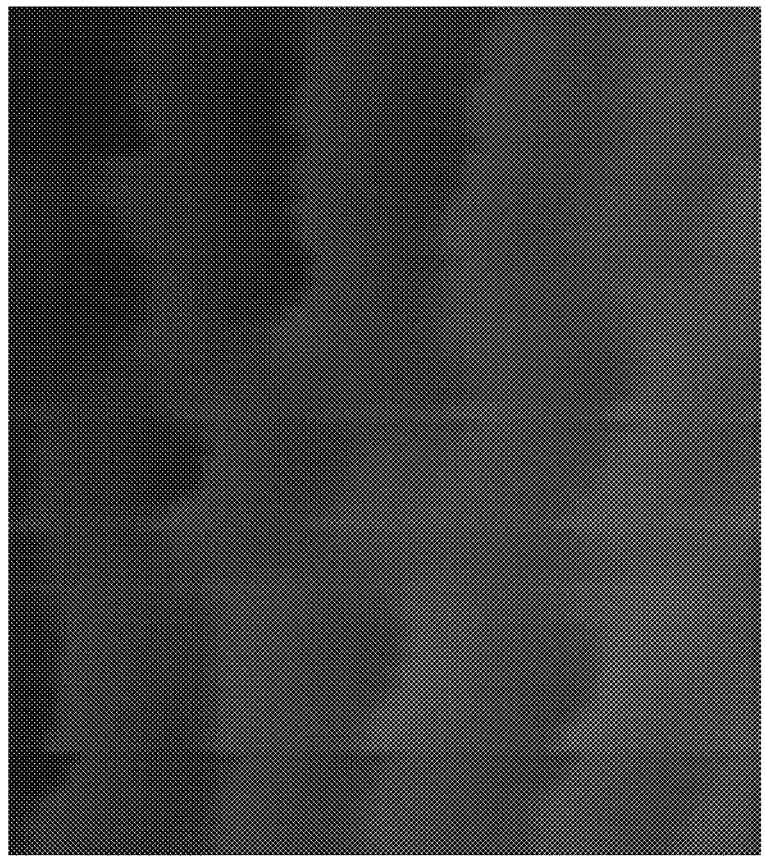
FIG. 8D depicts the 2D image of the multiple waves formed in the carnal in the membrane of Device 2 with the carnal location near the cross in FIG. 8B.
Figure 8G:
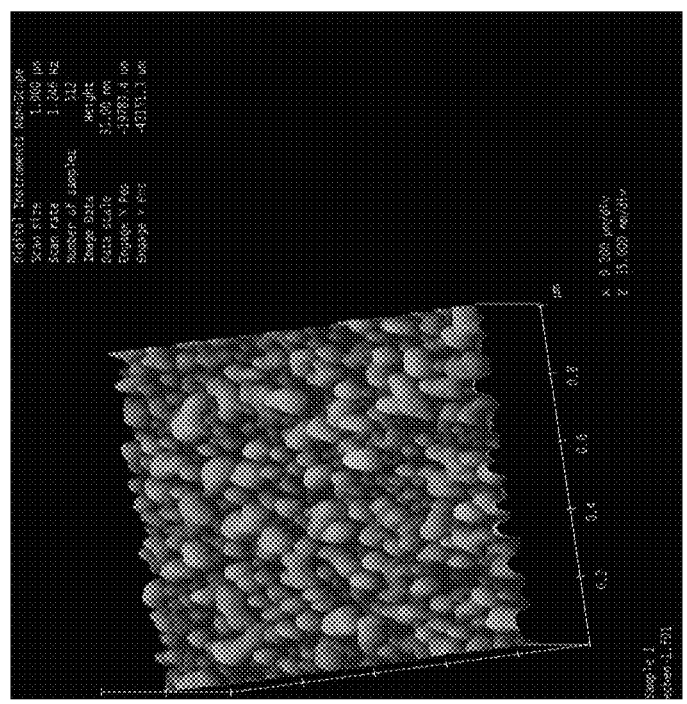
FIG. 8G depicts the first layer nano-island membrane on the gold chip, before the depositing other mixture solution.
Figure 8F:
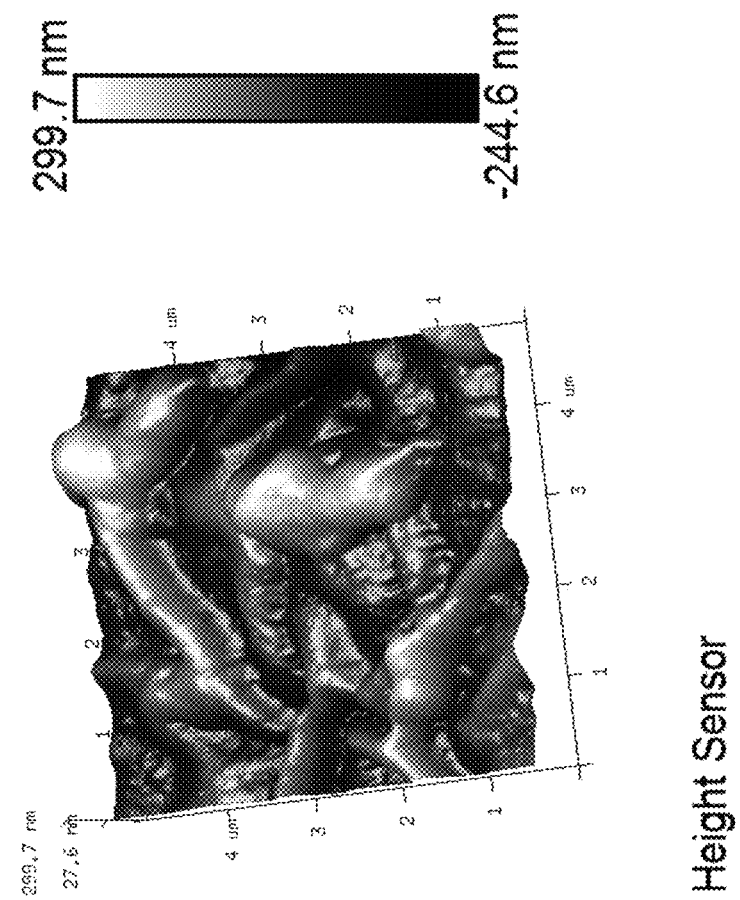
FIG. 8F depicts the 3D bird-view of the superlattice of Device 2.

FIG. 8A depicts the 2D superlattice layered structure with zinc atoms in sensor mode with cross-section analysis in 5×5 $\mu m^2$ with a diameter 200 nm and average length 2-3 $\mu m$ forming array lattice with an average area of the lattice occupying 21-25 $\mu m^2$, while zinc atoms on the edge or at the center of the lattice in that the device covered with $1.5 \times 10^5$ uniform oriented superlattice on top of the nanoisland layer. FIG. 8B depicts the Device 2's whole screenshot image before taken AFM. FIG. 8C depicts a 3D image of the curvature single-wall nanotube with zinc atoms on top; FIG. 8D depicts the 2D image of the multiple waves formed in the carnal in the membrane of Device 2 with the carnal location near the cross in FIG. 8B. FIG. 8E depicts the deep carnal with superlattice on the top surface. FIG. 8F depicts the 3D view of the superlattice of Device 2. FIG. 8G depicts the first nanoisland membrane on the gold chip, before depositing other mixture solution. FIG. 9A depicts the nature MMP-2 sensor's circular structures with zinc atoms. FIG. 9B depicts the tapping mode for detail shown the zinc atoms in nature MMP-2 protein membrane.

Example 5

Evaluation of the Friedel-oscillation in the Superlattice Toroidal Membranes

Evaluations of the Friedel-oscillation in the superlattice membrane was conducted based on the AFM images. Friedel-oscillation is a phenomenon for long-range indirect interactions between electrons on the surface [20]. The AFM images revealed the Friedel-oscillation are presented in FIG. 6 for Device 1. FIG. 7 is the 3D AFM image for the native protein Device 3 having superlattice structure and the zinc ions acted as the Josephson junction that have the Friedel-oscillation. FIG. 8A depicts the 2D image in a bird-eye-view of the superlattice superconducting membrane with curvature nanotubes and the zinc atoms are served as the junction of Device 2 in a sensor mode with cross-section analysis in 5 $\mu m \times 5$ $\mu m$; FIG. 8B is the photo image structure of the whole SAM superconductive multiple layers membrane on the screen during setting the probe before taken an AFM image. FIG. 8C is a 3D image of the curvature single-wall nanotube with zinc atom on top; FIG. 8D depicts the 2D image of the multiple waves formed in the carnal in the membrane of Device 2 with the carnal location near the cross in FIG. 8B. FIG. 8E depicts the deep carnal with superlattice on the top surface. FIG. 8F depicts the 3D bird-view of the superlattice of Device 2. FIG. 8G depicts the first layer nanoisland membrane on the gold chip, before the depositing other mixture solution.

FIGS. 9A and 9B depict the AFMs of the native MMP-2 Device 3's single-wall nanotubule toroidal structures with zinc atoms that are like diamonds on a ring or oscillation in the center in an amplitude mode or in a sensor mode, respectively. All rings have the same thickness in 90 nm in the circular nanotubes, and the diameters of the toroidal are in the range of 2.3-5.5 $\mu m$, and the height of the toroidal is from 0.5 to 0.9 $\mu m$. Zinc atom migration from the original cluster to other rings was observed.

Example 6

Figure 10A:
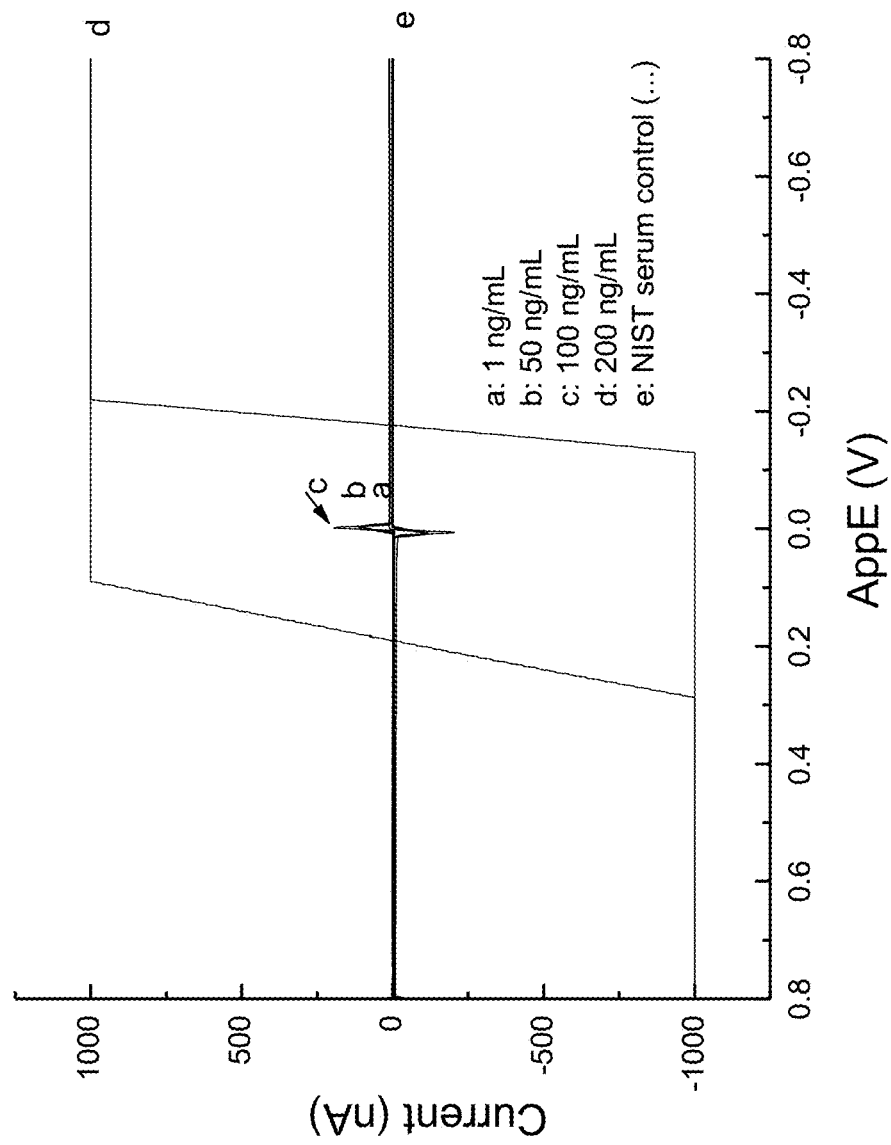
FIG. 10A depicts the i-V curves of super JJ current intensity in various collagen concentration at 300 Hz scan rate in NIST human serum with B=0.
Figure 10C:
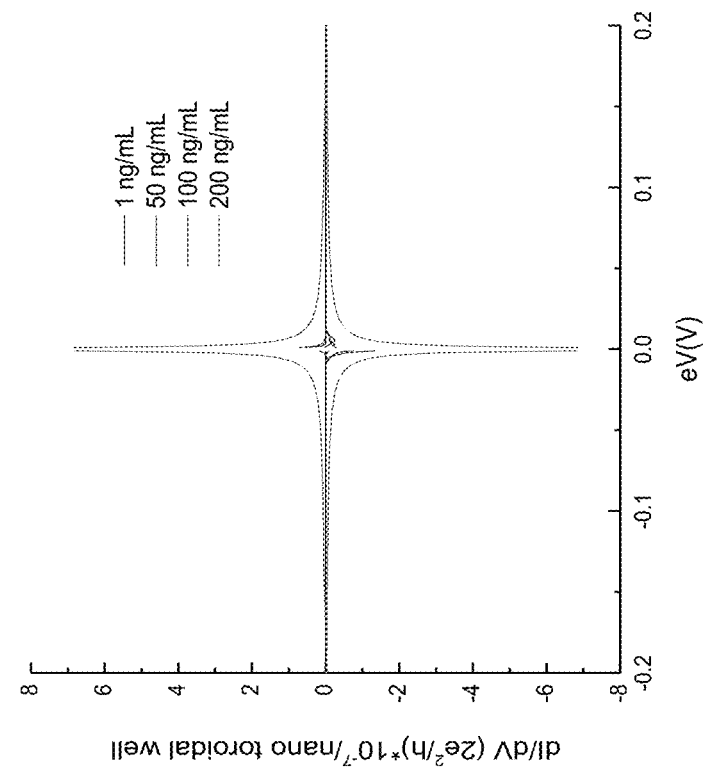
FIG. 10C depicts the curves in superconductive density of dI/dV ($2e^2/h$) per nano toroidal well vs. applied potential at zero-bias for Device 1.
Figure 10B:
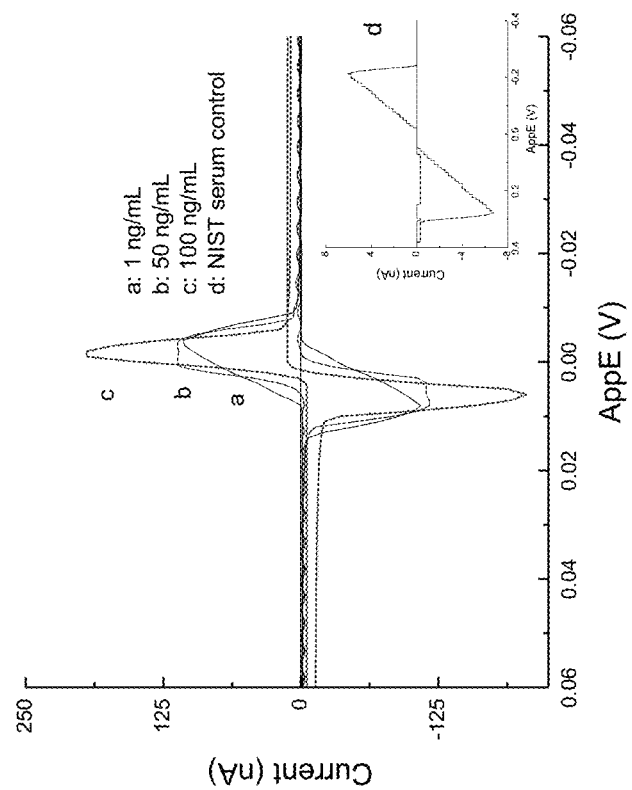
FIG. 10B depicts an enlarged view of the plots and the insert is the control of human serum.
Figure 11A:
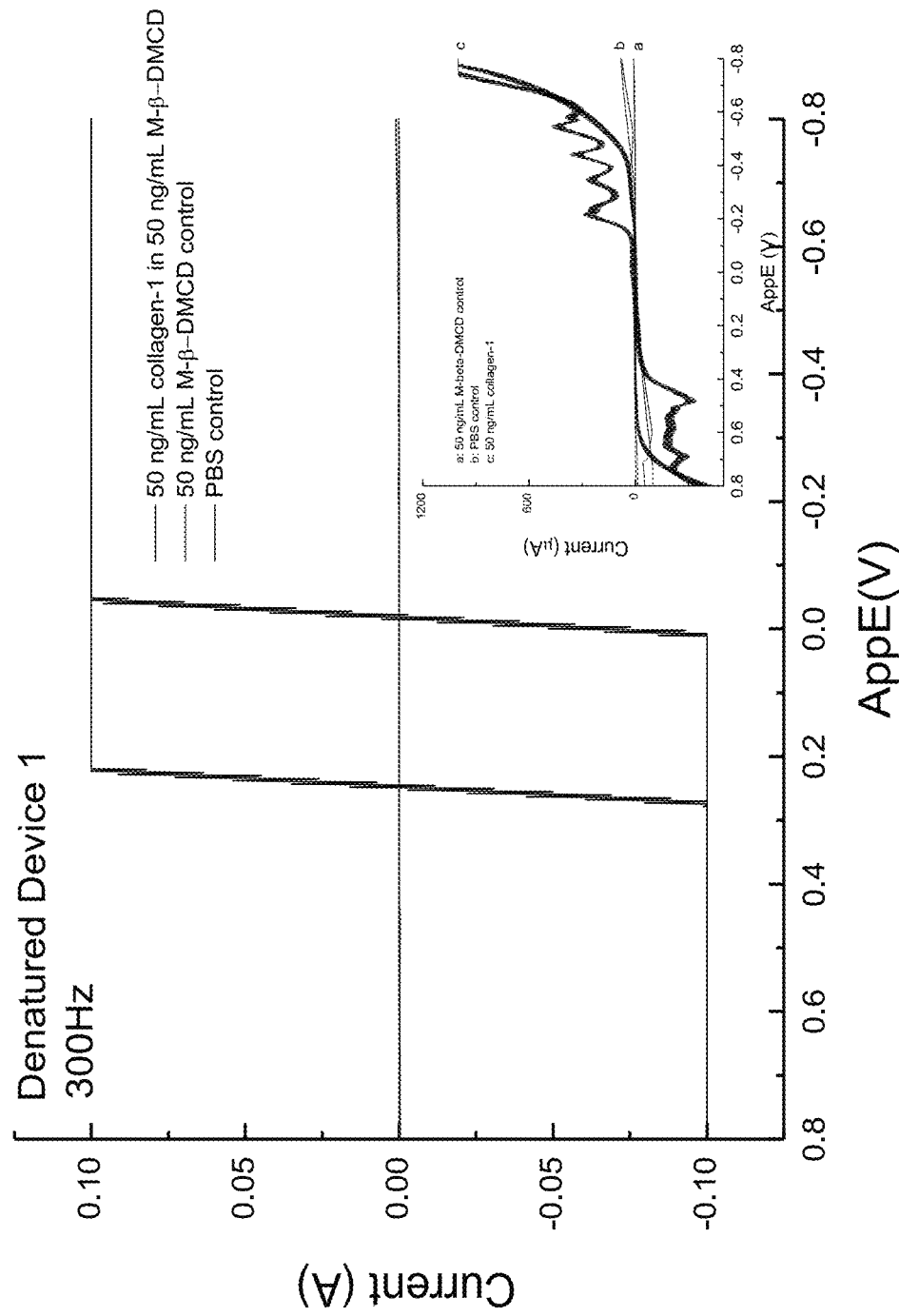
FIG. 11A depicts the denatured Device 1's i-V curve at spiked 50 ng/mL collagen-1 and 50 ng/mL MCD in the PBS solution. Insert is the controls.
Figure 11B:
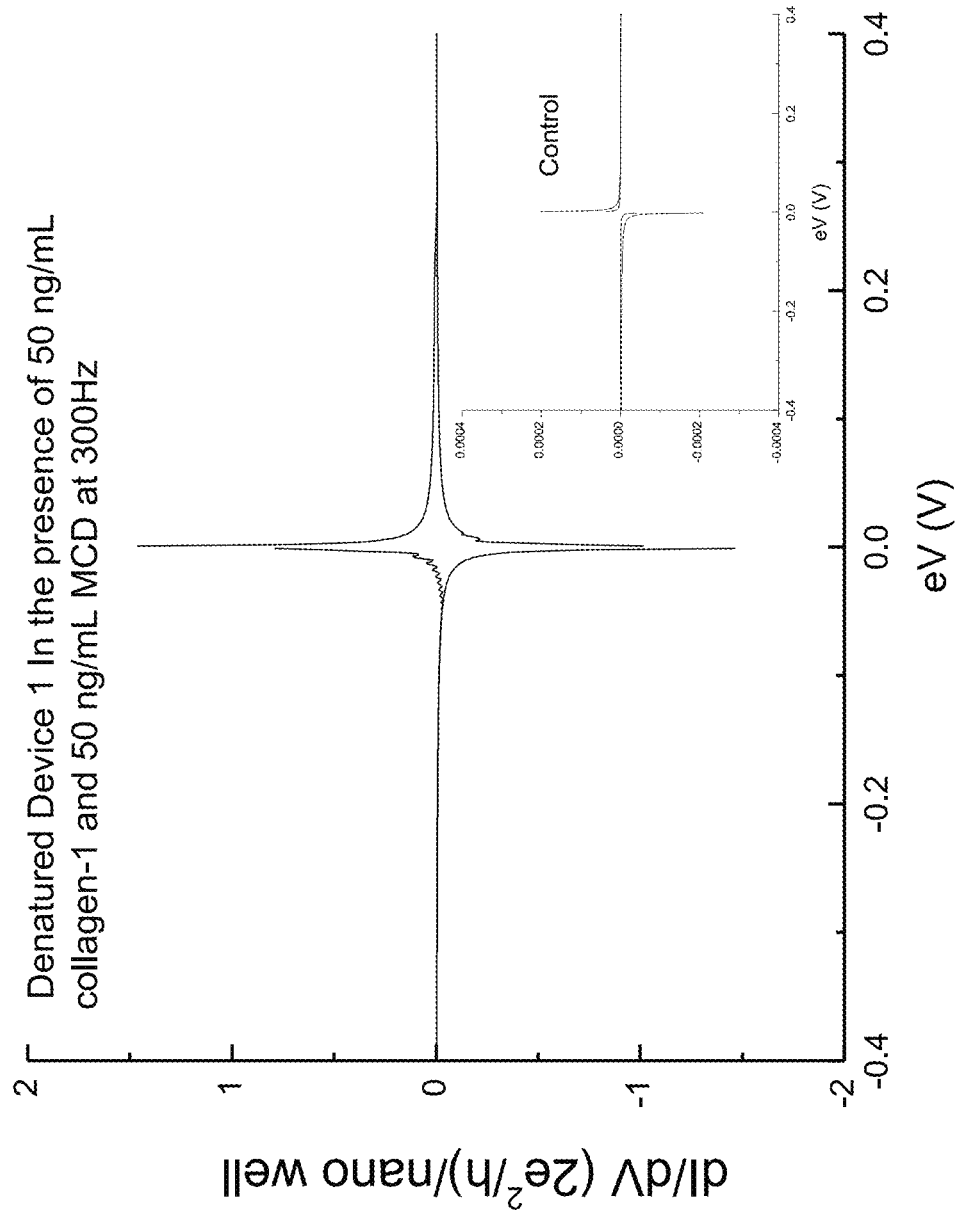
FIG. 11B depicts the superconductive density curve of dI/dV ($2e^2/h$) per nano toroidal well at zero-bias against the control shown in the insert in the PBS solution.

Evaluation of Topological Superconductor/Quantum Memcapacitor (TSC/QMC) Device in Superconductivity/Memcapacity The TSC/QMC Device 1. Device 1's characteristic is a TSC/QMC device. The JJ supercurrent at zero-voltage was observed using NIST human blood serum samples for with or without spiked collagen over concentration from 1 ng/mL to 200 ng/ml at the innate state as shown in the i-V curves in FIG. 10A (1.0 to 200 ng/mL) and FIG. 10B (1.0-100 ng/mL) by the CV method compared with the control shown in the insert figure. FIG. 10A and FIG. 10B show the current intensity increased as collagen-1 concentration increase at zero-voltage in room temperature at B=0, and the quantized dI/dV conductance increased as the collagen concentration increase shown in FIG. 10C. The JJ current intensity of the biomimetic activated state of MMP-2 in Device 1 was observed in PBS shown in FIG. 11A compared with PBS control having hysteresis characteristics shown in the insert; with the quantized conductance curve shown in FIG. 11B compared with that of control was in the insert. The observed different results of the quantized conductance in the presence of collagen at the circular JJ in FIG. 10C and FIG. 11B in two different states between an innate and an activated MMP-2 state in difference media, may indicate the activated state promoted a strong super conductance than the innate state; collagen played an important role in both media at both states, as a superconducting promoter and as a sensing analyte. It has been shown in our prior works that the well-aligned cyclodextrin donut-like cavities formed large nanopore toroidal wells with dipole polarized circular current flow in opposite directions induced a non-ferromagnetic field [22-24].

Example 7

Figure 12A:
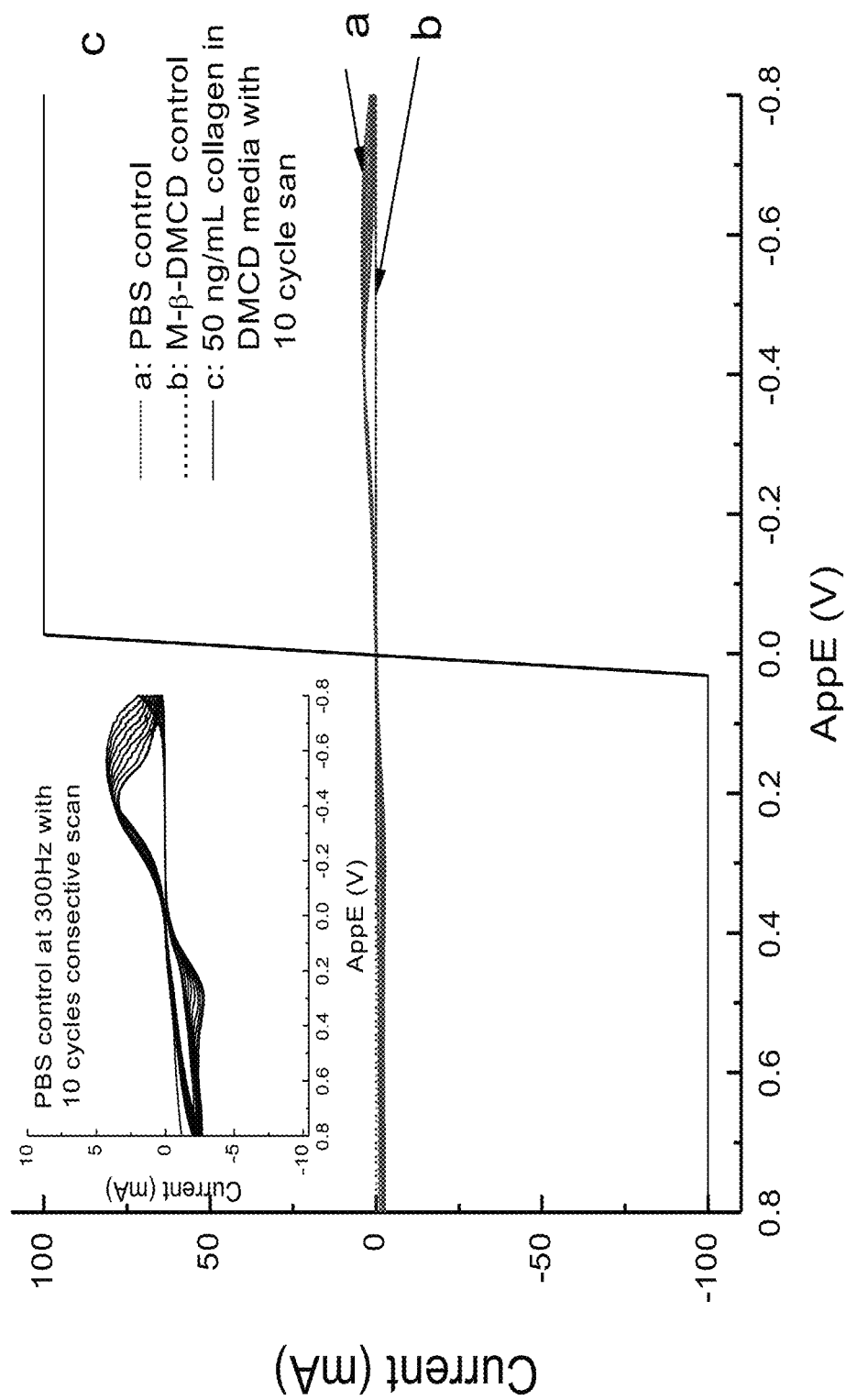
FIG. 12A depicts Device 2's superconductivity in PBS in the presence of 50 ng/mL collagen-1 and 50 ng/mL MCD compared with the controls with 300 Hz scan rate. The insert depicts the 10 cycle consecutive scans of the Device 2 in PBS solution.
Figure 12B:
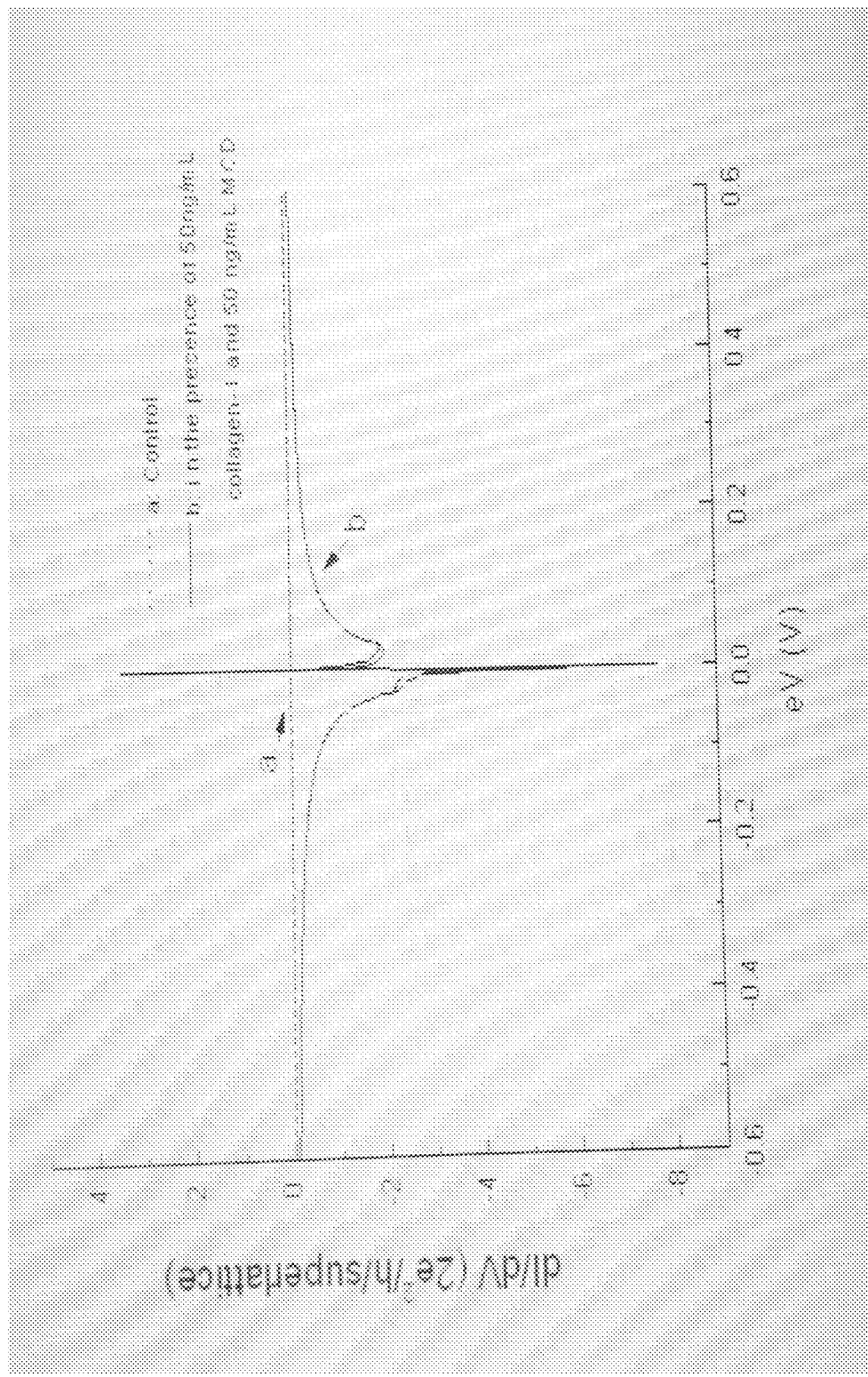
FIG. 12B depicts the superconductive density curves of dI/dV ($2e^2/h$) vs. per superlattice compared with that of in the control.

Evaluation of the Topological Superconductor/Quantum Memristor (TSC/QMR) Device 2 in Superconductivity/Memristivity The TSC/QMR Device 2. Device 2 utilized the first bottom layer of biomimetic CHAT as the pseudo-TSC layer under the assumption that injection of collagen-1 will promote direct super JJ circular current flow, plus the top second layer of bM-β-DMCD/TCD/PEG/PVP/$ZnCl_2$ without cysteine formed an activated biomimetic MMP-2 . . . CHAT relay tunnel with collagen-1 as the insulator layer and formed an S-I-S device, because the cross-linked polymer units repeated, wherein the device 2 has $SIS_n$ structures. Because the CHAT regulates the MMP-2 function and activity [22], FIG. 12A revealed the JJ super current was greatly increased at zero-voltage in the presence of 50 ng/mL collagen-1 and 50 ng/mL MCD in PBS solution compared with the PBS control and the MCD control as "a" and "b", while "c" is the one with collagen-1. The insert is the enlarged view of PBS control for 10 consecutive scans. The insert figure depicts the hysteric i-V curve of the control at 300 Hz scan rate. FIG. 12B depicts the quantum conductance density per superlattice in the presence of collagen which is 34-fold higher compared with the control. It is evident that the relay-enhanced the JJ supercurrent in the presence of 50 ng/mL collagen-1 and 50 ng/mL MCD when the large and small "donuts"-toroidal rings—alignment was in a place that promoted cooper pairs hopping at the junction tunnel.

Figure 28:
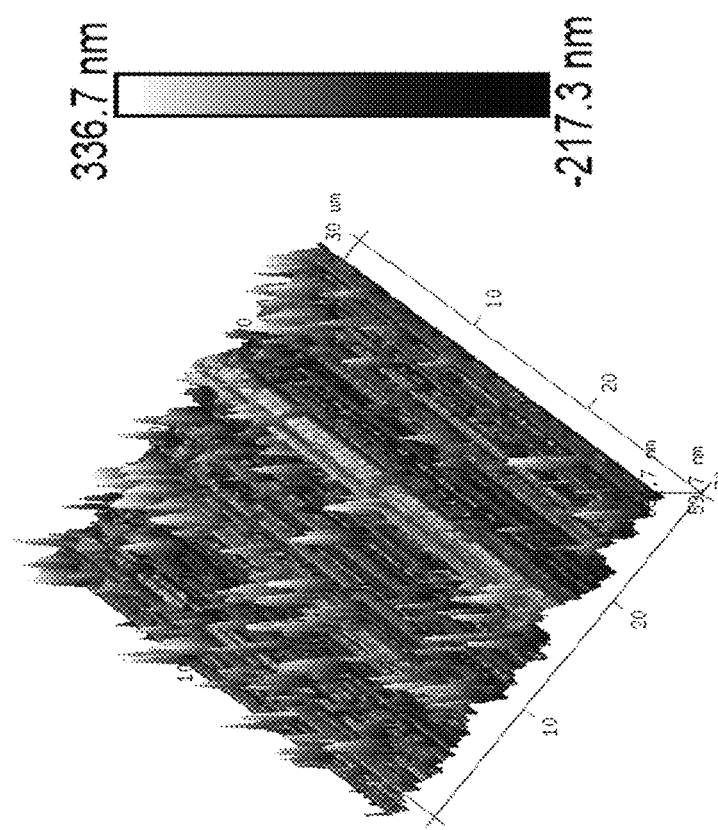
FIG. 28A depicts Sensor 1 of the HSP60 SAM's 3D image in an area of 1.0'1.0 µm² with a ±Z-value 259.3 nm.
FIG. 28B depicts the 3D AFM image.
FIG. 28C depicts the HSP60 cluster on the right-side corner, and the subunit cluster on the top left-side corner.
FIG. 28D depicts the top view of the HSP60 nanopore rings and the side view of the HSP60 structure.
FIG. 28E shows another cluster of HSP60 in a 1.4×1.4 µm² area, it emitted golden light beams from the HSP clusters.
FIG. 28F shows the image of nanotube density differently oriented on the top-hill area and on the low-lay canyon area of the 2D AFM image.
Figure 28:
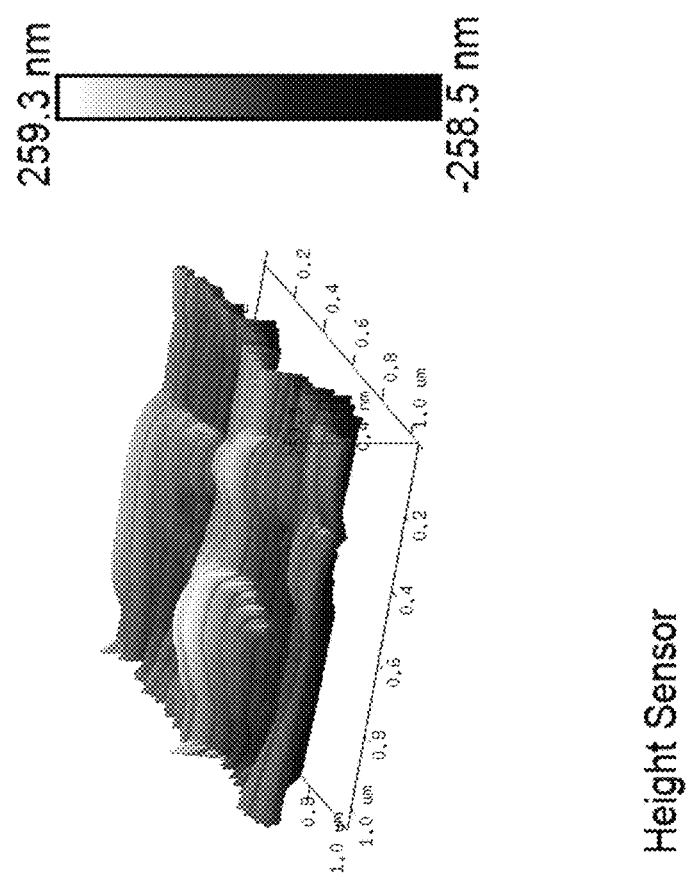

Device 2 utilized the first bottom layer of biomimetic CHAT as the pseudo TSC layer under the assumption that direct super JJ circular current flow will be promoted by the presence of collagen-1, and with the top layer of -bM-β-DMCD/TCD/PEG/PVP/ZnCl$_2$,—an activated biomimetic 3D collagen-1 . . . MMP-2 . . . CHAT relay tunnel may form an SIS/SIN device with the TSC/QMR function peak at zero-potential. Because the CHAT regulates the MMP-2 function and activity [21], FIG. 12A revealed that the JJ super current greatly increased at zero-potential compared with the controls, and the enlarged view of the PBS control shown in the insert with the hysteric i-V curve indicated the memristivity of the nature of Device 2. FIG. 12B depicts the quantum conductance density per superlattice in the presence of collagen-1 which is 34-fold higher compared with the control. Device 2's quantum conductance density per superlattice is $3.1 \times 10^{10}$, 13 and 1.33-fold higher than that of activated Device 3 at 1 Hz, 1 kHz, and 10 kHz, respectively as shown in FIG. 28H based on curves displayed in FIG. 14B.

Example 8

The Super Current of the Activated TSC/QMC Device 1 Have Wide Superconducting Bands in the Presence of Collagen-1

Figure 13B:
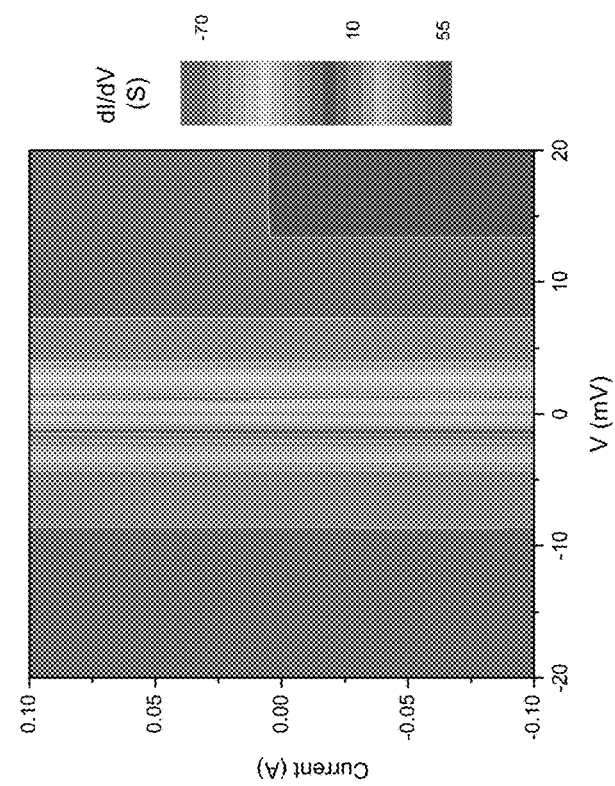
FIG. 13B depicts the contour map of the special trajectory of the superconductive band of ±70 Siemens (S) vs. supercurrent in the range of ±100 mA and in the potential range over 20 mV to −25 mV.
Figure 13A:
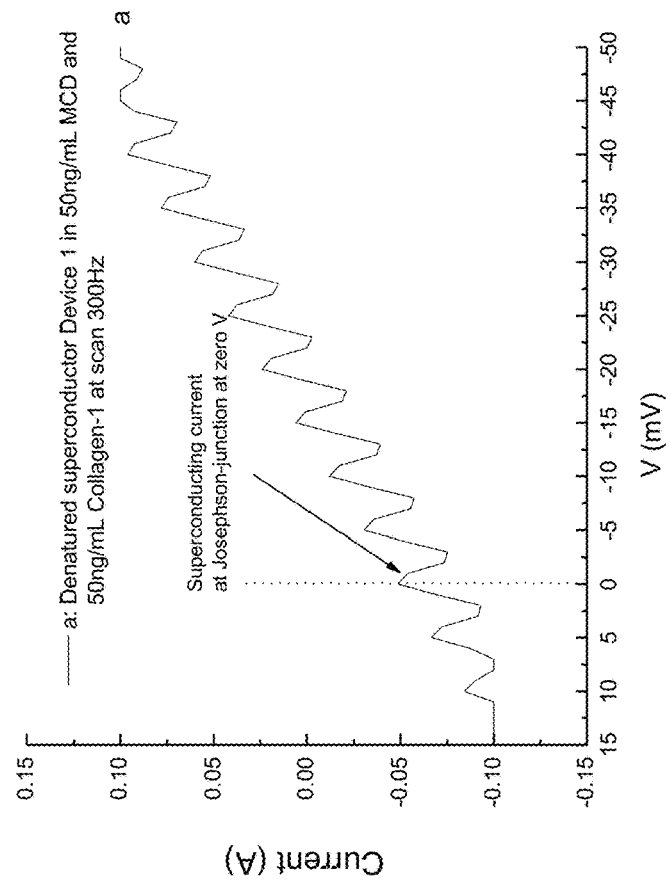
FIG. 13A depicts the zero-voltage peak of the denatured, i.e., activated Device 1 from the i-V curve in the presence of 50 ng/mL collagen-1 and 50 ng/mL MCD in PBS 7.4 solution at scan rate 300 Hz over 15 mV to −50 mV. The i-V curve came from FIG. 11A.
Figure 13C:
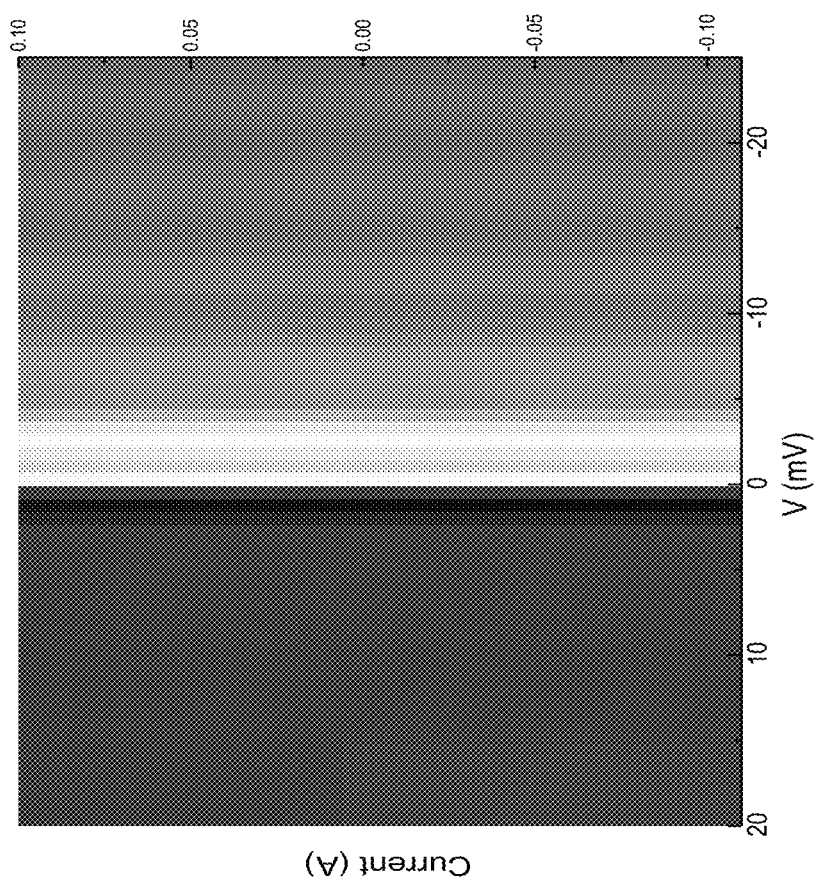
FIG. 13C depicts the 3D special location of the zero-voltage peak vs. supercurrent and vs. potential between 20 mV and −60 mV.
Figure 13D:
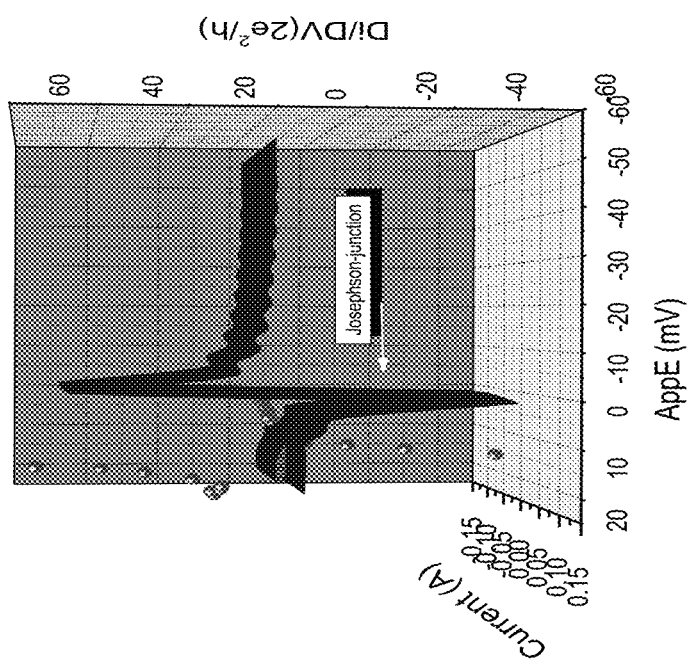
FIG. 13D depicts the image of the brightest wide superconducting energy bands at the zero-bias of the activated Device 1 for the coherent Cooper-pair and also shows the single-electron tunneling bands in deemed light under an external magnetic field=0 condition.

FIG. 13A depicts the zero-voltage superconducting peak of the activated Device 1 in the presence of 50 ng/mL collagen-1 and 50 ng/mL MCD in PBS 7.4 solution at scan rate 300 Hz over 15 mV to −50 mV, that was based on the i-V curves came from FIG. 11A. FIG. 13B depicts the special trajectory of the superconductive band of ±70 S vs. supercurrent in the range of ±100 mA and in the potential range over 20 mV to −25 mV. FIG. 13C depicts the 3D special location of the zero-voltage peak vs. supercurrent and vs. potential between 20 mV and −60 mV. FIG. 13D depicts the image of the brightest wide superconducting energy bands at the zero-bias of the activated Device 1 showing the coherent Cooper-pair crossover the barrier and also shows the single-electron tunneling bands in deemed light in the negative potential field under an external magnetic field=0 condition, that indicates the characteristics of the Josephson ring vortex effect.

Example 9

Evaluation of the Innate Protein Superconductive/Memristive Device 3

Figure 14A:
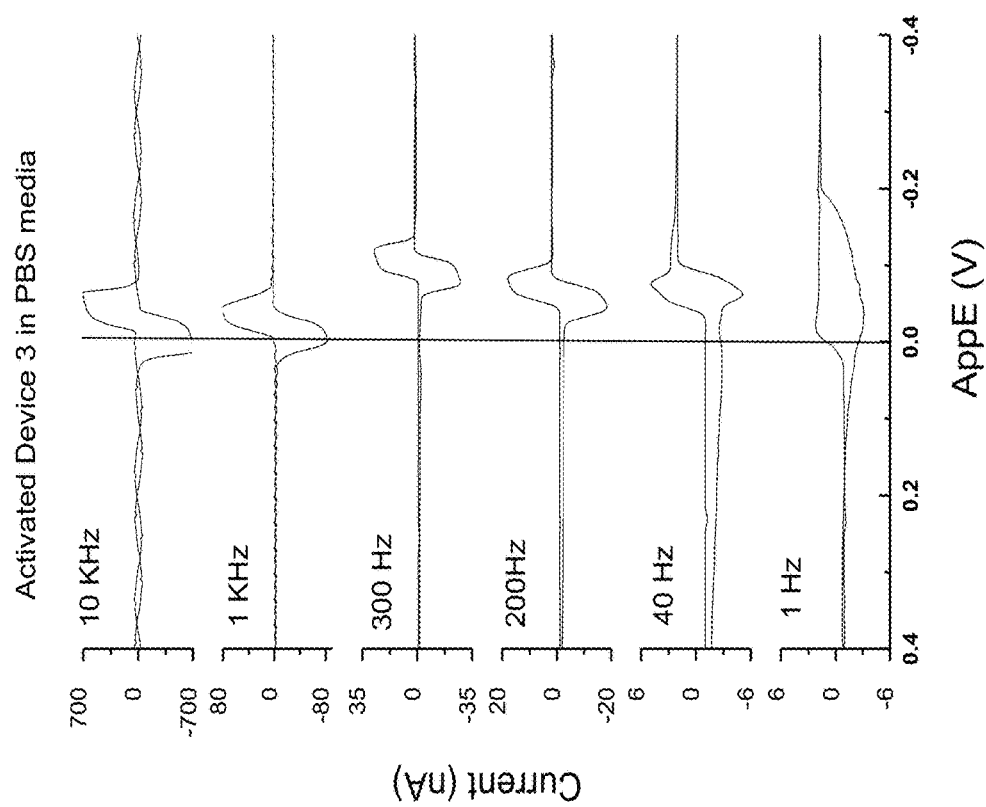
FIG. 14A depicts i-V profiles of the innate Device 3 in PBS solution with scan rate from 1 Hz to 10 kHz.
Figure 14B:
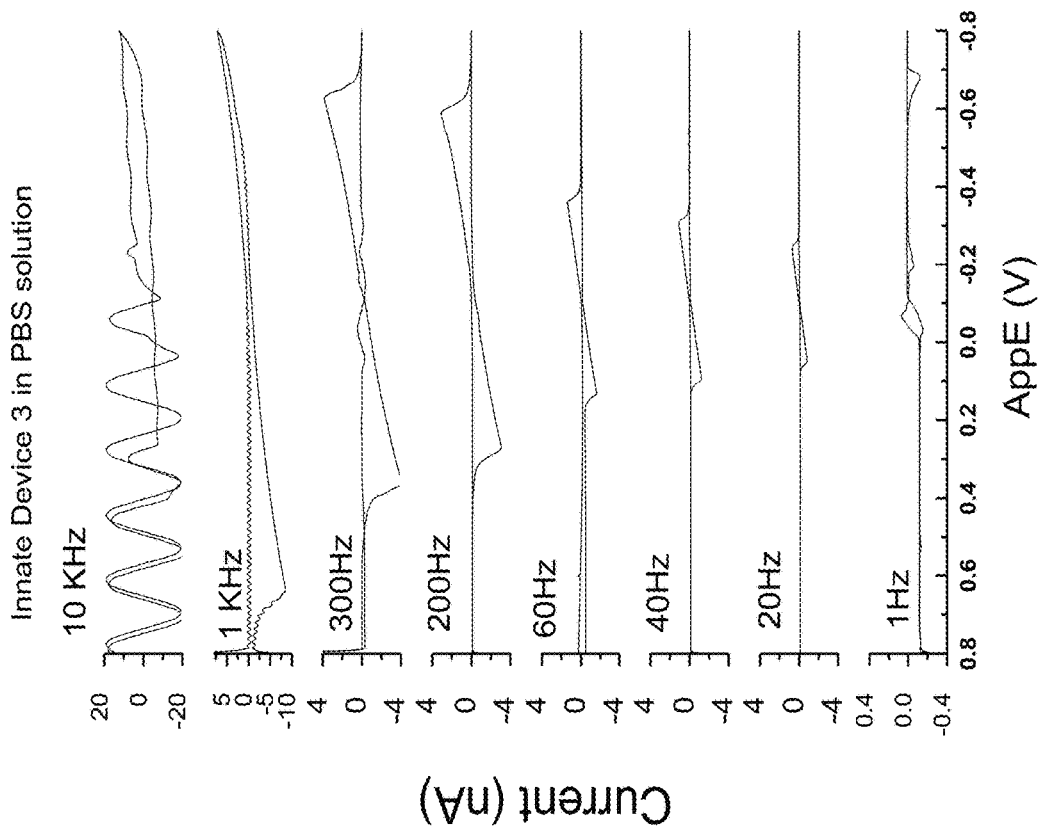
FIG. 14B depicts i-V profiles of the activated protein Device 3 in PBS solution over 1 Hz to 10 kHz.

The Native Protein Device. The native MMP-2 protein has two states: an innate state with the cysteine "on" and an activated state with the cysteine "off". FIG. 14A depicts i-V profiles of the innate Device 3 in PBS solution with scan rate from 1 Hz to 10 kHz. FIG. 14B depicts i-V profiles of the activated protein Device 3 in PBS solution over 1 Hz to 10 kHz. FIG. 14C depicts the i-V profiles of the innate Device 3 in the presence of various collagen-1 concentrations from 500 fg/mL to 25 ng/mL compared with the PBS control solution at 300 Hz scan rate. The innate MMP-2 Device 3 shows no superconductivity when spiked with 500 pg/mL collagen-1 concentration at 300 Hz depicted in FIG. 14C compared with the i-V profiles shown in FIG. 14A and FIG. 14B, respectively. However, hysteresis curves occurred in lower collagen concentration. The transformation from hysteresis to "pseudo superconducting" peaks was observed when concentration increased from 0.5 pg/mL to 0.5 ng/mL as shown in FIG. 14C for the innate Device 3 and with an enlarged view shown in FIG. 14G. FIG. 14B depicts the activated Device 3 having the JJ tunneling current at very low 1 Hz and high 1 kHz and 10 kHz in PBS with phase exchange and oscillation occurred. FIG. 14D depicts the i-V curves of the activated Device 3 in the presence of various collagen-1 concentrations compared with controls at 300 Hz.

Figure 14E:
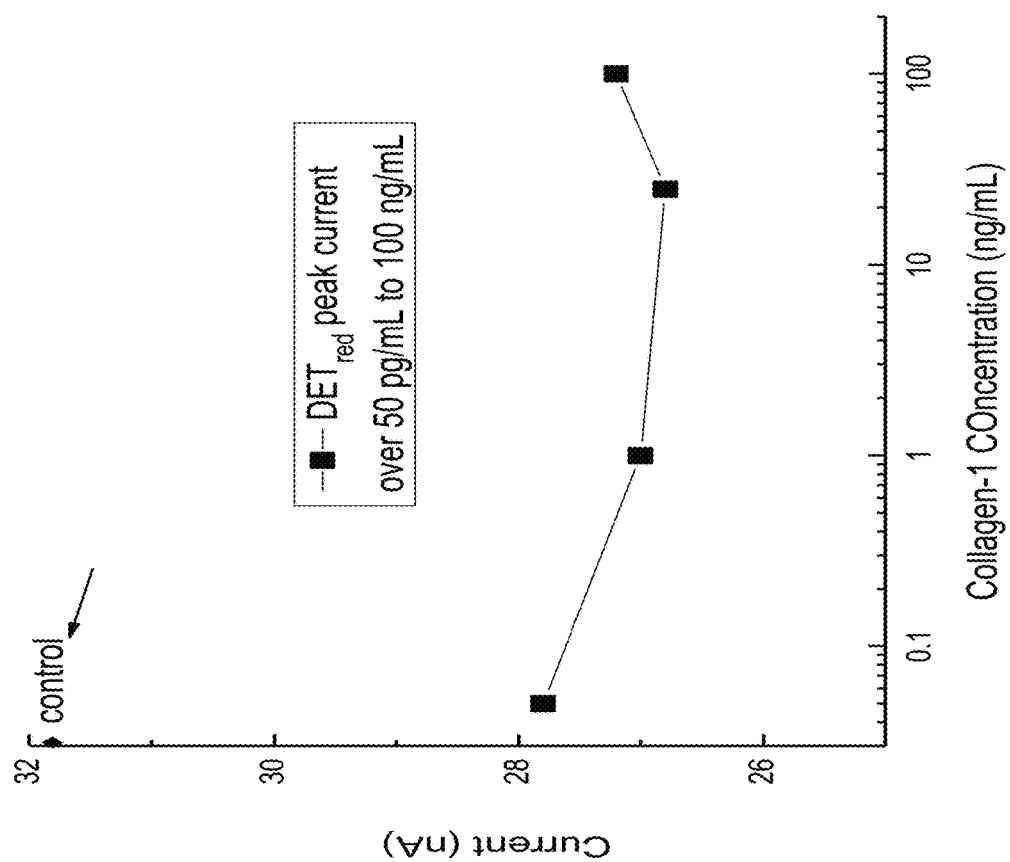
FIG. 14E depicts the i-V profiles of the activated Device 3 with or w/o spiking collagen-1 in human capillary blood serum at scan rate 300 Hz.
Figure 14F:
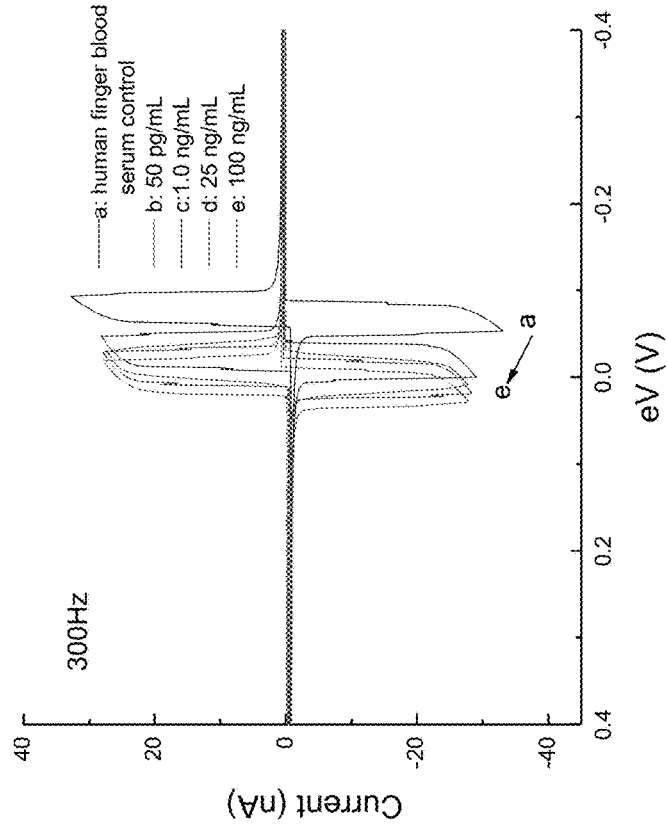
FIG. 14F depicts the current decay curve vs. collagen-1 concentration from 50 pg/mL to 100 ng/mL compared to control of the human capillary blood serum sample.

FIG. 14E depicts the activated Device 3 communicates with collagen-1 in a superconducting way upon increased spiked concentration in human capillary blood specimen samples over 50 pg/mL to 100 ng/mL at 300 Hz compared with the human capillary serum control. FIG. 14F shows there is an inverted relationship between the collagen concentration and the JJ current; while the location of the peak observed is closer at the zero-voltage trajectory using human capillary blood serum when concentration increased from 50 pg/mL to 100 ng/mL at 300 Hz. FIG. 14G depicts the detail i-V profiles of FIG. 14E showing the zero-voltage peaks. The memristivity was observed over the scan rate change from 1 Hz to 1 kHz in 7 levels for Device 3 at the innate state. The electrochemical potential distance between the direct electron-transfer (DET)/red peak to $DET_{ox}$ peak observed is in an exponentially accelerating apart manner as the scan rate increases having a first-order rate constant of 3.94 $(Hz)^{-1}$ far away from each other, this indicates in the absence of collagen, the memristive device is highly bidirectional polarized and the increased circular current intensity is exponentially proportional to the scan rate increase herein the net power is exponentially increased from 1 Hz up to 300 Hz. The charge of the peaks carried also followed the exponential increase pattern except at 1 kHz, the charge was drastically reduced shown in FIG. 14A. This phenomenon observed was the typical memristive device behavior and agreed with the literature [24]. At 10 kHz, the sine wave oscillating was observed. Superconductivity at 1 Hz might offer a benefit to infants' declarative memory consolidation in neuronal bidirectional circuitry development; because infants spend 16 hours per day asleep with half of that time at the slow wave sleep (SWS) stage from 0.5-2 Hz frequency [33-34]. FIG. 14H depicts the oscillation zero-voltage peaks of the activated Device 3 in PBS control solution at 1 Hz, 1 kHz, 10 kHz, respectively. FIG. 28I depicts the plots of the current intensity change between $DET_{red}$ and $DET_{ox}$ peaks vs. scan frequency (1 to 10 kHz) between the innate and the activated state, respectively. The activated state of Device 3 has both a 50 and 10-fold increase in current intensity compared to the innate state for $DET_{red}$ and $DET_{ox}$, respectively. Activated Device 3 has no zero-potential conductance at 300 Hz. It verified the fact that the large and small "donuts" or toroidal rings' alignment in the superlattice promotes the cooper pairs' hopping with the holes at the junction tunnel.

Example 10

Quantitation of Collagen-1 by the CV Method

Figure 15A:
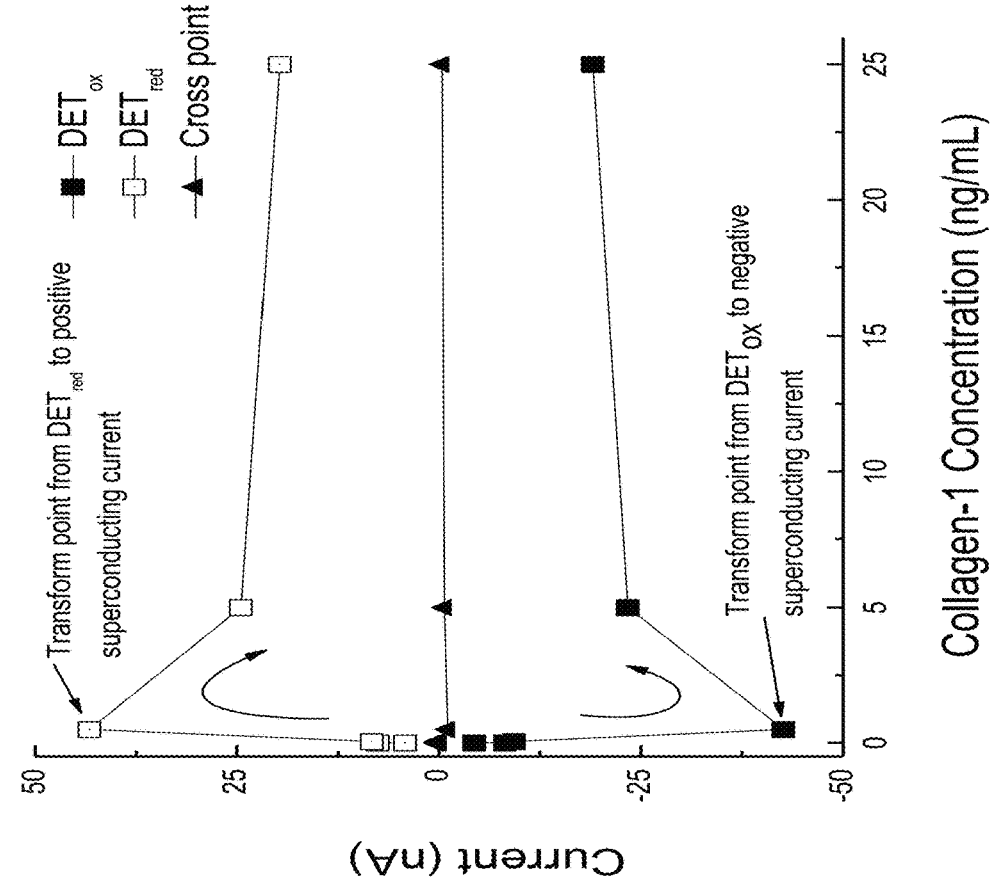
FIG. 15A depicts the exponential JJ super current vs. collagen-1 concentrations curves over 1 ng/mL to 200 ng/mL of $DEL_{red}$ and $DET_{ox}$ peaks of Device 1 at the innate state at 300 Hz scan rate using NIST human serum samples.
Figure 15B:
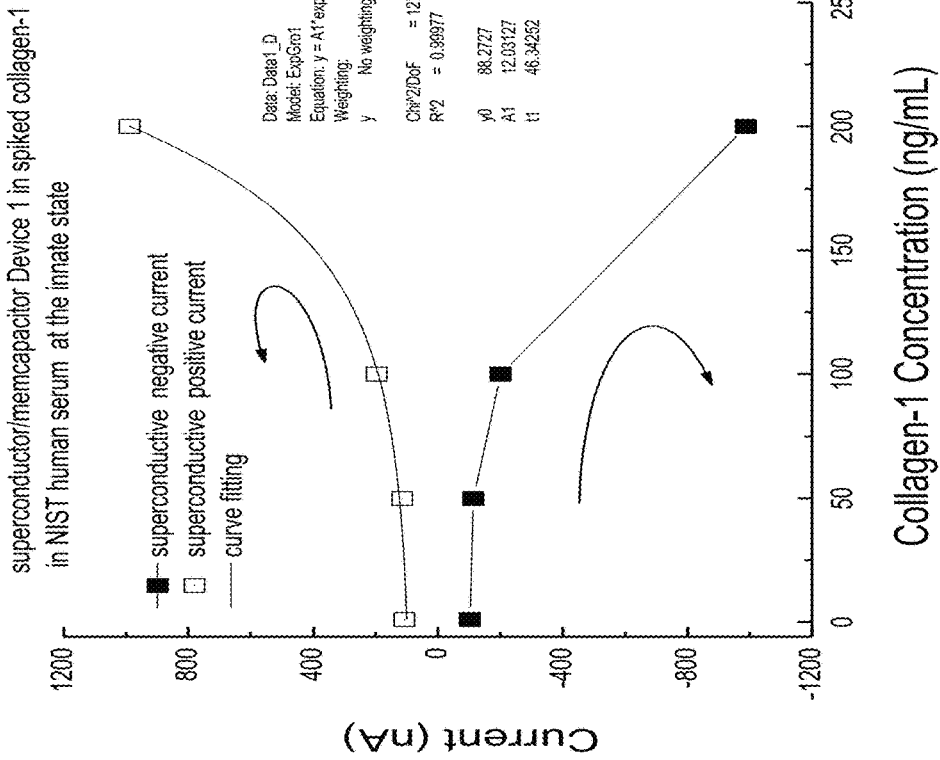
FIG. 15B depicts the trends of current vs. collagen-1 concentrations curves over 0.5 pg/mL to 25 ng/mL of the innate Device 3 in PBS solution at 300 Hz. The transform points from memristive to superconductive peaks are shown according to the original CV curves in FIG. 15C.

FIG. 15A depicts the $DET_{red}$ and $DET_{ox}$ peak intensity exponentially increase/decrease vs. collagen-1 concentration, respectively over 1-200 ng/mL that was based on the CV profiles obtained in FIG. 10A and FIG. 10B on the innate Device 1 compared with the control using NIST human serum samples. Activated protein Device 3 has the CV profiles shown in FIG. 14E and FIG. 14G using human capillary serum specimens having 13% signal intensity over 50 pg/mL to 100 ng/mL compared with Device 1. FIG. 14F depicts the current has an exponential decay relationship as the collagen-1 concentration increase. FIG. 15B depicts a plot of the innate Device 3 having a linear range from 0.5 pg/mL to 0.5 ng/mL in PBS based on i-V curves in FIG. 14C. FIG. 15C depicts the trend of the electrochemical potential of $DET_{red}$ and $DET_{ox}$ peaks moves as a function of concentrations of collagen-1 over 0.5 pg/mL to 25 ng/mL of the innate Device 3 according to the FIG. 14C described.

Example 11

The Superconductive-Memristive Switches Under Extremely Low Collagen-1 Concentration for the Innate Device 1

It was our first observation that the superconductive-memristive switches coexist in a JJ toroidal vortex without an external magnetic field applied at room temperature under an extreme low collagen-1 concentration 0.5 pg/mL in a fixed scan rate 300 Hz in NIST serum upon consecutive multiple cycles of scans. FIG. 16A depicts the innate Device 1 in 0.5 pg/mL collagen-1 at the first scan cycle with both, superconducting current and hysteresis point located at zero-potential. The insert shows the hysteresis point at zero-potential, while located in the superconducting band. FIG. 16B depicts the second scan cycle; FIG. 16C depicts the third scan cycle; FIG. 30D depicts the fourth scan cycle; FIG. 16E depicts the fifth scan cycle and FIG. 16F depicts the control of NIST serum sample with pure memristive characteristics. This device will be found wide utilities in supercomputing with memory and no energy dissipation.

Example 12

Embedded Fractional Phase Change Promotes the Transformation from Memristive Sensing to JJ Toroidal Vortex Superconducting Reducing of the quantum energy gap between two superconducting peaks at the edge of ±2Δ value is very important, because superconducting peaks are occurring in the quantum gap range±3 mV. Research groups reported some approaches for reducing the gaps [37]. FIG. 15C depicts the potential trajectory trends of the DET peaks as the collagen-1 concentration increase from 0.5 pg/mL to 25 ng/mL of the innate Device 3 in PBS solution at 300 Hz that were based on the i-V profiles in FIG. 14C. The results indicate the fact that the distance between $DET_{red}$ and $DET_{ox}$ peaks was shortened as the collagen-1 concentration increases, that implies collagen-1 promotes for reducing of the quantum energy gap between superconducting peaks±2Δ value in order to make the transition from memristive to superconductive possible near the superconducting peaks working range at ±3 mV. FIG. 15C also implies collagen-1 drags bidirectional polarized sensor to the zero-bias and to be non-polarizable for superconducting purpose.

FIG. 16A depicts the innate Device 1 in 0.5 pg/mL collagen-1 using NIST human serum at 300 Hz at the first scan cycle with both, superconducting current and hysteresis point located at zero-potential. The insert shows the hysteresis point at zero-potential, while located in the superconducting band. FIG. 16B depicts the second scan cycle; FIG. 16C depicts the third scan cycle; FIG. 16D depicts the fourth scan cycle; FIG. 16E depicts the fifth scan cycle and FIG. 16F depicts the control of NIST serum sample with pure memristive characteristics. Its hysteretic cross point at v=0 with 10-fold higher JJ current than that of at 200 ng/mL, that indicates in extreme low collagen concentration, the quantum superconductor/memcapacitor device also can serve as a memristive device; hence not surprisingly we observed the quick phase change of the JJ wave during a 5 consecutive scan at 300 Hz compared with the NIST serum control at 300 Hz. The phenomenon may imply a blastocyst cell develops in a surprising way of topological quantum superconductive/memcapacitive/memristive properties in place when extra low collagen-1 communicates MMP-2 in the blood membrane.

Example 13

Quantitation of Collagen-1 by the Voltage Method

Quantitation of collagen-1 was conducted in three methods: a voltage method, a CA method and a CV method in two media: PBS solution and human serum samples. The voltage method and the CA method each sample run triplicates against the controls in the range over 0.5 pg/mL to 200 ng/mL. FIG. 17A depicts the curves of voltage vs. time at 0.25 Hz at ±10 nA over 0.5 pg/mL to 200 ng/mL collagen-1 concentrations against the control samples using Device 1 at the innate state in PBS solution. FIG. 17B depicts the calibration curve of action potential vs. collagen concentration, and it produced a linear regression equation Y=3.1-0.015x, r=0.995 (n=18), P<0.0001, Sy/x=0.12 over collagen-1 concentration 0.5 pg/mL to 200 ng/mL with a pooled relative sum of squares pure error (PRSSPE) of 2.0%.

Figure 18A:
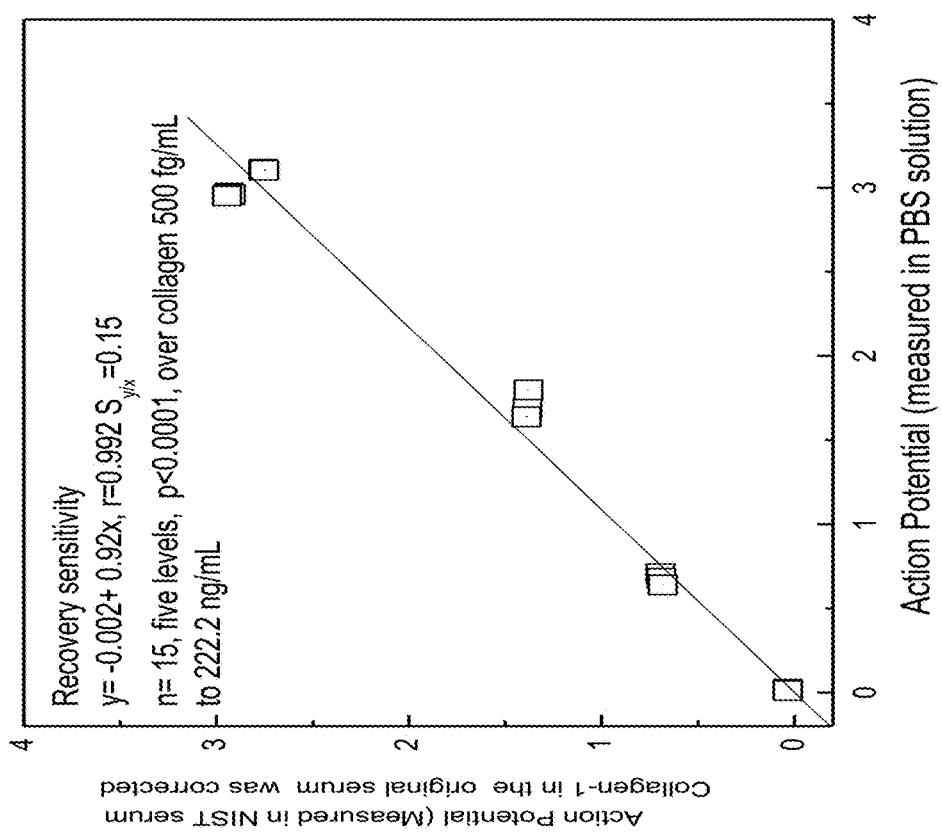
FIG. 18A depicts the voltage profiles in human serum with or w/o spiking collagen with innate Device 1.
Figure 18B:
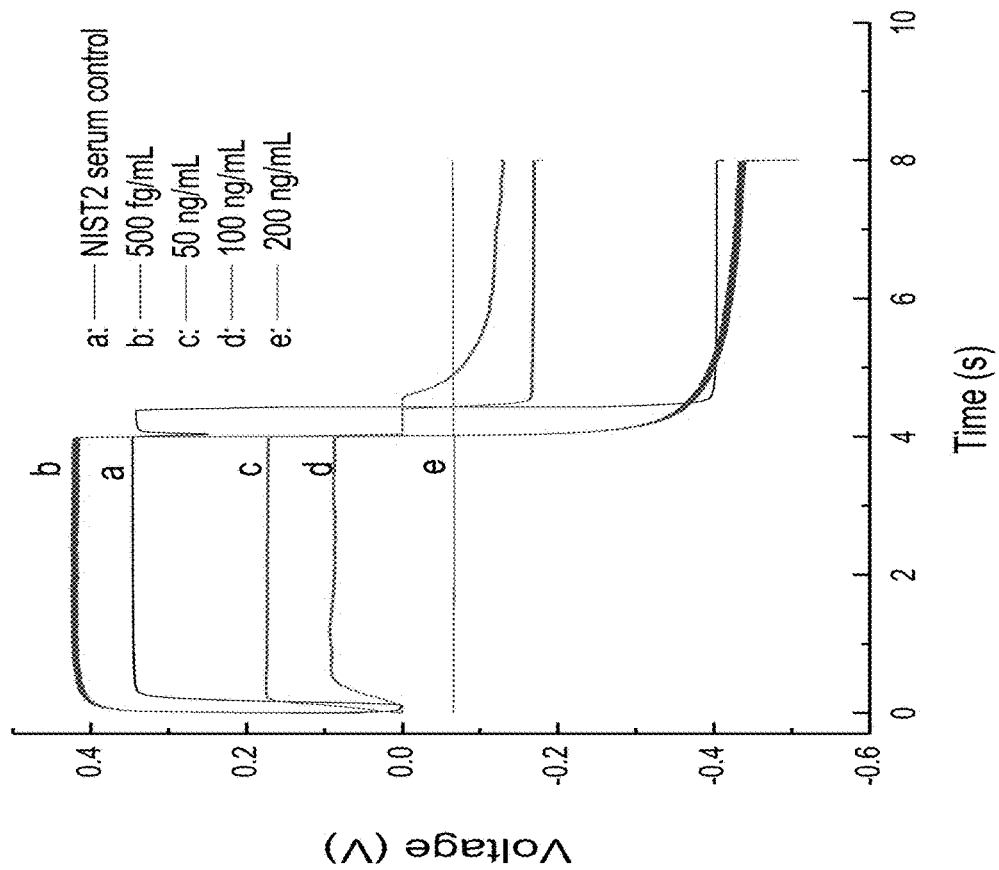
FIG. 18B depicts the linear regression curve of the measured collagen in PBS vs. that in serum after corrected the control effect before spiking.

The method accuracy and imprecision was studied through the recovery experiments on Device 1 compared with Device 3 by using pure NIST human serum specimens spiked with 4 levels of collagen-1 concentrations over 500 fg/mL to 200 ng/mL. Results obtained shown in FIG. 18A are the voltage profiles and FIG. 18B depicts the linear regression plot of measured collagen in PBS vs. that of in NIST2 serum over the studied range after included the serum control's collagen-1 concentration according to the standard curve. FIG. 19A presented is for the trend of the voltage in resting potential peaks over the same concentration range tested. FIG. 19B is the same as FIG. 17B. FIG. 19C depicts the cell energy density curve vs. collagen-1 concentrations. The recovery results have an agreement of 92±0.03% over the studied range. The imprecision of the PRSSPE error was 0.3% (n=15). Device 2 and Device 3 have failed using the voltage method.

Example 14

The JJ Toroidal Vortex Characteristics

The hallmarks of the JJ characteristics are (1) at a DC voltage=0, $$I_s = I_c \sin(\Delta\varphi) \quad (1)$$

$I_s$ is the supercurrent, $I_c$ is critical current, $\Delta\varphi$ is the phase difference between the waves of two superconductors appears at the DC Josephson junction; (2) at a finite DC voltage, the phase change of the superconducting wave vs. time caused oscillating at the AC Josephson Junction, and is proportional to $2eV_{DC}$, i.e., $$\partial\varphi/\partial t \propto 2eV_{DC}. \quad (2) \ [10\text{-}12]$$

Figure 34:
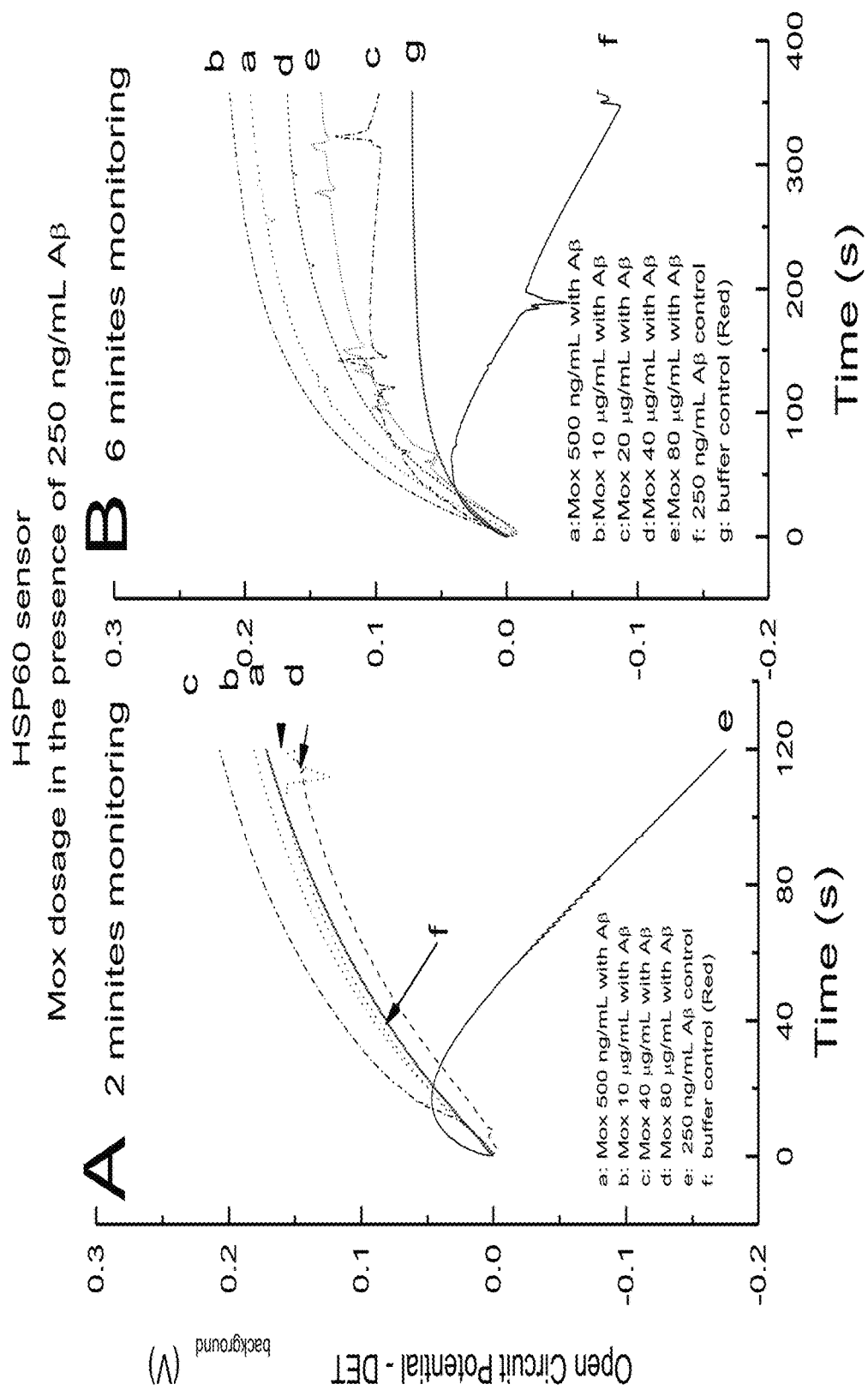
FIG. 34 depicts various concentrations of HOX impaired 250 ng/mL Aβ folding on the open circuit potential vs. 2 and 6 minutes compared with controls, respectively.

FIG. 34 shows the trend of the comparison of the amplitude of the JJ super AC current among the three devices: the magnitude of the activated Device 1 in the PBS control solution is 29-fold and 260-fold higher than Device 2 and the innate Device 3, respectively by the Chronoamperometric method (CA) under zero-potential for each of the two steps with fixed 10 kHz data rate for each step. Device 2's super current magnitude is 9.5-fold higher than that of Device 3. A method has developed to quantify the Friedel-oscillation observed in the Example 5 and linked it with the results from the CA method under the double step zero-potential approach, herein the order of the Friedel-oscillation frequency among the three devices was Device 3>activated Device 1>Device 2, i.e., 83.33 Hz/peak>76.9 Hz/peak>55.56 Hz/peak, respectively. Under the same data rate, within the 0.8 s period, Device 3 has 66.7 peaks, the activated Device 1 has 61.5 peaks and Device 2 has 44 peaks. It was verified that our CHAT . . . biomimetic MMP-2 . . . collagen-1 approach has paved a road to reduce the JJ tunnel strong oscillation in order to enable detecting extremely low concentration of collagen-1 by the CA method, Device 1 and Device 3 were failed the CA method to detect collagen-1 due to the very strong oscillation in both, control solution and in the presence of collagen.

Another method used to characterize the JJ toroidal vortex is to use the DC potential amperometry (DCPA) method. FIG. 21A depicts DC curves vs. time under zero potential compared between Device 2 and the innate Device 3. The results indicate Device 2 has a higher eternal power for spontaneous producing an initial current (−0.8 μA) at t=0, and an applied potential=0, vs. Device 3 which has a small and negligible eternal power with an initial rate of 0.28 nA/s went to an exponential drop to the s-s state, which is 148.6-fold weaker than Device 2. It is another example verifying Device 2's superconductivity is superior to Device 3. In general, under a non-zero applied DC voltage in a buffer solution, the current will exponentially drop to the steady-state (s-s) state at a definite time interval from the sensor in order to reach the equilibrium state from the non-Faraday current, but in contrast, Device 2's current goes up with an initial rate of 41.6 nA/s towards the cathode, which is a known electron pop-hop transport phenomena between the transition metal zinc and the $d_\pi$ from polymer receptors [30-31], i.e., cooper pairs quantum transport their electrons which are exchanged with holes of the receptors in the superlattice membrane. As Liao mentioned in his report, zinc metal coordinates well with the tetraphenylporphine nitrogen atoms better than Fe, Co, Ni, and Cu, because zinc's $d_{x2-y2}$ orbital energy significantly dropped, in favor of coordination with the dam, i.e., π-cation radical, hence our experiment supports his finding that the $d_\pi$ orbital may dominate the electron relay [32]. FIG. 21B depicts DC current curves vs. time under zero potential compared between Device 1 and the innate Device 3, which indicates the innate Device 1 has an initial rate of 13.08 nA/s increase up to an exponential increase towards the cathode, which is 3.2-fold slower than that of Device 2.

Figure 22:
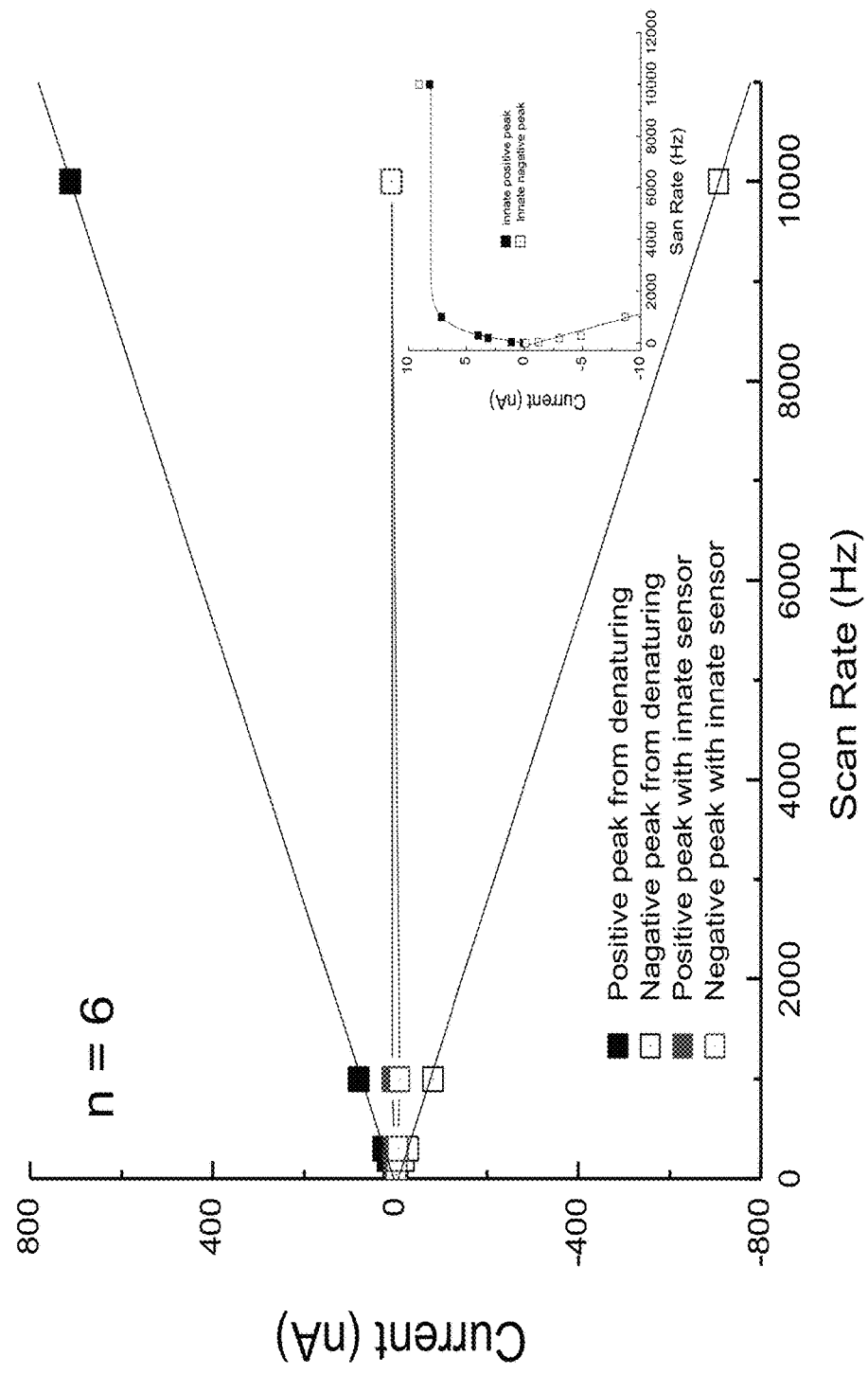
FIG. 22 depicts the curve current intensity comparison between innate and activated states for Device 3 in PBS solution vs. scan rate over 1 Hz, 40 Hz, 200 Hz, 300 Hz, 1 kHz, and 10 kHz by the CV method. The insert is the enlarged view of the innate state Device 3.

The third method used to validate the activated Device 3's i-V profiles compared with the innate Device 3 is the CV method. FIG. 22 depicts the current intensity vs. scan rate compared between the $DET_{red}$, $DET_{ox}$ at the innate and the activated states of Device 3 in the PBS solution, respectively. The scan rate was over 1 Hz, 40 Hz, 200 Hz, 300 Hz, 1 kHz, and 10 kHz (n=6). The insert is the enlarged view of the innate state Device 3. The results indicate the intensity of the peak current at the activated state of $DET_{red}$ vs. scan rate has a linear sensitivity of 0.07 nA/Hz, which is 31.8-fold higher than that of the innate state, that has a non-linear first-order constant of 0.0022/Hz. That indicates Device 3 used extremely short time reached the s-s than Device 2. A similar trend was observed for $DET_{ox}$ between the activated vs. the innate Device 3.

Example 15

The Fractional Phase Change of JJ Toroidal Vortex Initiated Superconductivity

Figure 23B:
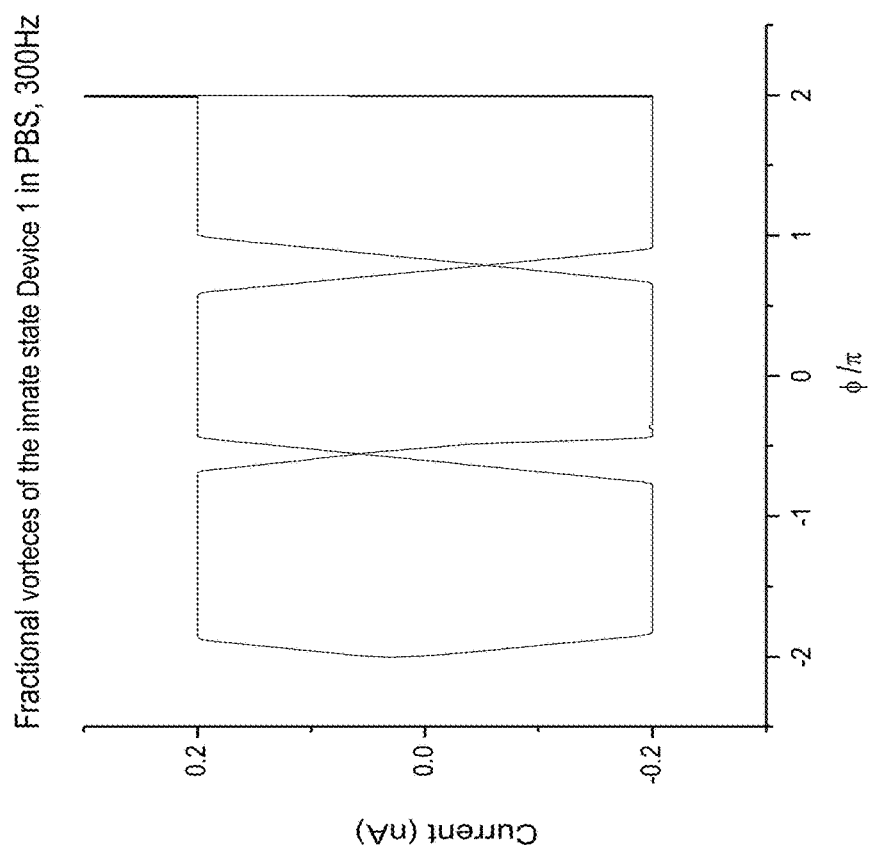
FIG. 23B depicts the fractional phase changes of the innate state Device 1 in PBS solution at 300 Hz.
Figure 23A:
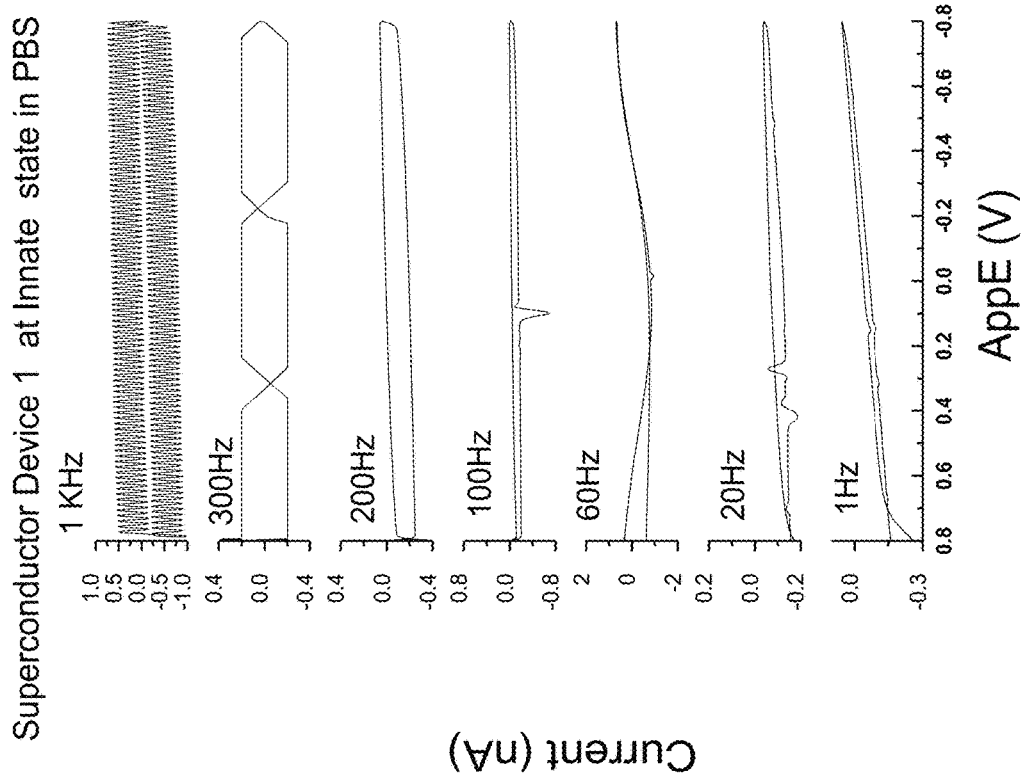
FIG. 23A depicts the phase changes of the i-V cures vs. scan rate of the innate state Device 1 in PBS solutions.

Fractional Josephson vertices depends on the supercurrent loops created a magnetic flux in which the superconducting phase discontinuities [35]. The fractional Josephson effect predicted theoretically can be existed in the absence of an applied magnetic flux, which enables the efficient topological qubit readout [36], however, it was not observed. FIG. 23A depicts the phase changes of the i-V cures vs. scan rate of the innate state Device 1 in PBS solutions. FIG. 23B depicts the fractional phase changes of the innate Device 1 in PBS solution at 300 Hz. Not like Device 2 and innate Device 3, they are memristive in nature in the PBS solution at 300 Hz, the innate Device 1 has no observable DET peaks in the scan range from 1 Hz to 10 kHz in PBS solution, notably is the i-V curve at 300 Hz possessed the fractional phase change as shown in FIG. 23B. Oscillation was observed in 10 kHz in FIG. 23A. Therefore, the evidence of the innate Device 1 direct detects collagen-1 using the voltage method, presented in the following section and was initiated by the fractional phase change that leads to the memcapacitive characteristic and function. Nevertheless, the innate Device 1 in human blood media, its i-V curve has hysteresis function. Because the collagen-1 does present in human serum, it may change the nature of the i-V curve.

Example 16

Quantitation of Collagen-1 by the CA Method

Figure 24A:
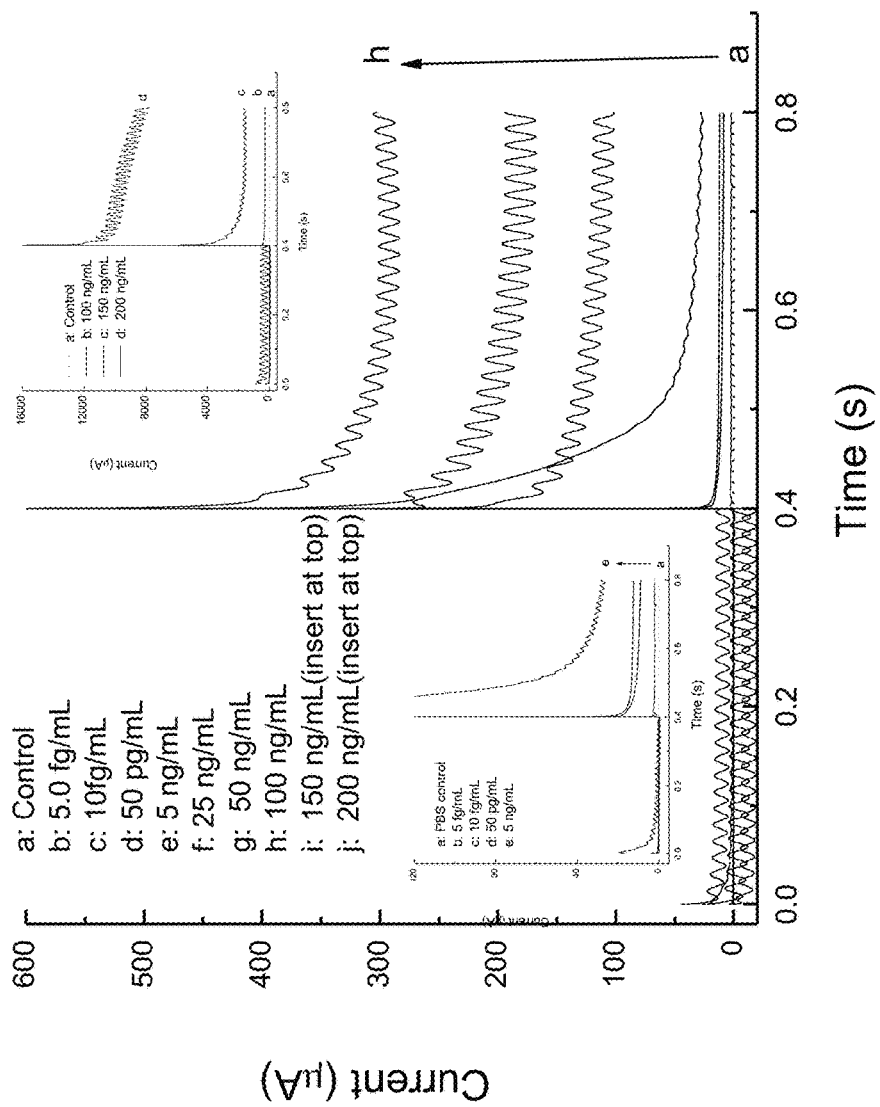
FIG. 24A depicts Device 2's current profiles over collagen levels 5.0 fg/mL to 200 ng/mL (9 levels from "a" to "j") vs. controls in PBS solution. Samples run triplicates. Inserts are for the enlarged view for the results at high and low-end concentration levels compared with controls.
Figure 24C:
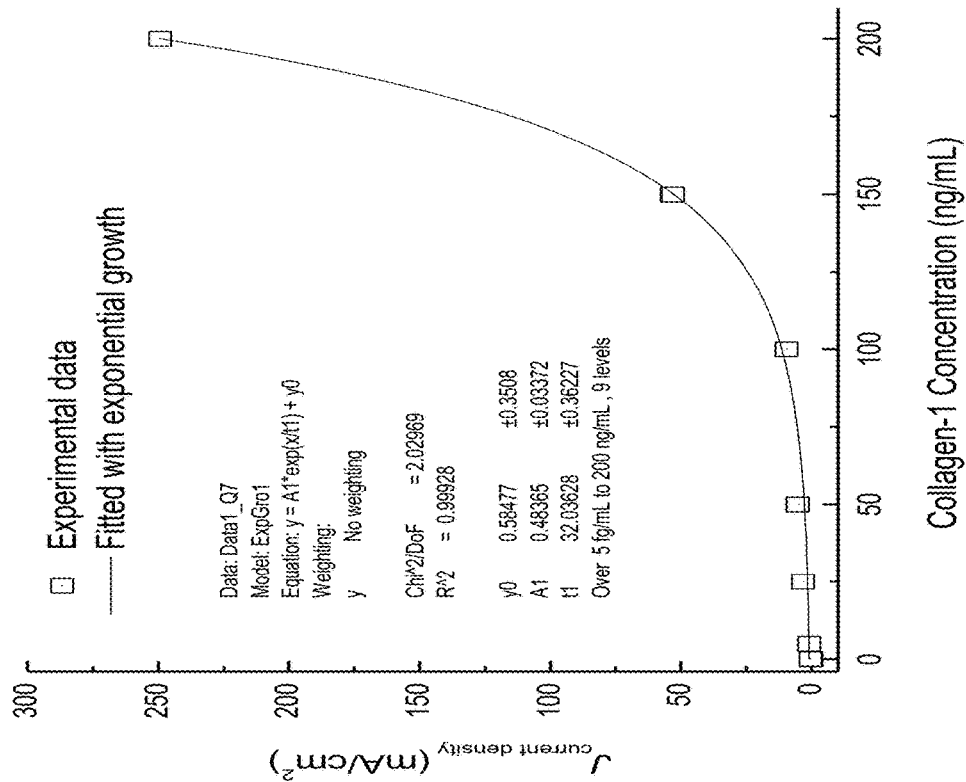
FIG. 24C depicts the calibration curve of current density vs. collagen-1 concentration in an exponentially increase manner over 5.0 fg/mL to 200 ng/mL (9 levels). Samples run triplicates.
Figure 24B:
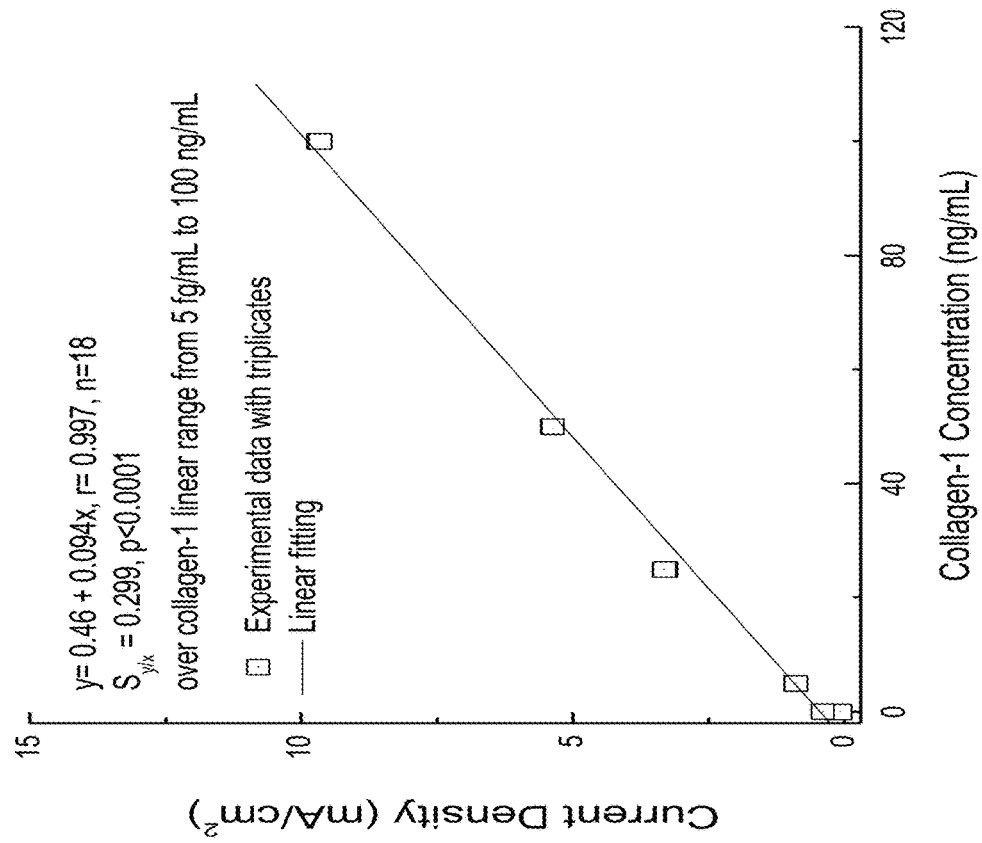
FIG. 24B depicts the calibration curve of current density vs. collagen-1 concentrations over the linear range of 5 fg/mL to 100 ng/mL (6 levels).

Using the biomimetic "CHAT . . . MMP-2" direct electron relay approach, i.e., "Predator catfish . . . Brachyhypopomus electric fish" approach, we were able to reduce the strong Friedel-oscillation at the long-range JJ toroidal vortex compared with that of Device 1 and Device 3. We were able to directly detect collagen-1 in sub fg/mL under labeling—free and antibody protein-free and reagent-free conditions. FIG. 24A depicts the plots of current vs. time under −0.3 V applied potential over collagen-1 concentrations 5.0 fg/mL to 200 ng/mL compared with the control in PBS solution using Device 2. Inserts are the enlarged view of the profiles at low and high levels, respectively. All curves oscillating at the AC JJ were observed. FIG. 24B depicts the linear regression calibration curve of current density vs. collagen-1 concentrations over the linear range of 5.0 fg/mL to 100 ng/mL (6 levels) with the regression equation y=0.46+0.094x, r=0.997, Sy/x=0.299, p<0.0001. FIG. 24C depicts Device 2's exponential current increase pattern as the collagen-1 concentration increases, the curve is over 5.0 fg/mL to 200 ng/mL (9 levels) with a Detection of Limits (DOL) of 0.43 pg/mL/cm$^2$ (14 fg/mL for this sensor) with a relative percent of sum of squares pure error (RSSPE) of 0.05% at the high end and 0.5% at the low end, respectively.

Point Accuracy and Imprecision. Point accuracy and imprecision was studied through the recovery experiments using spiked human fresh finger capillary blood (CPWB) serum specimens as controls spiked with 2 levels of collagen concentrations over 2.5 pg/mL to 166 ng/mL, and we compared the measured results with the calibration curve after subtraction of the currents from control serum samples. The recovery results were 96.4±3.4% and 97.9±0.73% with the imprecision of 4.9% and 0.8% at 2.5 pg/mL and 166 ng/mL level, respectively by the CA method. Due to the strong wave oscillation occur in both the PBS solution and the finger serum samples, Device 1 and 3 at both the innate and activated states were unable to respond to concentration changes of collagen-1 from 500 fg/mL to 100 ng/mL both in PBS and in human finger serum using the CA method under the fixed potential, respectively.

Example 17

Figure 25B:
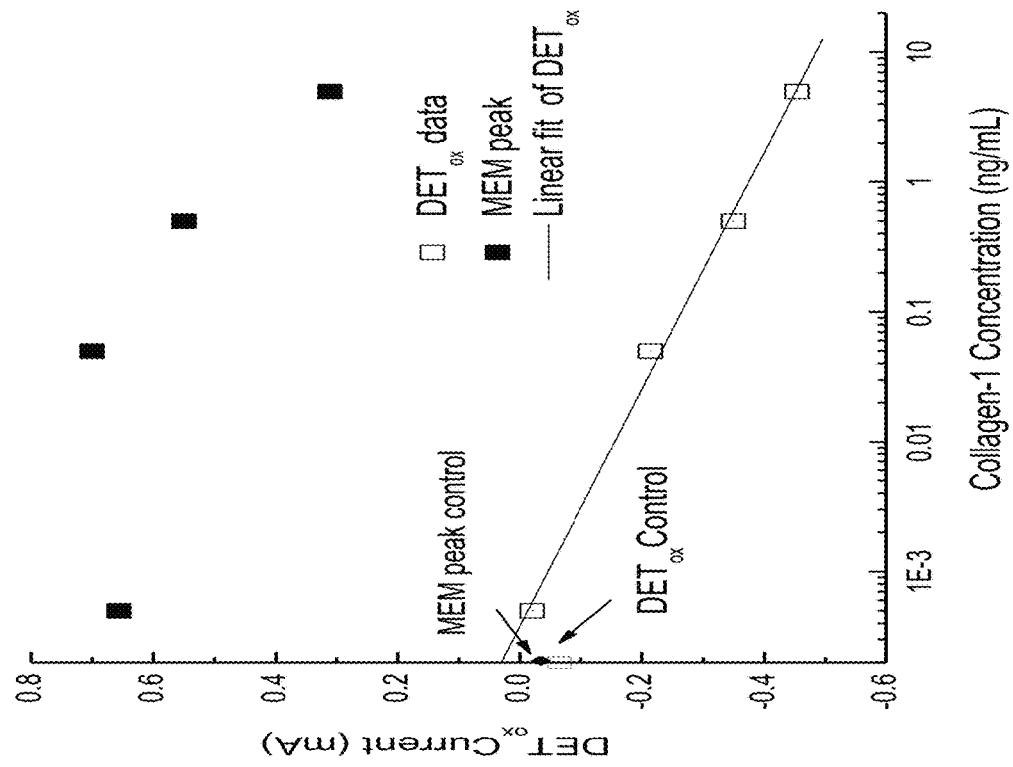
FIG. 25B depicts Device 2's $DET_{ox}$ peak current vs. collagen-1 concentrations in a log scale. The solid squire represents MEM peaks.
Figure 25A:
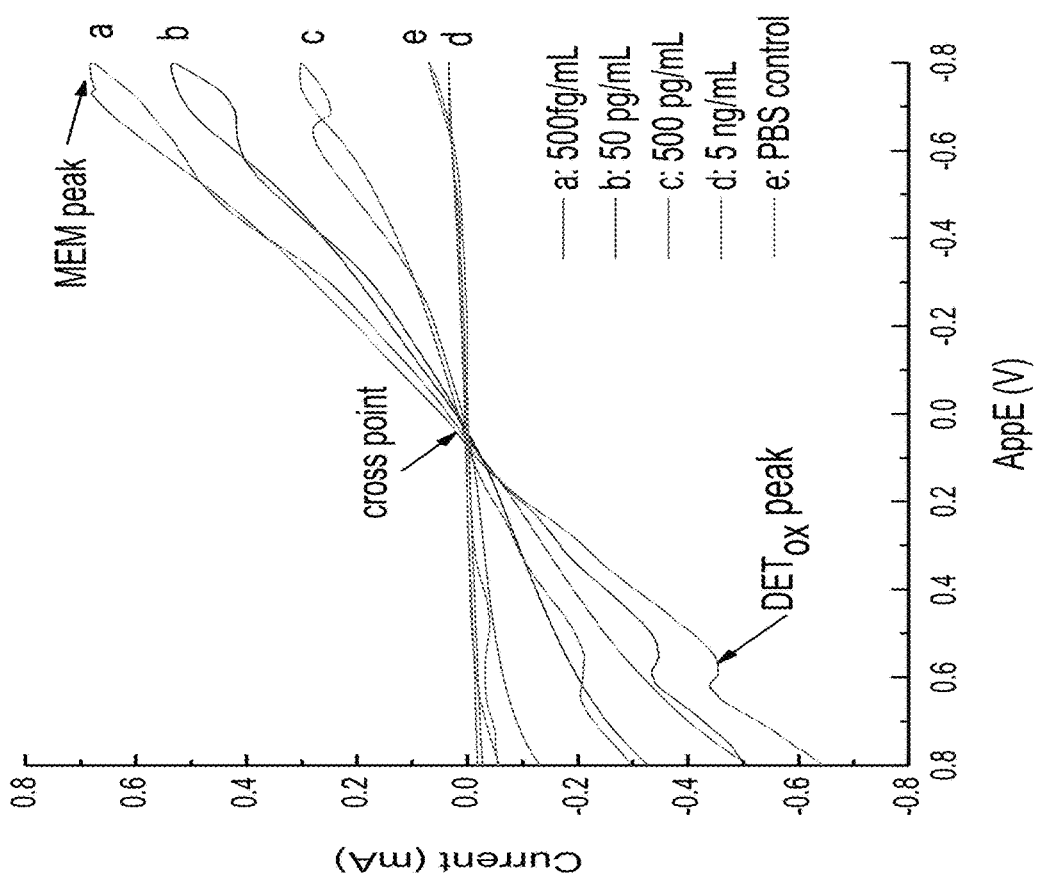
FIG. 25A depicts the i-V curves of the memristive characteristics of Device 2 in PBS in the presence of collagen-1 over 0.5 pg/mL to 5 ng/mL vs. control at 200 Hz scan rate.
Figure 26A:
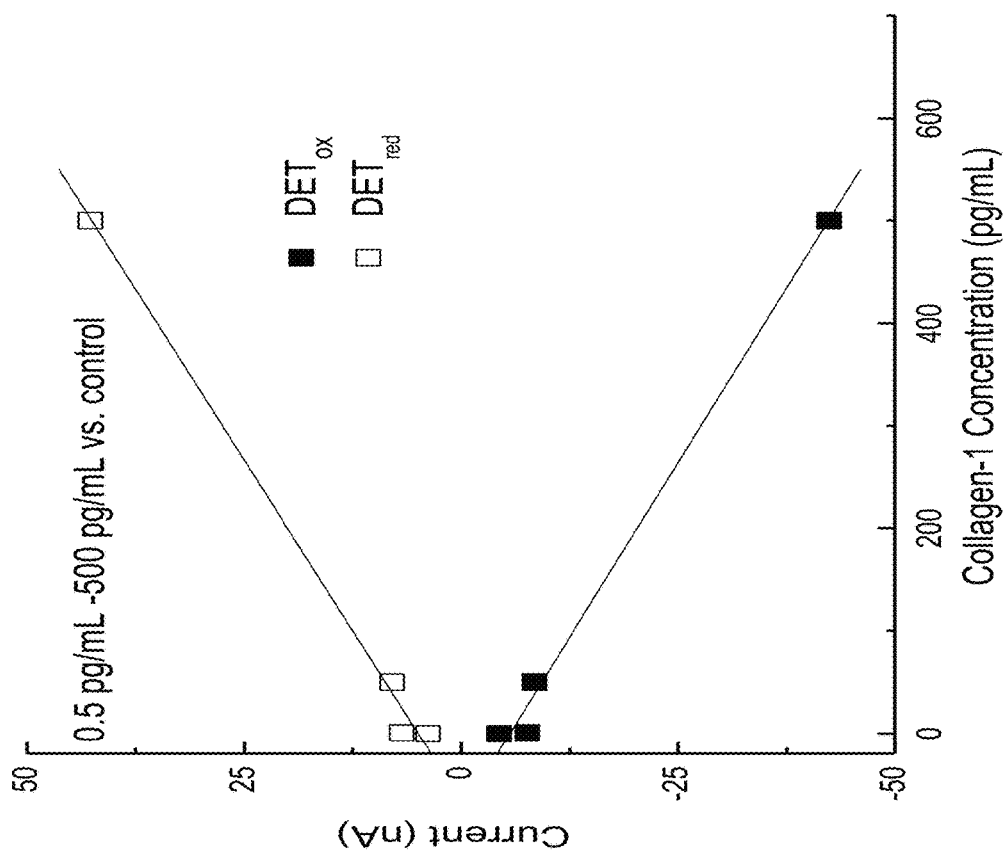
FIG. 26A depicts i-V plots of Device 3 (innate) with or w/o collagen-1 in PBS at 300 Hz.
Figure 26B:
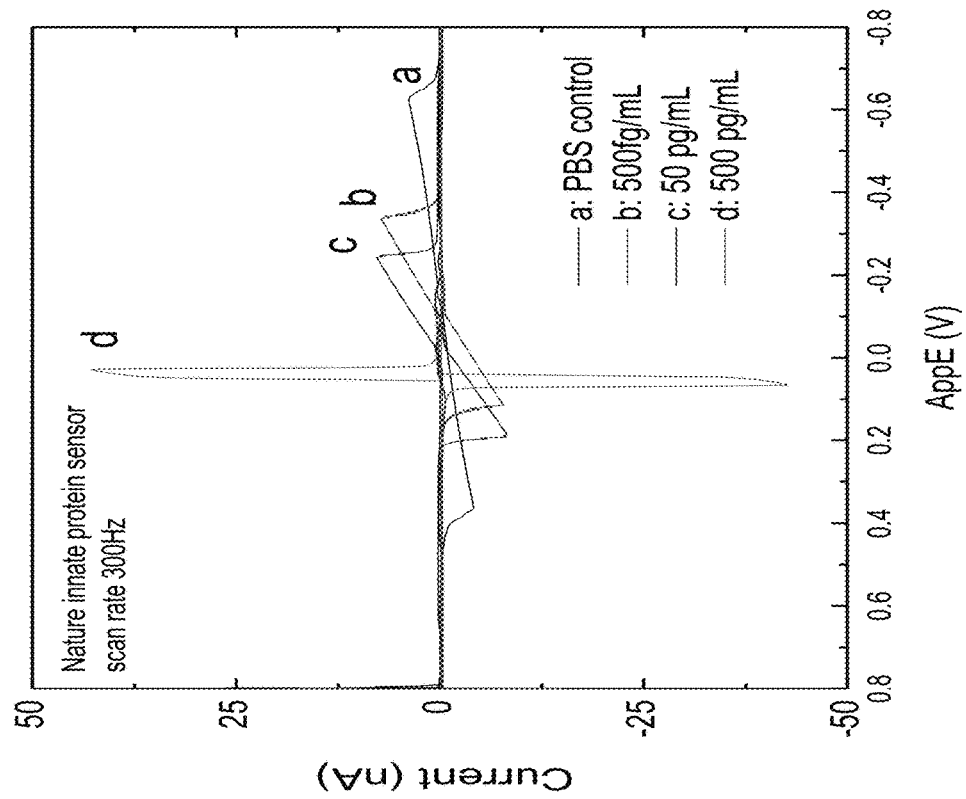
FIG. 26B depicts the linear plots of current vs. collagen-1 concentrations for $DET_{red}$ and $DET_{ox}$ peaks over 0.5 pg/mL to 500 pg/mL, respectively.

Direct Label-Free and Antibody-Free Detection of Protein by the Innate Native Protein MMP-2 Device FIG. 25A depicts the i-V curves of Device 2's direct measurements of protein collagen-1 over 0.5 pg/mL to 5 ng/mL compared with the control in PBS solution at 200 Hz. FIG. 25B depicts an exponential decay relationship between the $DET_{ox}$ peak current and the collagen concentrations in PBS solution in a log scale. Device 2 has 1.2×10$^7$-fold increase in detection sensitivity and testing range compared with Device 3 at an innate state as shown in FIG. 26A in the i-V profiles and FIG. 26B in the calibration curve. However, it was shown in the first time that the native MMP-2 innate Device 3 was able to directly sense the presence of collagen-1 in 0.5 pg/mL to 0.5 ng/mL linearly without denaturing and without labeling, and that is due to the toroidal superlattice structure of the membrane, which stimulates the localized biological zinc atoms to become mobile and causes the Friedel-oscillation with functional groups in collagen-1 and in the polymers.

Example 18

Protein Concentration Change Impacts on Super-Positioning of Quantum States

Figure 27B:
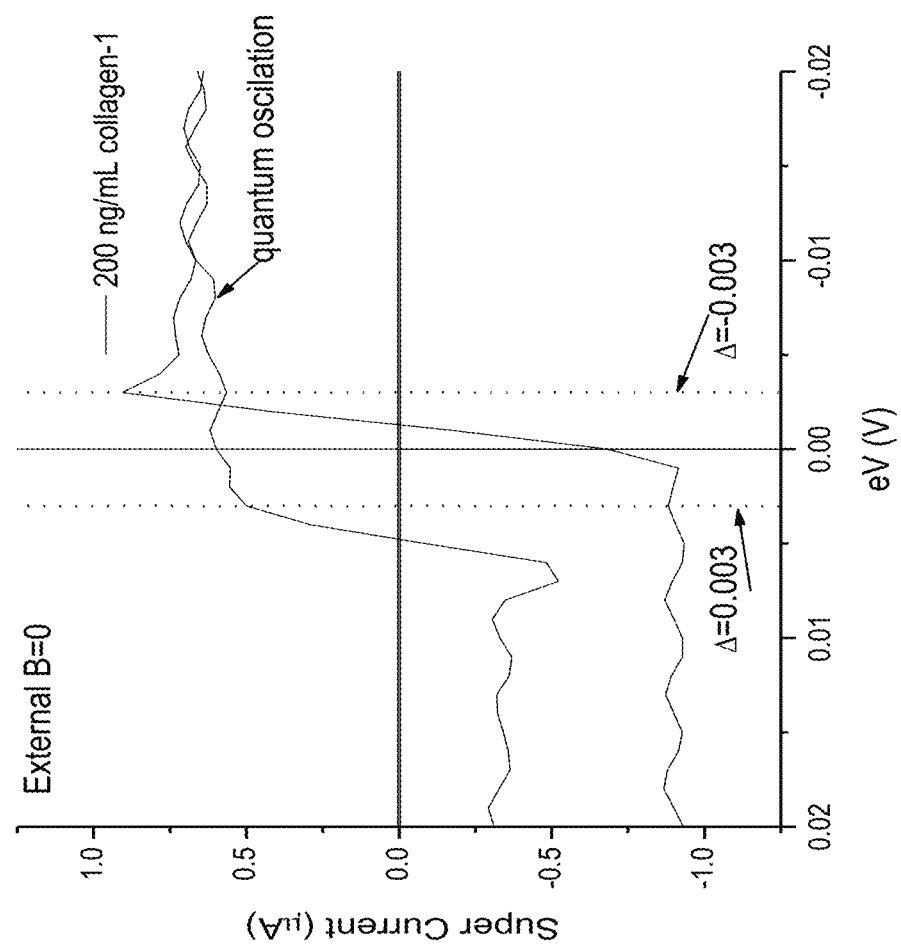
FIG. 27B depicts the 200 ng/mL collagen-1 transformed a memristive device to a superconductive device with zero-bias supercurrent and the $\pm\Delta$ is within the range 3 mV.
Figure 27A:
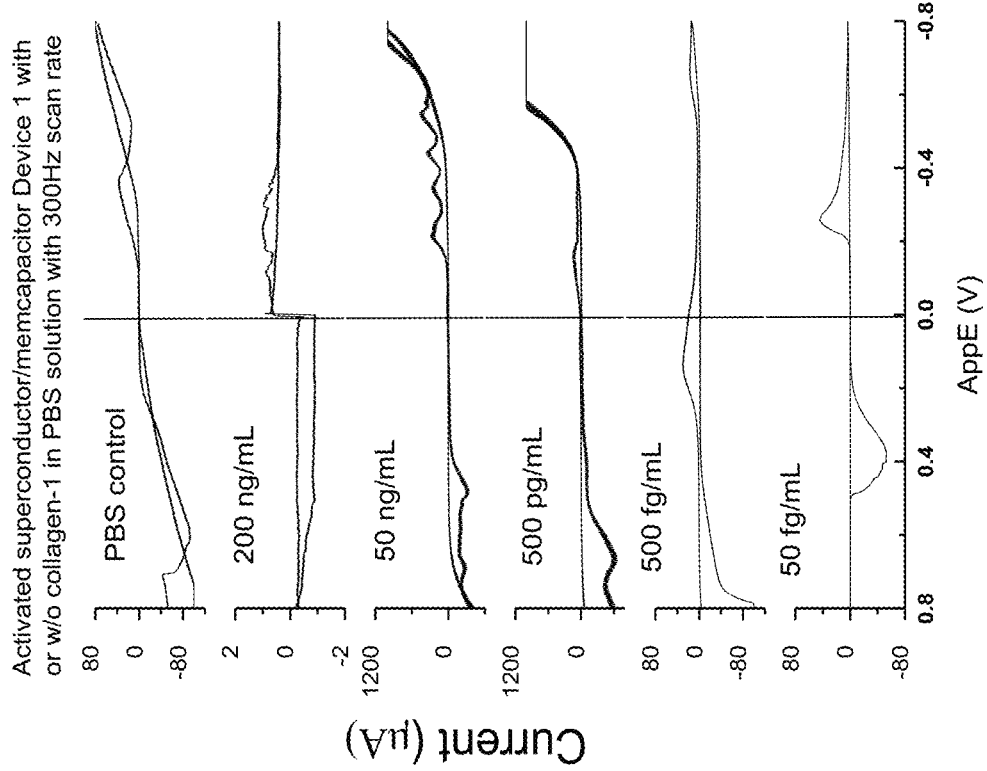
FIG. 27A depicts activated superconductor/memcapacitor Device 1 with or without collagen-1 concentrations over 50 fg/mL to 200 ng/mL in 5 levels in PBS solution compared with the control under 300 Hz scan rate.
Figure 27D:
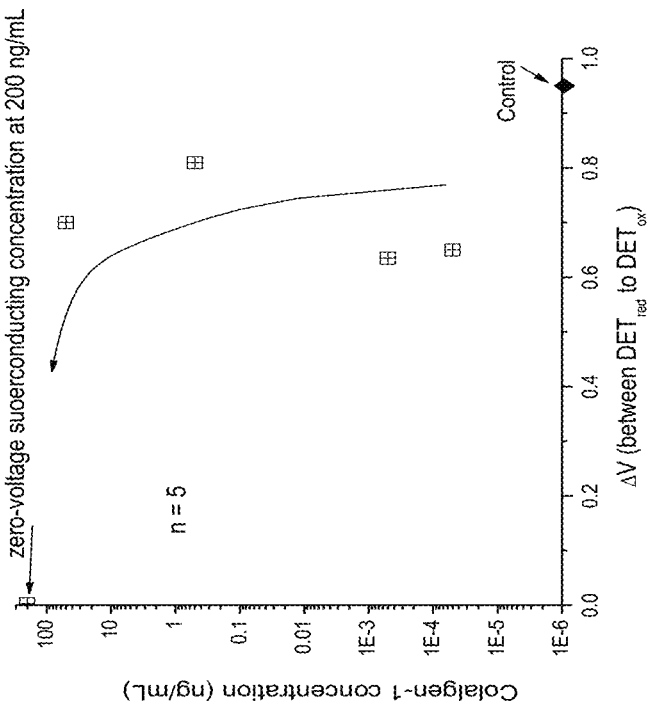
FIG. 27D depicts the trend of collagen-1 reduces the quantum energy gap of the potential difference between $DET_{red}$ and $DET_{ox}$ vs. collagen-1 concentration.
Figure 27C:
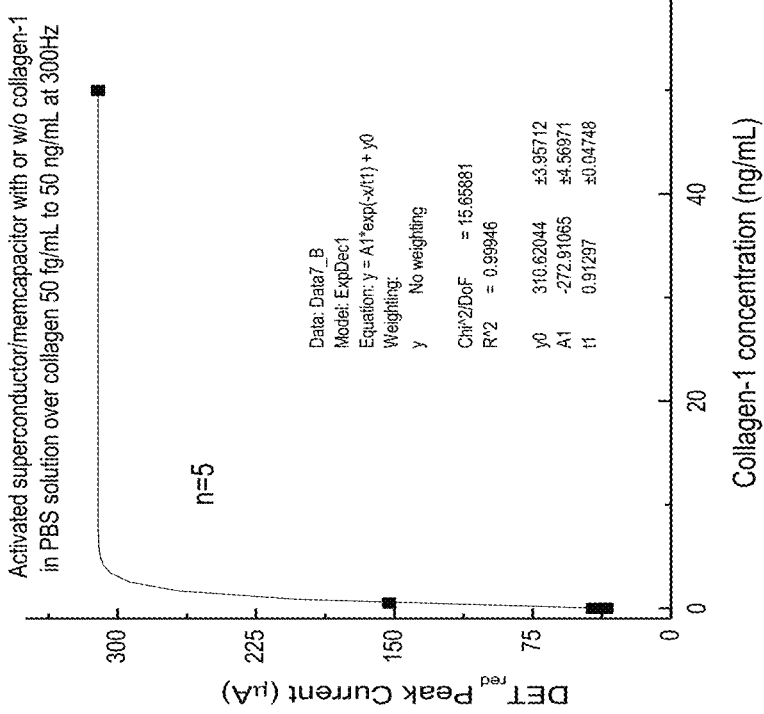
FIG. 27C depicts the exponential increase relationship between the activated Device 1's $DET_{red}$ current and the collagen-1 concentrations between 50 fg/mL to 50 ng/mL.

Protein concentration change impacting on super-positioning of quantum states was studied by comparing of the i-V curves for with or without collagen concentrations at a fixed scan rate. FIG. 27A shows the Activated Device 1 transformed its memristive state to a superconducting state at a higher protein concentration of 200 ng/mL in the PBS buffer solution under 300 Hz scan rate by closing the quantum energy gap between $DET_{red}$ and $DET_{ox}$. FIG. 27A depicts when collagen-1 concentrations lower than 200 ng/mL, covered 4 levels from 5 fg/mL to 50 ng/mL, were no superconductivity, and the memristive curves were shown in several collagen concentrations. FIG. 27B depicts the super-positioning of quantum states happened in the i-V curve among the states (0 V, −1), (0 V, 0) and (0V, +1) at zero-bias potential with 200 ng/mL collagen. Here "+1" means the supercurrent >0, "−1" means the supercurrent <0. It was observed the origin point was inside of the narrow barrier of ±Δ≤3 mV. FIG. 27C depicts the exponential increase relationship between the activated Device 1's $DET_{red}$ current and the collagen-1 concentrations from 50 fg/mL to 50 ng/mL. FIG. 27D depicts the trend of collagen-1 reduces the quantum energy gap of the potential difference between $DET_{red}$ and $DET_{ox}$ vs. collagen-1 concentration.

Example 19

CONCLUSIONS

We demonstrated the quantum superconductive//memristive and the quantum superconductive/memcapacitive devices promoted superconductivity, quantum memristivity, and quantum memcapacity. Device 2's quantum conductance density per superlattice is 3.1×10$^{10}$, 13 and 1.33-fold higher than that of activated Device 3 at 1 Hz, 1 kHz, and 10 kHz, respectively, and it can directly detection of sub fg/mL collagen-1 with higher sensitivity and wider range compared with Device 3 at innate and activated states. We also reported the innate Device 3 can directly sense 0.5 pg/mL to 500 pg/mL collagen-1 without denaturing procedures. The quantum superconductive/memristive technology having external magnetic field-free conditions and performed well at room temperature may find broad applications in supercomputing, artificial intelligence, energy, medical sensing, artificial antibody, and military, various areas in the future.

We demonstrated the innate Device 1 solely depends on the fractional quantum phase change to induce quantum superconductivity/memcapacity in PBS solution, that works superior over Device 2 and 3 for sensing of voltage change in the presence of sub pg/mL collagen-1 to 200 ng/mL with good results of recovery using human serum samples. We also demonstrate the toroidal vortex topological nonconventional superconductive devices with various superlattice structures having the Friedel-oscillation are workable at room temperature without an applied external magnetic field. The devices worked in different media by using collagen-1 as an insulator and as an analyte. Without denaturing of a protein, the biomimetic MMP-2 superconductors offered significant benefits in both, superconducting and sensing, compared with the reference device.

REFERENCES

[1]. J. K. Kular, S. Basu and R. I. Sharma, The extracellular matrix: structure, composition, age-related differences, tools for analysis and applications for tissue engineering, J. Tissue Engineering 5, 1-17, 2014.

[2]. T. Watanabe-Nakayama, M. Itami, N. Kodera et al., High-speed atomic force microscopy reveals strongly polarized movement of clostridial collagenase along collagen fibrils, Scientific Reports, 6:28975, 2016.

[3]. M. F. Najafi, S. Zahri, F. Vahedi et al., Which form of collagen is suitable for nerve cell culture? Naural Regeneration Research, 8(23), 2165-2170, 2013.

[4]. W. Mckleroy, T-H Lee and K. Atahai, Always cleave up mess: targeting collagen degradation to treat tissue fibrosis, Am J Physiol Lung Cell Mol Physiol 304, L709-L721, 2013.

[5]. E. Takai, K. D. Costa, A. Shaheen et al., Osteoblast elastic modulus measured by atomic force microscopy is substrate dependent, Annals of Biomedical Engineering, 33 (7), 963-971, 2005.

[6]. B. H. San, Y. Li, E. B. Tarbet, S. M. Yu, Nanoparticle assembly and gelatin binding mediated by triple helical collagen mimetic peptide, ACS Applied Materials and Interfaces, 8, 19907-19915, 2016.

[7]. E. Seo, K. W. Seo, J -E Gil, Y -R Ha, et. Alo., Biophysiochemical properties of endothelial cells cultured on bio-inspired collagen films, MioMed Central Biotechnology, 14:61, 2014.

[8]. E. T. Chen, J. T. Thornton, S -H. Duh and P. T. Kissinger, Organic Nanobiomimetic Memristive/Memcapacitive Devices Ultrasensitive Direct Detect Matrix Matelloproteinase-2 in Human Serum, Biotech, Biomaterials and Biomedical, TechConnect Briefs, 271-274, 2017.

[9].E. T. Chen, J. T. Thornton, S -H. Duh And P. T. Kissinger, Observation of Fermi Arc Surface States Induced by Organic Memristive/Memcapacitive Devices with a Double-Helical Polarized Single-Wall Nanotube Membrane for Direct Chelating with Matrix Matelloproteinase-2, Sensors and Transducers Journal, 214(7), 69-84, 2017.

[10]. Editors E. Wolf, G. Arnold, M. Gurvitch and J Zasadzinski, Preface, Josephson Junctions, History, Devices, and Applications, Pan Stanford Publishing Pte, Ltd, 2017.

[11]. S. Frolov, Quantum Transport, www.sergeyfrolov.wordpress.com/teaching

[12]. S. Kivelson, Superconductivity and Quantum Mechanics at Micro-Scale, Stanford University. www.youtube.com/watch?v=yx666k2xH8E

[13]. E. Grosfeld And A. Stern, Observing Majorana bound states of Josephson vortices in topological superconductors, PNAS, 108(29), 11810-11814, 2011.

[14]. X. Liu, X. Li, D -L Deng, X -J Liu, and S. Das Sarma, Majorana Spintronics, arXiv, 1602.08093v2, 2016.

[15]. J. Li, T. Neupert, B. A. Bernevig, A. Yazdani, Manipulating Majorana zero modes on atomic rings with an external magnetic field, Nature Communications, 7:10395, 2016.

[16]. www.en.wikipedia.org/Josephson vortex

[17]. J. Salmileto, F. Deppe, M. DiVentra, Quantum memristors with superconducting circuits, Scientific Reposrts, 7:42044, 2017.

[18]. C. Guarcello, P. Solinas, M. DiVentra and F. Giazotto, Solitonic Josephson-based meminductive systems, arXiv: 1610.06807v1, 2016.

[19]. M. Ternes, M. Pivetta, F. Patthey, and W -D Schneider, Creation, electronic properties, disorder, and melting of two-dimensional surface-state-mediated adatom, Progress in Surface Science 85, 1-27, 2010.

[20]. E. T. Chen and H. L. Pardue, Analytical applications of catalytic properties of modified cyclodextrins, Anal. Chem, 65(19), 2583-2587, 1993.

[21]. S. Davari, S. A. Talaei, H. Alaei, M. Salami, Probiotics treatment improves diabetes induced impairment of synaptic activity and cognitive function: behavioral and electrophysiological proofs for microbiom-gut-brain axis, Neuroscience, 240, 287-296, 2013.

[22]. M. D Pickett, G. Medeiros-Ribeiro and R. S Williams, A scalable neuristor built with Mott memristors, Nature Materials, 2013, 12, 114-117.

[23]. M. Sufi and B. Desolvo, Advances in neuomorphic memristor science and applications, Editors R. Kozma, R E Pino, G E Pazienza, Springer publisher, 4, 2012.

[24]. M. D Ventra, Y. V Pershin, On the physical properties of memristive, memcapacitive, and meminductive systems, Nanotechnology 24, 255201, 2013.

[25] E. T. Chen, J. T. Thornton and Jr C. Mulchi, Mapping Circular Current for a Single Brain Cancer Cell's Spatial-Temporal Orientations Based on a Memristor/Memcapacitor, Sensors & Transducers, 183(12), 72-83, 2014.

[26]. S -H. Duh, J. Thornton, P. T. Kissinger and E. T. Chen, Nanobiomimetic memristor/memcapacitor devices used for direct and reagent-less detection of sub pM acetyl coenzyme A in milks, Sensors, Diagnostics & Imaging, TechConnect Briefs, 4, 136-139, 2016.

[27]. S -H. Duh, J. Thornton, P. T. Kissinger and E. T. Chen, Human Milk Shows Immunological Advantages Over Organic Milk Samples For Infants In the Presence of Lipopolysaccharide (LPS) in 3D Energy Maps Using an Organic Nanobiomimetic Memristor/Memcapacitor, Sensors and Transducers Journal, 203(8), 57-68, 2016.

[28]. E. T. Chen, J. Thornton, P. T. Kissinger and S -H. Duh, The Advantages of Human Milk Recognize the Spatiotemporal Locations of Toxins and Intelligently Bypass Them by Forming a Hummingbird-Like Hovering Neural Network Circuitry Based on an Organic Biomimetic Choline Acetyltransferase Memristor/Memcapacitor Prosthesis, Sensors and Transducers Journal, 203(8), 69-83, 2016.

[29]. E. T. Chen, Nanostructured Biomimetic Sensing And Energy Storage: Organic Memristor/Memcapacitors was published in the book of *Dekker Encyclopedia of Nanoscience and Nanotechnology, Third Edition*, DOI: 10.1081/E-ENN3-120054061, Jan. 18, 2017. www.crc-netbase.com

[30] J. E. Redman, Solution, surface and solid state assembly of porphyrins, University of Cambridge, 2000.

[31]. R. V. Slone and J. T. Hupp, Synthesis, charaxterization, and prelimanry host-guest binding studies of porphyrinic molecular squares featuring fac-tricarbonylrhenium(1) chloro corners, Inorg Chem 36(24), 5422-5672, 1997.

[32]. M. S. Liao, Electronic structure and bonding in metal porphyrins, metal=Fe, Co, Ni, Cu, Zn, Utah State University publication, 2002.

[33]. A. E. Power, Slow-wave sleep, acetylcholine, and memory consolidation, PNAS, 101, 7, 1795-1796, 2004.

[34]. Slow-wave sleep, www.wikipedia.org

[35]. Fractional Josephson vertice.wikipedia.com

[36]. X. Liu, X. Li, D -L Deng et al., Majorana spintronics, arXiv:1602.08093v2, 2016.

[37]. J. Chen, P. Yu, J. Stenger et al., Experimental phase diagram of zero-bias conductance peaks in superconductor/semiconductor nanowire devices, Science Advances, 3, e1701476, 2017.

FOLLOWING IS THE DETAILED
DESCRIPTION OF THE PRESENT CIP
INVENTION

Example 1

Fabrication of the Superconductive/Energy Sensing Device Having Superlattice Toroidal Structures Sensor 1's membrane was fabricated by deposition of a mixture solution comprised of HSP60, triacetyl-β-cyclodextrin (TCD), polyethylene glycol diglycidyl ether (PEG), and poly (4-vinyl pyridine) (PVP) with appropriate propositions on the surface of gold chips at 37° C. for 72 hours. The procedures used for fabrication of the innate HSP60/MMP-2 self-assembled membrane was followed by published literature [15].

The device 2 for the innate HSP60/MMP-2 device was prepared with two steps: the first step was to form an MMP-2 polymer layer by a self-assembling method with compositions of the innate MMP-2, triacetyl-β-cyclodextrin (TCD), polyethylene glycol diglycidyl ether (PEG) and poly (4-vinylpyridine) (PVP) with appropriate propositions deposited on the surface of a 50 nm thickness gold chip having 16 channel plate, while each channel has three pure gold electrodes flatly layout sitting on a flexible non-conductive plastic plate with the plastic plat thickness less than 500 μm. The center working electrode was used for the polymer mixture to be deposited onto it at 37° C. for 96 hours after that followed the wash and dry procedures [15]. The auxiliary electrode has a circuit length 2.5-times longer than that of the working electrode's circuit length. The reference electrode is gold. The second layer was fabricated as same procedures for sensor 1. The MMP-2 was purchased from Ana Spec (Freemont, CA).

Example 2

Characterization of the SAM Membranes

Figure 28E:
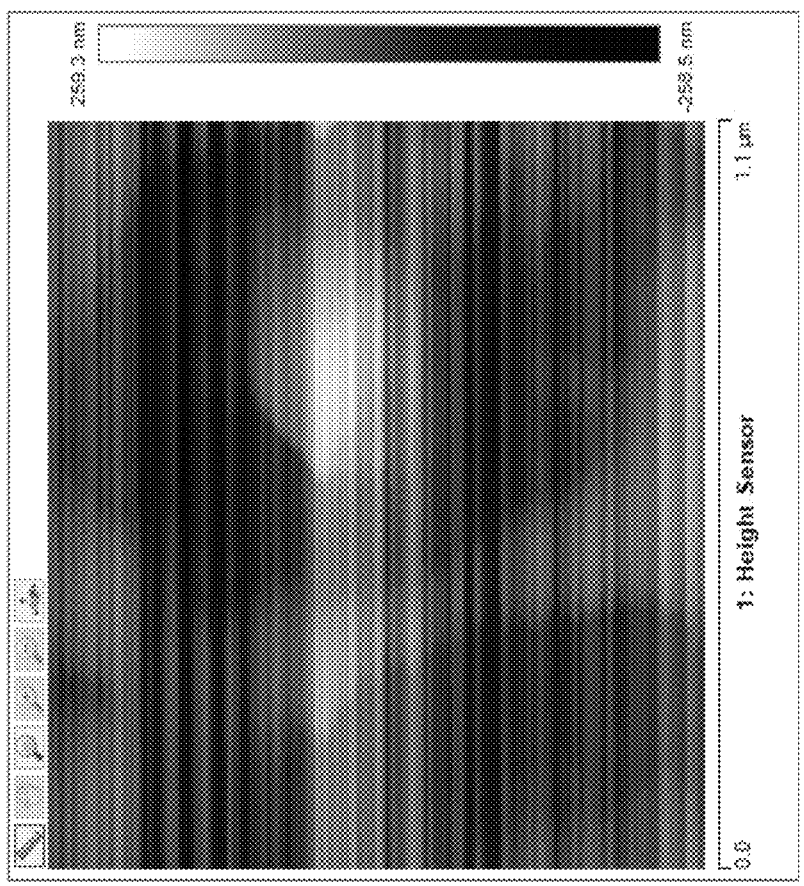
Figure 28F:
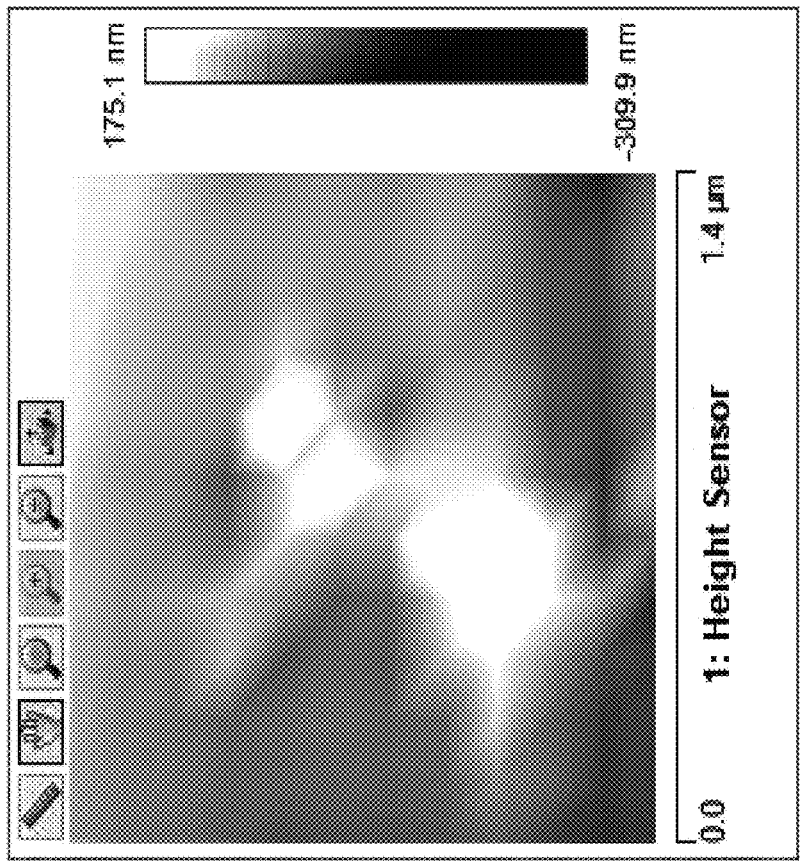

The morphology of the AU/SAM was characterized using an Atomic Force Microscope (AFM) (model Dimension Edge AFM, Bruker, MA). Data collected in Tapping Mode using silicon probes with 5-10 nm tip radius and ~300 kHz resonance frequency (Probe mode TESPA-V2, Bruker, MA). FIGS. 28A and 28B refer to 3D AFM images of the multiple-layered SAMs of Sensor 1. FIG. 28B has many vertically oriented nano-pillars on top of horizontally oriented well-ordered high and low-lay densified nanotubes. FIG. 28C reveals a cluster of 37 two-heptametrical rings made up tetradecamer oriented chaperone HSP60, and a 37 cluster of U-shape HSP60 subunit was observed on top of the layered nanotube surface. The ratio of width/length of the HSP cluster from our images is 0.90 vs. 0.88 reported from the literature, our AFM results has a good agreement vs. cryo-EM of 98% [23-25]. FIG. 28D reveals the HSP60 cluster's structure with nanopores of the HSP with double-truncated donuts in shape or U-shape subunits on the top of the orderly nanotube array membrane. FIG. 28E shows another cluster of HSP60 in a 1.4×1.4 μm² area, it emitted golden light beams from the HSP clusters. FIG. 28F shows the nanotube density differently oriented on the top-hill area and on the low-lay canyon area of the 2D AFM image.

Example 3

Evaluation of the Friedel-Oscillation in the Superlattice Membranes

Figure 29B:
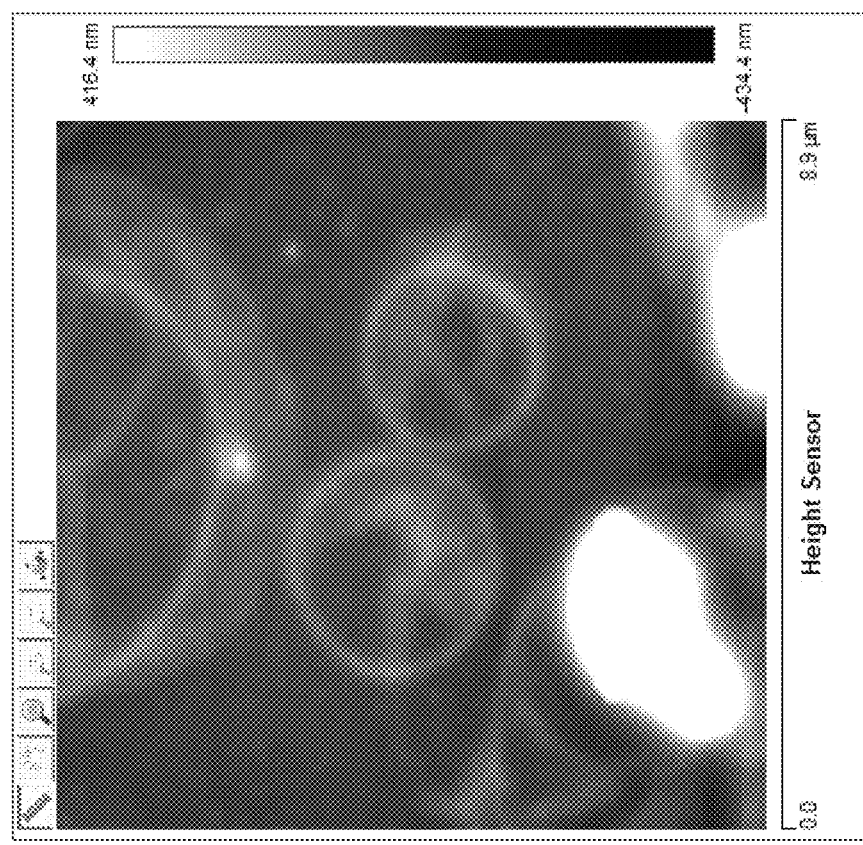
FIG. 29B depicts the 2D AFM image in a larger area.
Figure 29:
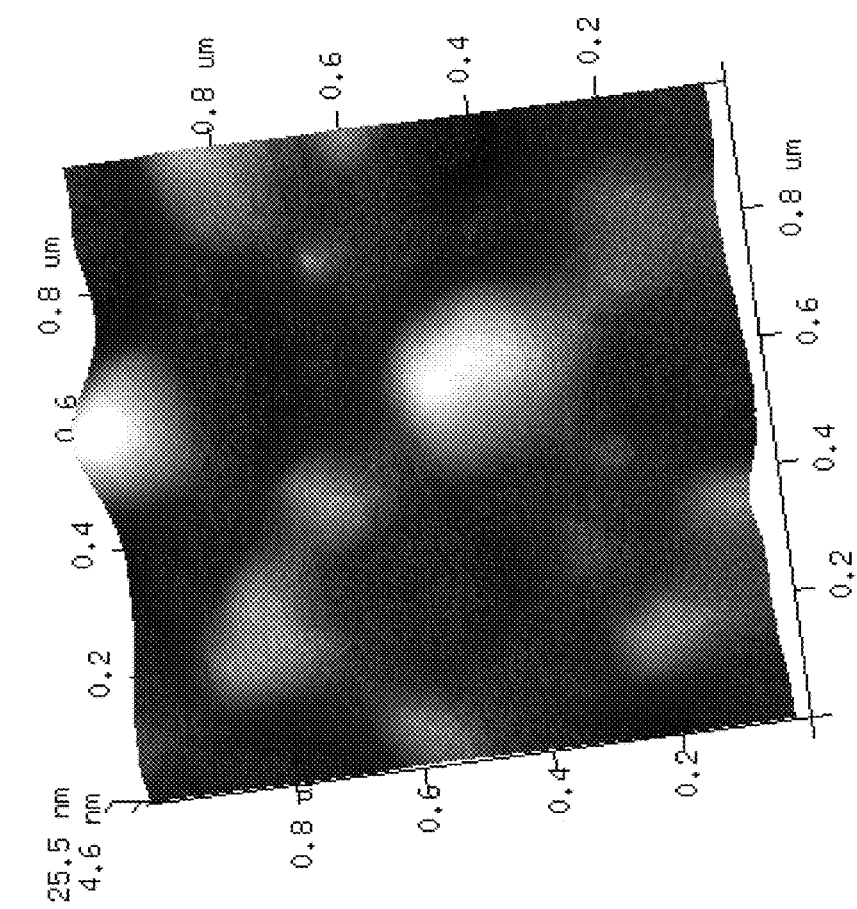
FIG. 29A depicts the 3D AFM image of the MMP-2 toroidal array superlattice membrane as the first layer in Sensor 2.
FIG. 29C depicts the second layer of tower structure HSP60 AFM image multiple-enzyme network membrane which is on top of the first layer of MMP-2.
FIG. 29D depicts the toroidal "diamond ring" structure in detail.
FIG. 29E depicts another AFM image from a different area for the tower glow with Cooper-pair moving with the Friedel-oscillation compared with the background superlattice of toroidal rings.
FIG. 29F depicts the 2D AFM image of a HSP60 subunit as a donut at the low z-value 70 nm.
FIG. 29G depicts the 3D AFM image of the tall nanometer size "Tesla Tower" with height between 500-700 nm.
Figures 29C, 29D:
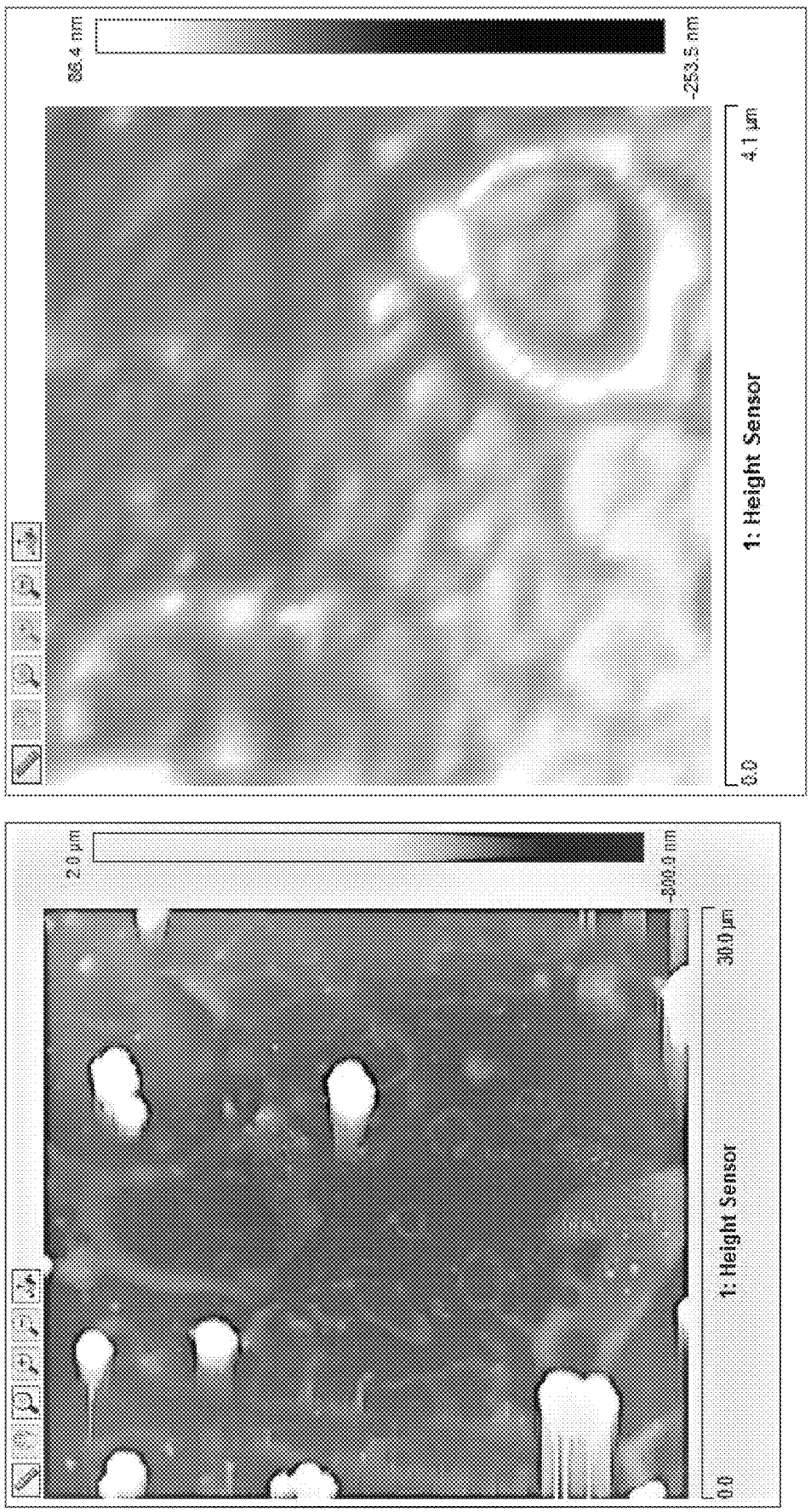
Figure 29F:
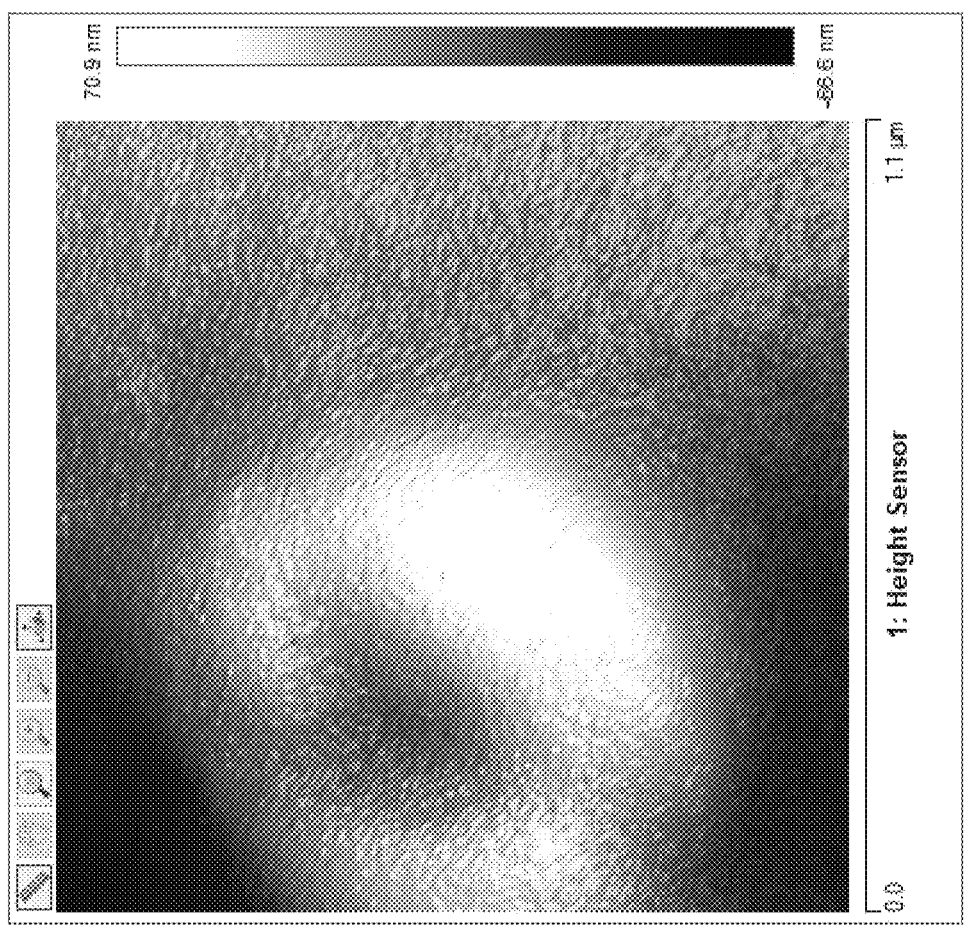
Figure 29E:
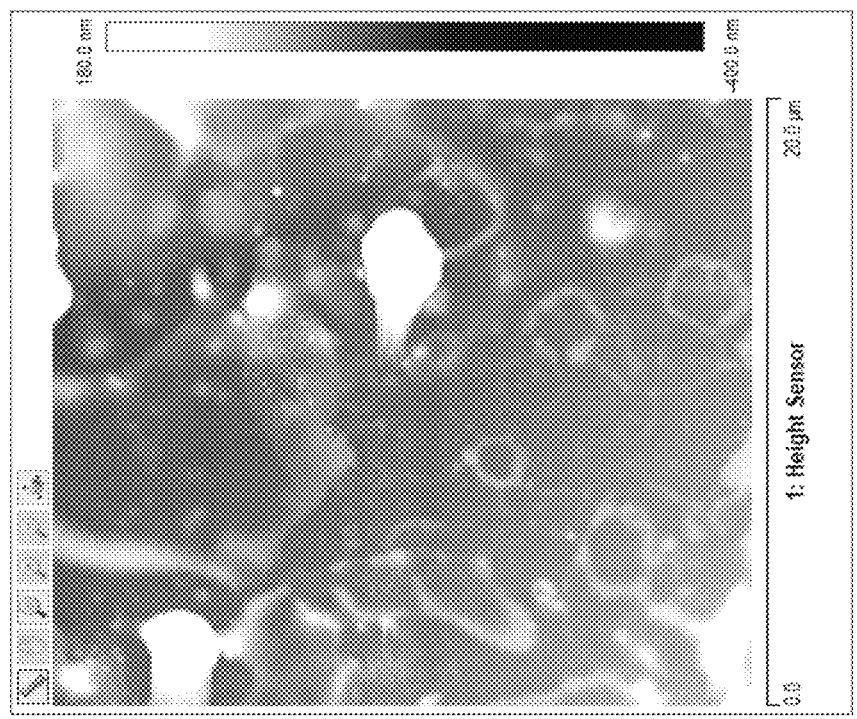
Figure 29G:
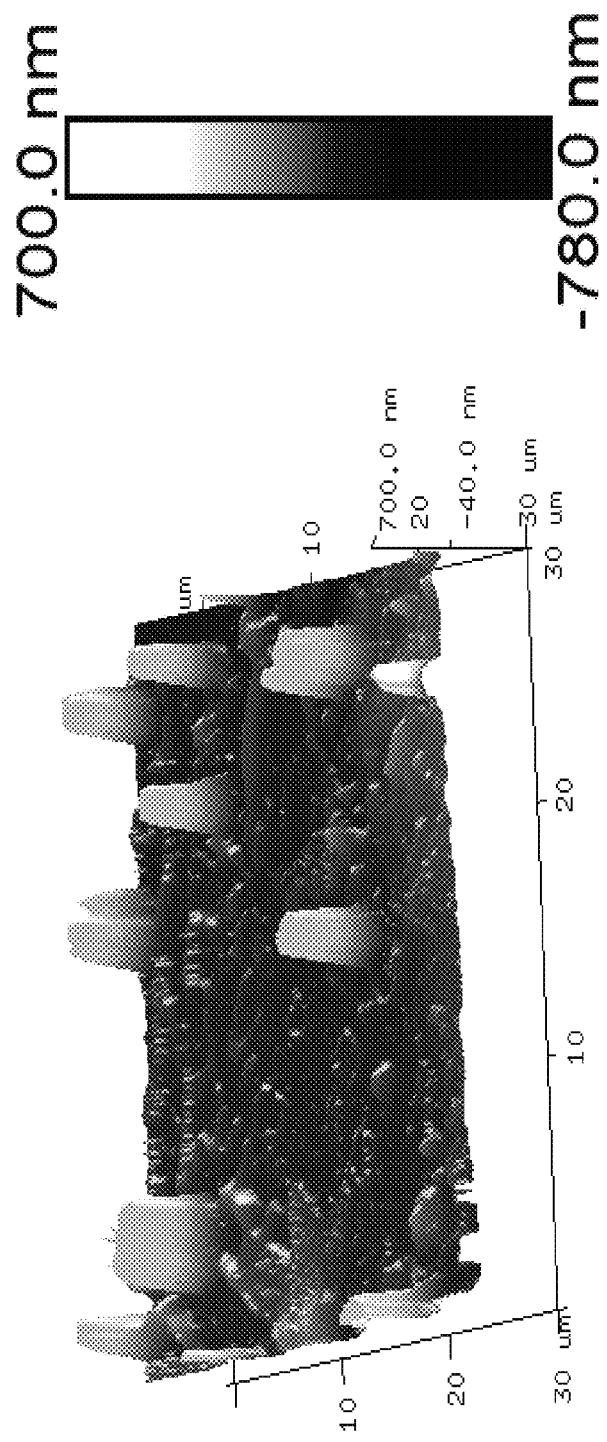

Friedel-oscillation is a phenomenon of long-range indirect interactions between electrons on a superlattice surface by metal oxide materials [16]. Our group has observed strong Friedel-oscillation events in AFM images based on mono- or multiple-layered organo-metallic materials on SAM surfaces [17-22]. FIG. 29A was with the cysteine "On" in its innate state, and we observed the Friedel-oscillation in the 3D AFM image with an electronic cloud surrounded on the zinc atoms of the toroidal array superlattice. FIG. 29B shows the AFM image having large circulars with zinc created a Josephson junction superconducting qubit device. FIG. 29C depicts an AFM image of the multiple-enzyme network membrane with multiple-cluster high tower structure as "Tesla Tower" having the tower diameters between 500 nm to 2.4 μm, and the towers' height is about 500 nm. The strong Friedel-oscillation from Cooper-pair electron cloud due to the MMP-2 . . . HSP60 networking alignment was observed. We observed many MMP-2 formed toroidal rings with some of them have zinc atoms on top. FIG. 29D depicts such a perfect "wedding ring" with zinc ions mobile from the bottom layer (z value 25.5 nm) to the second layer (z value 86.4 nm) sparkling. Many HSP60's fingerprint structure looks like two-end cut of a pineapple observed along with subunits on the superlattice flat surface. FIG. 29E depicts another AFM image from a different area for the tower glow with Cooper-pair moving with the Friedel-oscillation compared with the background superlattice of toroidal rings. FIG. 29F depicts the 2D AFM image of a HSP60 subunit as a donut at the low z-value 70 nm. FIG. 29G depicts the 3D AFM image of the tall nanometer size "Tesla Tower" with height between 500-700 nm.

Figure 30A:
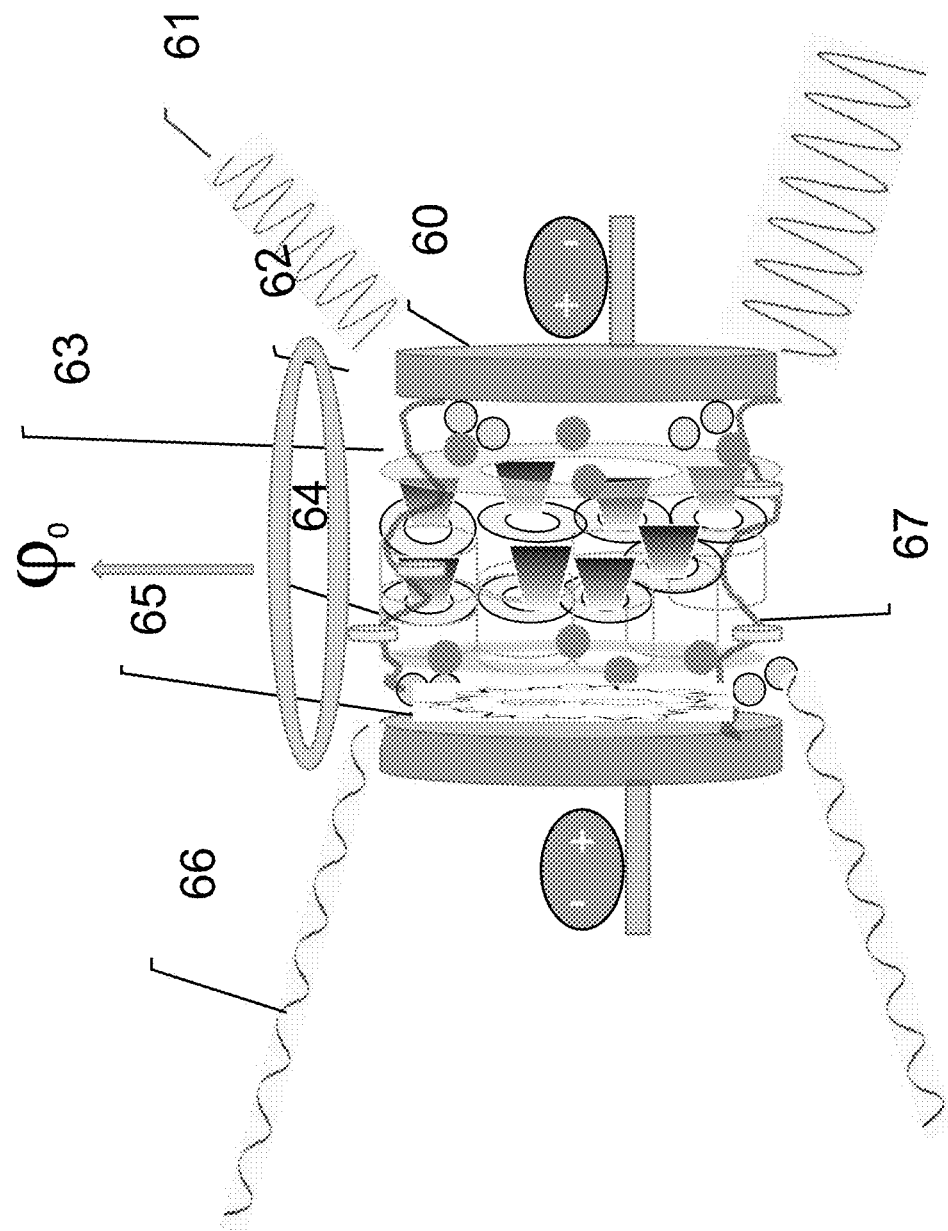
FIG. 30A shows an art model for Device 2 of the superconductive/energy sensing device of HSP60/MMP-2 moonlighting-network in a side view of the Josephson Junction. "60" is the electrode; "61" is the amplified wave after the Cooper pair went through the multiple superconductor-Insulator (the mobile zinc ions from MMP-2)-superconductor (SIS) layers at a higher frequency. "62" refers to the Cooper pair; "63" refers to the circular current flow in a positive direction with the zinc atoms as the brown balls; "64" refers to the HSP6's double-truncated donut cavity array matrix alignment with each other produced the eternal superconducting current in the blue circle having induced a $\varphi_0$, single flux quantum by means of zinc ions bridged from the MMP-2, that a non-ferromagnetic field is produced; "65" is the nano-island membrane on the gold electrode; "66" is the wave of cooper pair electrons after passing through the nano-island membrane; Notice there is an air barrier between the membrane and the array of HSP60 matrix. "67" refers to the PEG . . . PVP's N-terminal chain.

FIG. 30A shows an art model for Device 2 of the superconductive/energy sensing device of the HSP60/MMP-2 moonlighting-network in a side view of the Josephson Junction (JJ). "60" is the electrode; "61" is the amplified wave after the Cooper pair went through the multiple superconductor-JJ (the mobile zinc ions from MMP-2)-superconductor (SJJS) layers at a higher frequency. "62" refers to the Cooper pair; "63" refers to the circular current flow in a positive direction with the zinc atoms as the brown balls; "64" refers to the HSP6's double-truncated donut cavity array matrix alignment with each other produced the eternal superconducting current in the blue circle having induced a $\varphi_0$, single flux quantum by means of zinc ions bridged from the MMP-2, that a non-ferromagnetic field is produced; "65" is the nano-island membrane on the gold electrode; "66" is the wave of cooper pair electrons after passing through the nano-island membrane; Notice there is an air barrier between the membrane and the array of HSP60 matrix. "67" refers to the PEG . . . PVP's N-terminal chain.

Figure 30B:
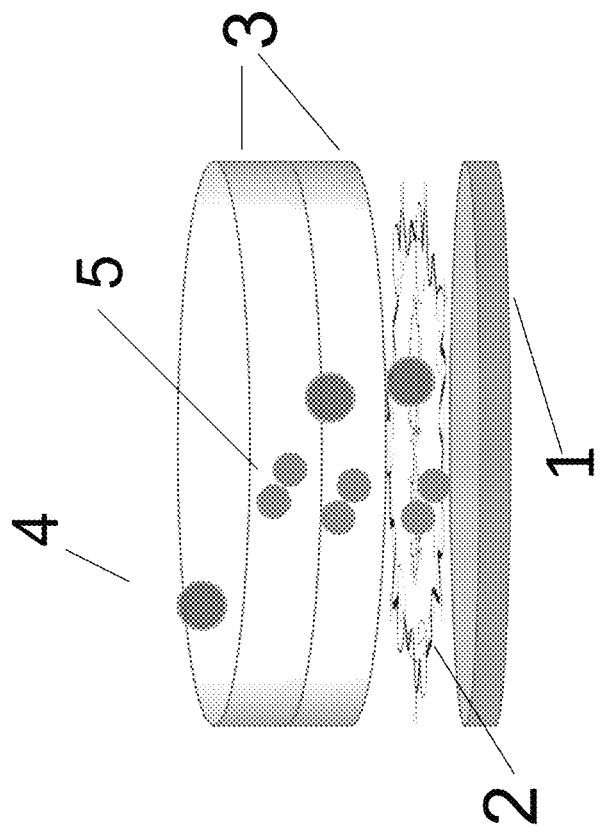
FIG. 30B depicts the detailed art model of the HSP60/MMP-2 with "1" refers to the gold electrode, "2" refers to the MMP-2 toroidal structure comprising of two small toroidal circuits in the center with zinc ions serve as the JJ's "insulator", "3" reefs to the two pieces of HSP60's truncated double-donuts, "4" refers to the mobile zinc ions from MMP-2 up to the HSP cavity, promoting the long range superconducting current, and "5" refers to the Cooper pair electrons.

FIG. 30B depicts the detailed art model of the HSP60/MMP-2 with "1" refers to the gold electrode, "2" refers to the MMP-2 toroidal structure comprising of two small toroidal circuits in the center with zinc ions serve as the JJ's "insulator", "3" reefs to the two pieces of HSP60's truncated double-donuts, "4" refers to the mobile zinc ions from MMP-2 up to the HSP cavity, promoting the long range superconducting current, and "5" refers to the Cooper pair electrons. We conclude that the HSP/MMP device 2 may have superconductive characteristics than that of HSP device 1, due to the observation of the Friedel-oscillation.

Example 4

Evaluation of the Superconductivity and Memristivity

The hallmarks of the JJ characteristics are (1) at a DC voltage=0, $$I_s = I_c \sin(\Delta\varphi) \tag{1}$$

$I_s$ is the supercurrent, $I_c$ is critical current, $\Delta\varphi$ is the phase difference between the waves of two superconductors appears at the DC Josephson junction; (2) at a finite DC voltage, the phase change of the superconducting wave vs. time caused oscillating at the AC Josephson Junction, and is proportional to $2eV_{DC}$, i.e., $$\partial \varphi / \partial t \propto 2eV_{DC} \quad (2)[26\text{-}28]$$

The Josephson junction energy was from the Cooper pair, the magnetic energy was from the inductivity of the circular vortex, and the charge energy was from the SIS quantum capacitor-like device [29]. The vortex suppression of the super current effect also was considered in the equation. However, there was no further analysis of how each component energy contributes to the system superconductivity from the experimental data. Cosmic's group reported seeing the vortex in a Josephson array based on a fractional Josephson Effect in the vortex lattice [30]. The Hamiltonian of the Josephson Junction Array (JJA) was given in the combinations of the first part of charging energy obtained from all arrays and the second part of the Josephson Effect energy [30]. Still, no reports were given on how the energies impacted on one another in their experiment. Inspired by their experimental works, our attempt was, by using the 3D dynamic map method, to further seek a method to elucidate the reactions between the component energies to the superconductivity of the vortex array system at room temperature without external magnetic field applied. Our experimental data were shown on the i-V curves and the AFM structure of the superlattice array. The modified Sine-Gordon system energy for our d-wave vortex array is:

$$E^n_{JJA} = (1/2) C_i^{-1} (Q - en_{1...1})^2 \quad (3)$$

$$E^n_L = (1/2) \mu_0 N^2_{n=1..i} \cdot A \cdot L^{-1}_{n=1..i} \cdot I^2_{n=1..i} \quad (4)$$

where $E^n_{JJA}$ is the charge energy of Josephson Junction arrays at n=1 . . . i; Q is the charge, C is the total capacitance at n=1 . . . i, en is the n quantum particles at 1 . . . i data point with an energy periodic in h/e for Josephson effect for d-wave [31]; $E^n_L$ is the Inductive energy induced by the circular toroidal array. N is the turning number around the toroidal porous at n=1 . . . i, A is the cross-sectional area of the porous, L is the length of the wending, $\mu_0$ to is the magnetic permiability constant in free space; I is current. The toroidal arrays are in series connected. Recent publication regarding our FFTJJ mmultiple-variable study results in 3D dynamic maps was presented in the literature [32].

Figure 31B:
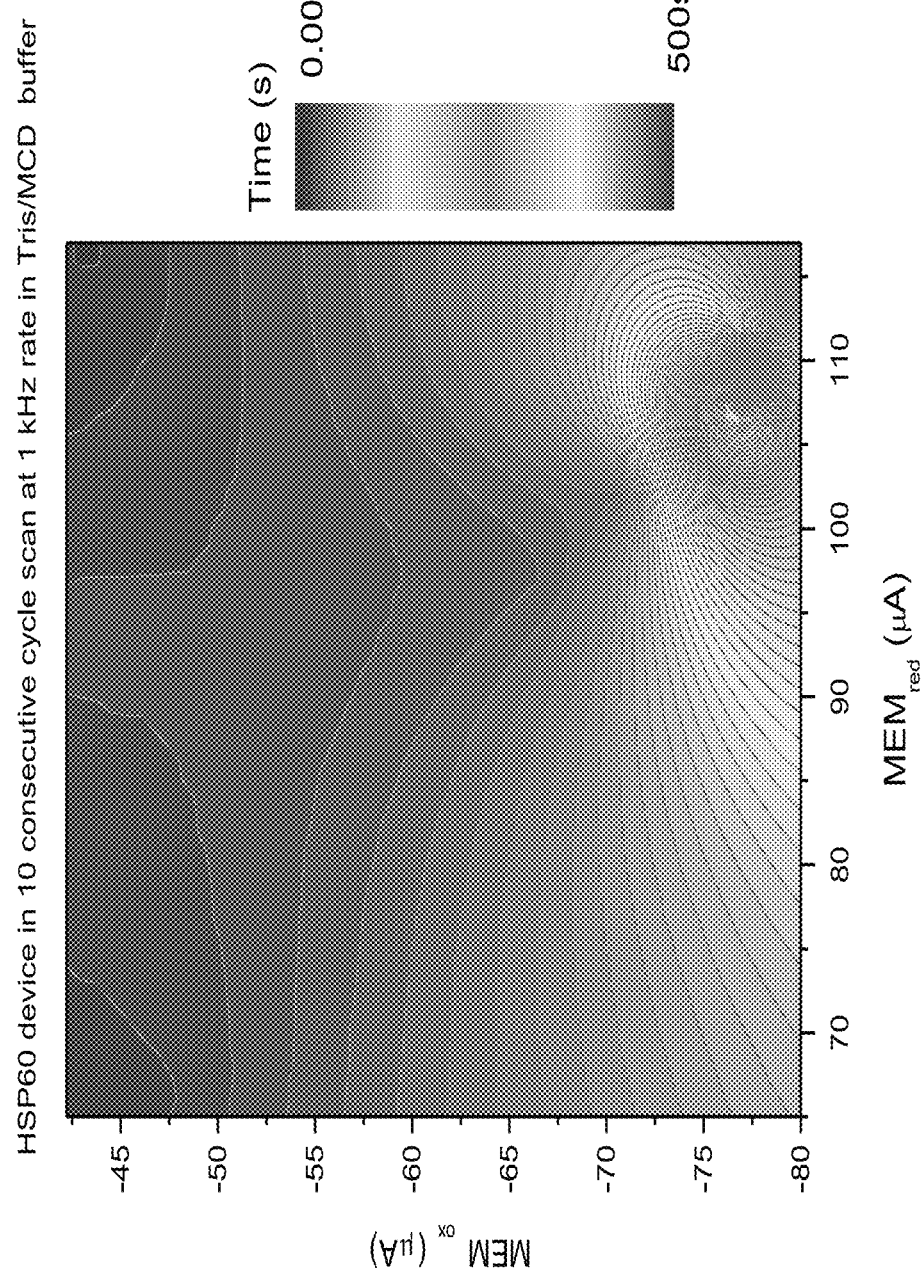
FIG. 31B depicts the contour map between the current of $MEM_{red}$ and current of $MEM_{ox}$ peak intensity vs. time of 10 consecutive scan at 1 kHz in the buffer with the sensor 1. It showed the highest correlation between the variables is at the higher scan cycles.

Memristors are devices made of nanolayers that can mimic neuronal synapses with a characteristic of a hysteresis loop in the i-V curve [33-37]. The memristor HSP Sensor 1's hysteretic i-V profiles measured by the CV method are presented in FIG. 31A as control shown in scan rate 20 Hz, 200 Hz, and 1 kHz with the cross-point at zero-bias having zero current, except 10 kHz and 20 kHz lost the memristive. At 20 Hz, the i-V curve shown Aβ alone having two significant oxidative $DET_{ox}$ peaks at 189 mV and 465 mV, but after 40 µg/mL MOX applied in the 250 ng/mL Aβ solution, no $DET_{ox}$ peaks were observed, indicating MOX had impaired HSP60's function. At 1 kHz scan rate for 10 consecutive cycles, the $DET_{ox}$ and $DET_{red}$ peak intensity are the highest at the first scan cycle, it reduced by 30% at the $5^{th}$ cycle (data not show). In contrast, the $MEM_{red}$ and $MEM_{ox}$ peak intensity showed a "V" shape at the $5^{th}$ cycle, the lowest, then at the last cycles, the highest, indicates time increases the polarity by memristivity than that of the DET signaling in FIG. 31B, hence the HSP nanopillar vertically oriented on the top of the orderly nanotubes covered of the membrane played a role for the device's function.

Figure 32:
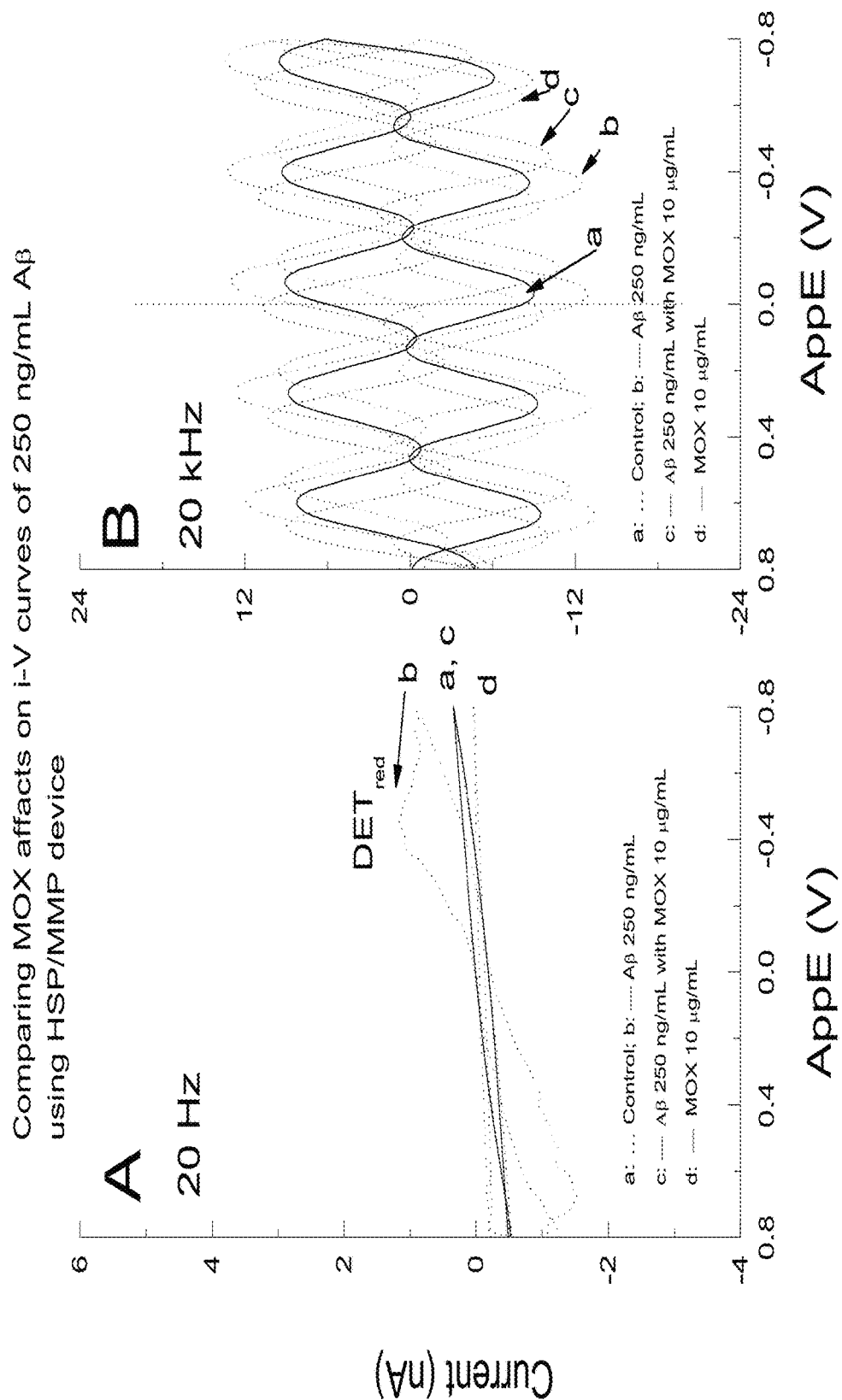
FIG. 32 depicts MOX affecting i-V curves of Aβ at 20 Hz (Panel A) and 20 kHz (Panel B) compared with controls.

In contrast, the HSP60/MMP-2 Sensor 2 shows no $DET_{ox}$ peaks of Aβ in all scan rates. FIG. 32 Panel A at 20 Hz, a large reduction $DET_{red}$ peak at −438 mV was observed, indicates Sensor 2 transferred Aβ from harmful to be useful. At 20 kHz, superconductivity at zero-bias was observed for with or without Aβ, and with or without MOX in FIG. 32 Panel B. The phase change and super-positioning were also observed [17, 19-22, 26-32]. These observations indicate Sensor 2 expelled Aβ enter HSP's cavity based on its unique toroidal/tower structure.

Zinc ions' mobility from MMP-2's superlattice toroidal array layer efflux toward HSP 60's double-ring structured layer and formed a long-range DET relay was demonstrated in FIGS. 2B and 2D. This research confirms clinical doctors' suggestions for adding zinc ionophores for Covid 19 patients' treatments are sound suggestions that are based on our structural and neuronal circuitry's perspectives [38-39].

Example 5

Figure 33:
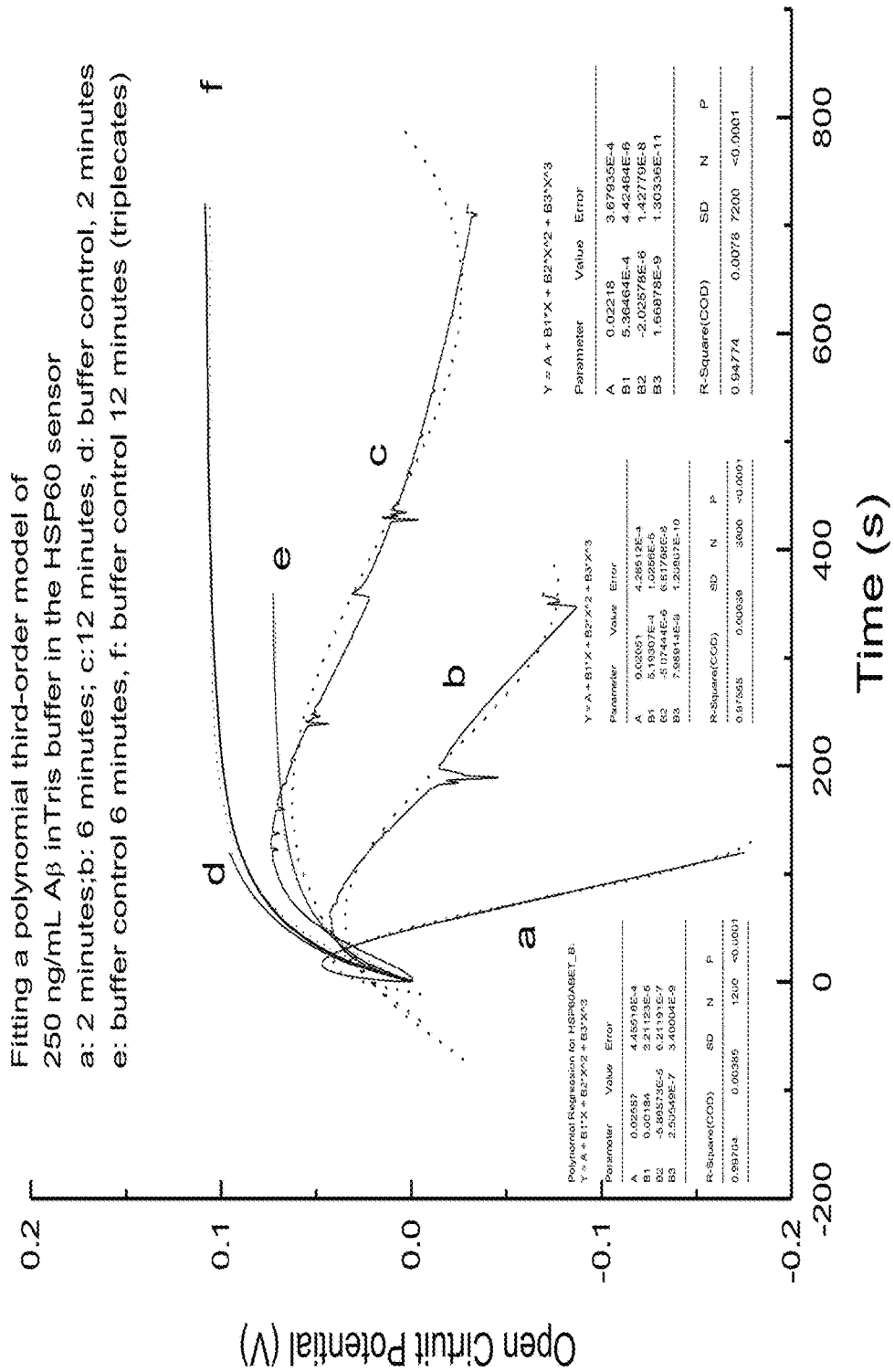
FIG. 33 depicts Sensor 1's 250 ng/mL Aβ effects on the open circuit potential vs. 2-, 6-, and 12-minutes monitoring of the energy change compared with controls.

Pharmacodynamic Study of Inhibitions of Aβ Protein-Refolding in the HSP or HSP/MMP Cavities Using an OPO Method The Open Circuit Potential (OPO) of Device 1. Scientists revealed proteins have a funnel-shaped energy landscape with many high-energy, unfolded structures and only a few low-energy, folded structures [40-42]. We expected our devices can be models for assessing protein-folding energy under an open circuit potential (OPO) condition with current=0. Here, the potential vs. time curve results shows in FIG. 33 for Sensor 1 at the 2-, 6-, and 12-minutes monitoring Aβ folding energy landscape for 250 ng/mL Aβ compared with buffer control. Curves with Aβ alone, potential dropped to negative from original equilibrium state (positive potential) was observed, and the data was compared through fitting a polynomial third-order model of $y = A + \beta1*X + \beta2*X^{\wedge}2 + \beta3*X^{\wedge}3$, β1 refers to the coefficient of the linear component, β2, and β3 refer to the coefficient of the curvature, the values of β1 is 0.00184 at 2 minutes monitoring, which is the highest and the β2 has the most negative down dropping power of $-5.89\ e^{-5}$ than at 4 and 12 minutes monitoring, indicates HSP60 alone is vulnerable to toxins' attack. The three buffer control curves have the same first-order rate constant value of 0.98/s based on the exponential curve fitting Box Lucas 1 MOD model $y = a(1 - e^{-bx})$, as a result, shown a "healthy" HSP60 sensor in the buffer before Aβ attack. FIG. 34 in Panel A, compared the energy landscape curves at a fixed Aβ concentration with various MOX concentrations at 2 minutes compared to 6 minutes monitoring shown in Panel B, demonstrates MOX's ability to impair Aβ folding completely with rate constants 0.9875/s±0.0047 (4 rate constant values) having an error of 0.76% related to the buffer control rate 0.98/s at 2 minutes monitoring; and a mean rate constant of 0.9877/s±0.0061 (5 rate constant values) with an error of 0.79% related to the buffer control rate 0.98/s at 6 minutes monitoring.

Figure 35:
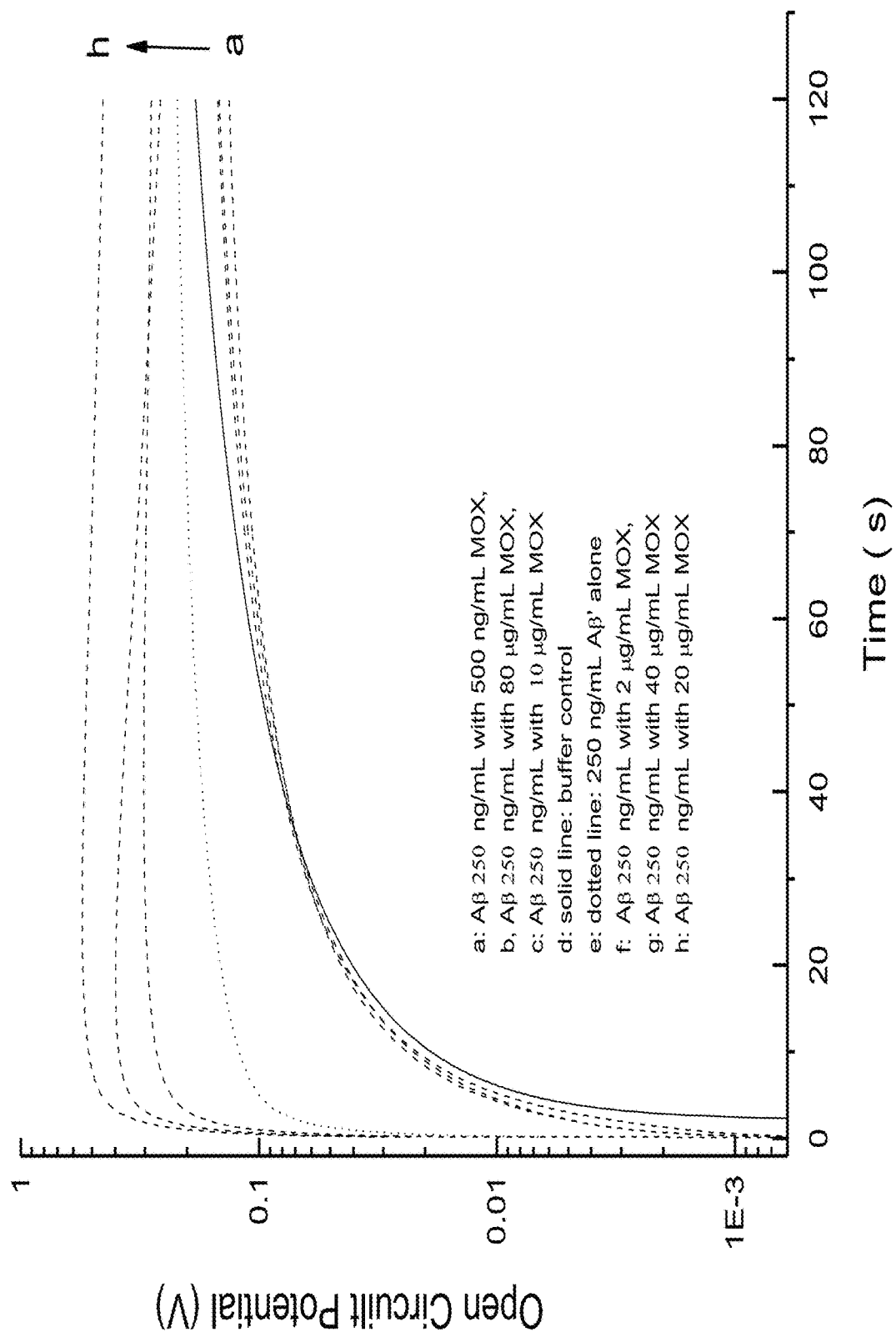
FIG. 35 depicts Sensor 2 (HSP60/MMP2)'s open circuit potential curves at 2 minutes monitoring of the energy change over 500 ng/mL to 80 µg/mL MOX in the presence of 250 ng/mL Aβ compared with controls.

The Open Circuit Potential of Sensor 2. FIG. 35 has the high Aβ concentration that did not cause any oxidative peaks, we further show under different MOX dosages, the potential vs. 2 minutes monitoring curves with the Aβ, no energy dropped to negative, compared with the buffer control was observed in FIG. 7. The mean rate constant value 0.987 $s^{-1}$±0.0045 (n=4), produced an imprecision error of 0.16%, and a good agreement with the control's rate constant was obtained in 99.8%, except MOX at 0.5 μg/mL and 80 μg/mL, because curves drifting occurred and were failed to fit the model.

Example 6

Recovery of the Reversible Membrane Potential (RMP) Through Moxifloxacin

Figure 36A:
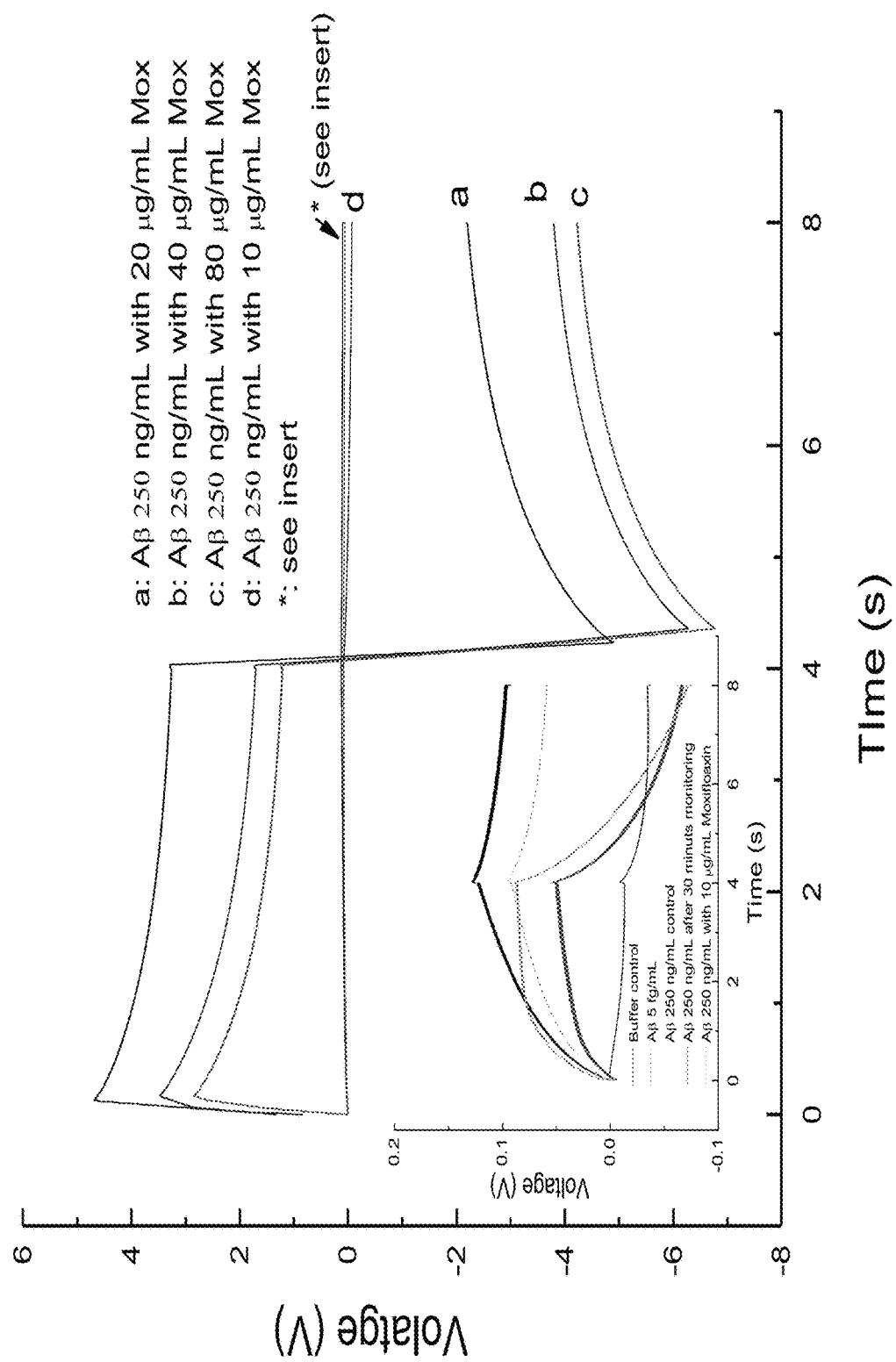
FIG. 36A depicts the potential vs. time curves at ±10 nA at MOX concentration from 10 to 80 µg/mL with or w/o Aβ at 250 ng/mL for Sensor 1 (sample run triplicates).

We first reported using a ratio of action/resting potential to monitor biomarkers of diseases [17-18], because keeping a normal RMP is essential for maintaining healthy cells. Moxifloxacin changed the energy profiles of Sensor 1 as shown in FIG. 36A, that the voltage vs. time curves changed from asymmetric to symmetric when MOX concentration increases from 10 mg/mL to 80 mg/mL in the presence of 250 ng/mL Aβ vs. the controls. FIG. 36B depicts Device 2's profiles with MOX from 0.5 to 80 μg/mL (5 levels), no asymmetric curves were observed under the same experimental conditions. The ratio of results is presented in FIG. 37 compared with the healthy ratio standard. The MOX concentrations are safe in the range up to 20 pg/mL(n=9) in maintaining RMP, and 80 μg/mL is too far from the safe zoon when Aβ 250 ng/mL for Sensor 1. The 40 μg/mL MOX is out of safe zoon by 35.0%±0.2%. In contrast, Sensor 2's ratio values are all located in the safe zoon up to 80 μg/mL MOX (n=18) compared with controls, indicates the HSP60/MMP2 moonlighting network enhanced the health states of cells' RPM by MOX inhibiting HSP's chaperoning function at a clinically harmful level Aft Comparing performances of two devices by linear regression method of |Ap/Rp| vs. MOX concentration with 250 ng/mL Aβ of a severe stage Alzheimer's. From results of L-S regression in FIG. 38 of Table 1, we conclude MOX promoted RMP for both sensors, only Sensor 1 shows a dependency of the Ap/Rp ratio values on the MOX concentration up to 20 μg/mL located in the safety zoon (n=9, p<0.0001). Including the data in 40 and 80 μg/mL, an accuracy of 87.9% (n=15, 5 levels) produced related to the ratio of buffer samples, and a related pooled standard division of 0.3% was reached. Sensor 2 produced 97.3% accuracy result with a MOX range up to 80 μg/mL (n=18), further shows the ratio values are independent on MOX concentrations with an R-value of −0.01 and a slope $-9.4e^{-4}$ and p<0.955, that demonstrated a normal RPM is accomplishable over a wide MOX concentrations in the middle of an Aβ attacking.

Example 7

CONCLUSIONS

The two sensor models for assessing protein refolding energy landscape and evaluations of antibiotic drug impact on the refolding are accomplished by direct real-time monitoring the intrinsic equilibrium energy using the OPO approach through innovations of fabricating nanostructured HSP60 and HSP60/MMP-2 polymer cross-linked SAMs on the electrodes. The results produced correlated well with the evaluation of the RPM effect. Sensor 2 demonstrated the ability in maintaining of normal RPM with a good result of accuracy, and it was not depending on MOX concentrations. The discovery further confirms the moonlighting innate HSP60/MMP-2 network proteins utilized the toroidal array/tower nanostructure and the zinc ions' efflux effect enabled the tunnelling Josephson junctions extended to the HSP cavity. The technology may find therapeutic applications in the future.

What is claimed is:

1. A nanostructured model device of energy sensing and monitoring apparatus comprising arrays of orderly nanotubes parallel oriented forming 3D cross-bar with vertically oriented nanopillars of a membrane through self-assembly affixed onto an electrode; the membrane comprises active sites of an innate protein cross-linked with organic conductive polymers.

2. The nanostructured model device of energy sensing and monitoring apparatus according to claim 1, wherein the innate protein comprises a heat shock protein (HSP) comprising double-truncated "donuts" cluster of two-heptametrical rings made up tetradecamer oriented chaperone HSP60, and a cluster of U-shape HSP60 subunits.

3. The nanostructured model device of energy sensing and monitoring apparatus according to claim 1, wherein the array 3D cross-bars comprise triacetyl-l3-cyclodextrin (TCD) . . . glycol diglycidyl ether (PEG) . . . poly (4-vinylpyridine) (PVP) forming orderly array straight nanotubes horizontally covered by the electrode, where cross-linked HSP protein forms vertically oriented nanopillars either without pores or with pores.

4. The nanostructured model device of energy sensing and monitoring apparatus according to claim 1, wherein HSP protein mixture solutions cross-link with a moonlighting network protein membrane comprising of an array toroidal superlattice matrix comprises matrix metalloproteinase (MMP) cross-linked with TCD, PEG and PVP, formed a multiple-layered SAMs having horizontal oriented toroidal superlattice on the electrode and having vertically oriented towers aligned with the toroidal cavities.

5. The nanostructured model device of energy sensing and monitoring apparatus according to claim 4, wherein a Friedel-oscillation is observed in superlattice toroidal/Tower membranes thus promoting superconductivity based on array of Josephson Junction high frequency oscillation.

6. The nanostructured model device of energy sensing and monitoring apparatus according to claim 5, wherein inhibited high concentration toxic protein of (3-amyloid (A3) refolding in a HSP cavity through monitoring the energy landscape change at real-time of 2 minutes with or without antibiotic drugs presence under dosages between 0.5 pg/mL and 80 pg/mL (6 levels) compared with the controls using an Open Circuit Potential (OPO) method.

7. The nanostructured model device of energy sensing and monitoring apparatus according to claim 6, wherein the antibiotic drug is moxifloxacin (MOX).

8. The nanostructured model device of energy sensing and monitoring apparatus according to claim 7, wherein a hSP60/MMP-2 device demonstrated the direct real-time monitoring the changes of protein refolding energy landscape correlated for maintaining a Reversible Membrane Potential (RMP) with results of accuracy 97.3% and imprecision 0.05%, which was not depending on MOX concentration conducted by a Double-step chronopotentiometric (DSCPO) method.

9. The nanostructured model device of energy sensing and monitoring apparatus according to claim 1, wherein a HSP60 device impaired Ap's refolding in a HSP's cavity in real-time monitoring of the open circuit potential (OPO) compared with controls of AR (negative energy landscape) and buffer controls, respectively in the presence of moxifloxacin (MOX) between 0.5-80 ptg/mL dosages.

10. The nanostructured model device of energy sensing and monitoring apparatus according to claim 1, wherein a HSP60 device's membrane's AFM image has a ratio of width/length of the HSP cluster of 0.90, which is a good agreement with a cryo-EM of 98%.

11. A method of using a nanostructured model device of energy sensing and monitoring apparatus further including the use for direct measuring protein bio-communication in an intrinsic energy landscape change in real-time using an OPO method comprising: a) obtaining a sample immersed in a medium which can be detected; b) contacting the sample with a device, and the device comprises either arrays of orderly oriented nanotubes/nanopillars with at least one HSP component, or HSP/MMP combinations forming nanostructured toroidal/tower structure, to form 3D cross-bars of a membrane affixed onto said an electrode; c) connecting two leads to a cathode and an anode electrode with zero current setting; and d) measuring the voltage change in the analyte.

* * * * *